(12) United States Patent
Prestwich et al.

(10) Patent No.: US 8,399,430 B2
(45) Date of Patent: *Mar. 19, 2013

(54) ALKYLATED SEMI SYNTHETIC GLYCOSAMINOGLYCOSAN ETHERS, AND METHODS FOR MAKING AND USING THEREOF

(75) Inventors: Glenn D. Prestwich, Eastsound, WA (US); Jianxing Zhang, Salt Lake City, UT (US); Thomas P. Kennedy, Charlotte, NC (US); Narayanam V. Rao, Salt Lake City, UT (US); Xiaoyu Xu, Foster City, CA (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/870,774

(22) Filed: Aug. 27, 2010

(65) Prior Publication Data
US 2011/0082104 A1    Apr. 7, 2011

Related U.S. Application Data

(63) Continuation-in-part of application No. PCT/US2009/039498, filed on Apr. 3, 2009.

(60) Provisional application No. 61/042,310, filed on Apr. 4, 2008.

(51) Int. Cl.
*A61K 31/175* (2006.01)
*A61K 31/70* (2006.01)
*A01N 43/04* (2006.01)
*C07H 5/04* (2006.01)

(52) U.S. Cl. ............. 514/54; 514/62; 536/55.1

(58) Field of Classification Search .......... None
See application file for complete search history.

(56) References Cited

U.S. PATENT DOCUMENTS

| | | | |
|---|---|---|---|
| 4,814,437 A | 3/1989 | de Belder et al. |
| 6,288,043 B1 | 9/2001 | Spiro et al. |
| 6,339,074 B1 | 1/2002 | Cialdi et al. |
| 6,833,363 B2 | 12/2004 | Renier |
| 7,202,230 B2 | 4/2007 | Rivarossa |
| 7,683,038 B2 | 3/2010 | Bellini et al. |
| 2003/0199687 A1 | 10/2003 | Yalpani |
| 2005/0203056 A1 | 9/2005 | Ulmer et al. |
| 2007/0054878 A1 | 3/2007 | Venbrocks |
| 2008/0182982 A1 | 7/2008 | Kumar et al. |
| 2008/0306023 A1 | 12/2008 | Rinaudo |
| 2009/0105463 A1 | 4/2009 | Berry et al. |
| 2009/0197807 A1 | 8/2009 | Callegaro |

(Continued)

FOREIGN PATENT DOCUMENTS
DE    19813234 A1    9/1999
DE    102005004643 A1    8/2006

(Continued)

OTHER PUBLICATIONS

Tsutomu Nagira, et al., "Effects of sulfated hyaluronan on keratinocyte differentiation and Wnt and Notch gene expression", Biomaterials, Feb. 2007, pp. 844-850, vol. 2(5) Publ. Elsevier BV, Amsterdam, The Netherlands and New York, New York.

(Continued)

*Primary Examiner* — Bong-Sook Baek
(74) *Attorney, Agent, or Firm* — Ted W. Whitlock

(57) ABSTRACT

Described herein is the synthesis of alkylated and semi-synthetic glycosaminoglycosan ethers, referred to herein as "SAGEs." The synthesis of sulfated alkylated SAGEs is also described. The compounds described herein are useful in a number of applications including wound healing, drug delivery, and the treatment of a number of inflammatory diseases and skin disorders.

24 Claims, 37 Drawing Sheets

U.S. PATENT DOCUMENTS

| 2009/0202639 A1 | 8/2009 | Bellini |
| 2009/0226499 A1 | 9/2009 | Wisniewski et al. |
| 2009/0285850 A1 | 11/2009 | Dillon |

FOREIGN PATENT DOCUMENTS

| JP | 11279042 A | 10/1999 |
| JP | 2001097997 A | 4/2001 |
| WO | WO 99/43728 A1 | 9/1999 |
| WO | WO 2005/056608 | 6/2005 |
| WO | WO 2007/006403 A2 | 1/2007 |
| WO | WO 2007/043050 A2 | 4/2007 |
| WO | WO 2008/008859 | 1/2008 |
| WO | WO 2009/013162 A1 | 1/2009 |

OTHER PUBLICATIONS

Satoh, T., et al., The Basic Research on Physiological Property of Functionalized Hyaluronan (II): Effect of Sulfated Hyaluronan on Histamine Release from the Mast Cell, Fiber, 2004, pp. 137-143, Vol. 60, No. 5, Publ. The Society of Fiber Science and Technology, Japan.

Roger W. Jeanloz, The Methyl Ester of Methylated Hyaluronic acid, J Biol. Chem, May 1952, pp. 141-150, Vol. 197 No. 1, Publ. American Society for Biochemistry and Molecular Biology, Bethesda, Maryland.

M. Kaye et al., Methylation Studies on Hyaluronic Acid, Biochem J., 1951, vol. 48, p. 249, Publ. Portland Press Ltd on behalf of the Biochemical Society, Colchester, UK.

Benesova, K., et al., "Stability evaluation of n-alkyl hyaluronic acid derivatives by DSC and TG measurement" J. Therm. Analys. Calorim., Feb. 1, 2006, vol. 83(2) pp. 341-334, Kluwer Academ. Publ., DO.

Abatangelo, G., et al., "Biocompatibility and enzymatic degradation studies on sulphated hyaluronic acid derivatives" Biomaterials, 18(21), Jan. 1, 2007, p. 1411-1415 (Elsevier Sci Pub, Great Britain).

Dausse et al. "Cartilage Repair Using New Polysaccharidic Biomaterials: Macroscopic, Histological and Biochemical Approaches in a Rat Model of Cartilage Defect" Osteoarthritis and Cartilage, 11: 16-28 (2003), Elsevier Science Ltd., Great Britain.

Mracek et al. "The Diffusion Process of Sodium Hyaluronate (Na-HA) and Na-HA-n-Alkyl Derivatives Films Swelling" J. Biomed. Mater. Res. Part A, 83A/1; 184-190, (2007), Wiley P Wiley Periodicals, Inc., Wilmington, Delaware USA.

International Search Report for PCT application No. PCT/US09/39498 mailed on Oct. 13, 2009.

FIG. 2

| | |
|---|---|
| GM-211101 | structure with OCH$_2$CF$_2$CF$_3$ |
| GM-311101 | structure with OCH$_2$(CF$_2$)$_2$CF$_3$ |
| GM-111101 | structure with OMe |
| GM-211101 | structure with OCH$_2$CF$_2$CF$_3$ |
| GM-311201 | structure with OCH$_2$(CF$_2$)$_2$CF$_3$ |
| GM-111201 | structure with OMe |

FIG. 2 CONT.

| | |
|---|---|
| GM-232101 | Structure with HCO₂Na, NaO₃SO, RO, OR, OCH₂CF₂CF₃, HN-C(=O)CH₃, subscript x |
| GM-332101 | Structure with HCO₂Na, NaO₃SO, RO, OR, OCH₂(CF₂)₂CF₃, HN-C(=O)CH₃, subscript x |
| GM-132101 | Structure with HCO₂Na, NaO₃SO, RO, OR, OMe, HN-C(=O)CH₃, subscript x |
| GM-232201 | Structure with HCO₂Na, NaO₃SO, RO, OR, OCH₂CF₂CF₃, HN-C(=O)CH₃, subscript x |
| GM-332201 | Structure with HCO₂Na, NaO₃SO, RO, OR, OCH₂(CF₂)₂CF₃, HN-C(=O)CH₃, subscript x |
| GM-132201 | Structure with HCO₂Na, NaO₃SO, RO, OR, OMe, HN-C(=O)CH₃, subscript x |

R = H, alkyl, or SO₃Na depending upon the degree of alkylation and sulfation

FIG. 2 CONT.

ALKYLATED SEMI SYNTHETIC GLYCOSAMINOGLYCOSAN ETHERS, AND METHODS FOR MAKING AND USING THEREOF

CROSS REFERENCE TO RELATED APPLICATIONS

This is a continuation-in-part application of International Application No. PCT/US09/039,498, filed Apr. 3, 2009, which claims the benefit of U.S. provisional application Ser. No. 61/042,310, filed Apr. 4, 2008. These applications are hereby incorporated by reference in their entirety for all of their teachings.

BACKGROUND

Inflammatory diseases such as psoriasis, dermatitis, acne, rosacea, photo-dermal ageing, and numerous diseases linked to RAGE-mediated signaling plague people worldwide. To put these diseases into perspective, the National Psoriasis Foundation reports that psoriasis alone afflicts 2-3% of the world's population or approximately 125 million people. These inflammatory conditions can be aesthetically unpleasing and can create serious health issues if left untreated. Conventionally accepted treatments of these conditions may involve UV phototherapy, corticosteroids and glucocorticoids, acitretin, cyclosporine, and methotrexate. However, each of these treatments may cause serious side effects ranging from immune suppression and liver disease to thinning skin and causing birth defects. Due to partial or complete ineffectiveness, these treatments often leave patients unsatisfied with their results.

In addition to the treatments mentioned above, heparin treatment has also been experimentally explored. Heparin, a sulfated polysaccharide, has traditionally been used almost exclusively as an anti-coagulant, but its anti-inflammatory properties are well known. Heparin and its derivatives have shown some promise in treating these inflammatory diseases. Particularly heparin and its derivatives disrupt at least three important events in inflammatory cascades. First, heparin attaches to and blocks the leukocyte integrins P- and L-selectin. Second, heparin and its derivatives reduce the inflammatory cascade by binding to and inhibiting the cationic PMN protease human leukocyte elastase and cathepsin G, which reduces proteolytic tissue injury by PMNs that escape the first heparin barrier of selectin inhibition. Third, heparin and its derivatives potentially inhibit the interaction of the receptor for advanced glycation end-products (RAGE) with its ligands. Although heparin and its derivatives have shown promise in treating these inflammatory diseases, treatment with heparin and its derivatives exhibits several major drawbacks. First, heparin and its derivatives are porcine-derived; thus leading to concerns of cross-species transfer of viruses. Second, because of heparin's anticoagulant properties, diabetics treated with this compound are at risk of excessive bleeding. Third, heparin may induce thrombocytopenia in certain individuals who produce an antibody to the complex of heparin with the cationic protein platelet factor-4 (PF-4), resulting in catastrophic platelet aggregation and generalized paradoxical arterial and venous clotting. Thus, an important unmet need is to formulate compounds which may be used to treat inflammatory diseases while avoiding the myriad of side effects seen in other treatments.

SUMMARY OF THE INVENTION

Described herein are alkylated semisynthetic glycosaminoglycosan ethers, referred to herein as "SAGEs," sulfated alkylated SAGEs, and the synthesis of these compounds. The compounds described herein are useful in a number of therapeutic and cosmetic applications and the treatment of a number of inflammatory diseases and skin disorders. The advantages of the invention will be set forth in part in the description which follows, and in part will be clear from the description, or may be learned by practice of the aspects described below. The advantages described herein will be realized and attained by means of the elements and combinations particularly pointed out in the specification and the appended claims. It is to be understood that both the foregoing general description and the following detailed description are exemplary and explanatory only and are not restrictive.

Specifically described and claimed are compounds for the treatment, prevention, or inhibition of a dermatological condition or symptom associated with said dermatological condition, said compounds comprising modified hyaluronans, or the pharmaceutically acceptable salts or esters thereof, comprising at least one sulfate group and having at least one primary C-6 hydroxyl position of an N-acetyl-glucosamine residue comprising a $C_1$-$C_{10}$ alkyl group. The hyaluronan to be modified has a molecular weight from 40 kDa to 2,000 kDa prior to alkylation or fluoroalkylation.

The alkylated and sulfated compounds of the subject invention preferably have an alkyl group selected from the group consisting of methyl, ethyl, propyl and butyl, and a more preferred compound comprises a methyl group as the alkyl group. In addition, a preferred compound of the subject invention comprises a sulfate group at the C-2 or C-3 hydroxyl position of a glucuronic acid moiety, and more preferably, at the C-2 and C-3 positions. An additional embodiment can comprise a sulfate at the C-4 hydroxyl position of the N-acetyl glucosamine moiety or any combination of sulfation at the C-2, C-3 positions of the glucuronic acid moiety, or C-4 hydroxyl position of the N-acetyl glucosamine moiety of the compound. The sulfated compounds can have a degree of sulfation from 0.5 to 3.5 per disaccharide unit, and a molecular weight of 2 kDa to 10 kDa.

The compounds of the subject invention can further be admixed with pharmaceutically acceptable excipients to form a pharmaceutical composition comprising an alkylated and/or sulfated compound of the subject invention. These pharmaceutical compositions can be formulated for topical administration.

Methods of treating or preventing a dermatological condition or symptom associated with said dermatological condition using the disclosed alkylated and sulfated compounds comprise the steps of (a) providing a compound as described, and (b) administering an effective amount of said compound or a composition comprising said compound, to a patient suffering from these dermatological conditions or symptom associated with these dermatological conditions. The conditions treated with the compounds or compositions of the invention include rosacea, psoriasis, acne vulgaris, hair loss, atopic dermatitis, and actinic keratosis. The subject method preferably comprises topically administering said compound to the skin.

BRIEF DESCRIPTION OF THE DRAWINGS

The accompanying drawings, which are incorporated in and constitute a part of this specification, illustrate several aspects described below.

FIG. 16 shows (a) H&E-stained cross-sectional view of a LL-37 injected skin sample, (b) H&E-stained cross-sectional view of HA treatment in LL-37 injected skin region, (f) H&E-stained cross-sectional view of SAGE (GM-111101) treatment in LL-37 injected skin region, (g) MPO activity measurement of LL-37 injection model with HA and SAGE treatment, (h) Area of erythema illustration and (g) erythema score demonstration of LL-37 rosacea model with HA and SAGE treatment.

DETAILED DESCRIPTION

Figure 1:
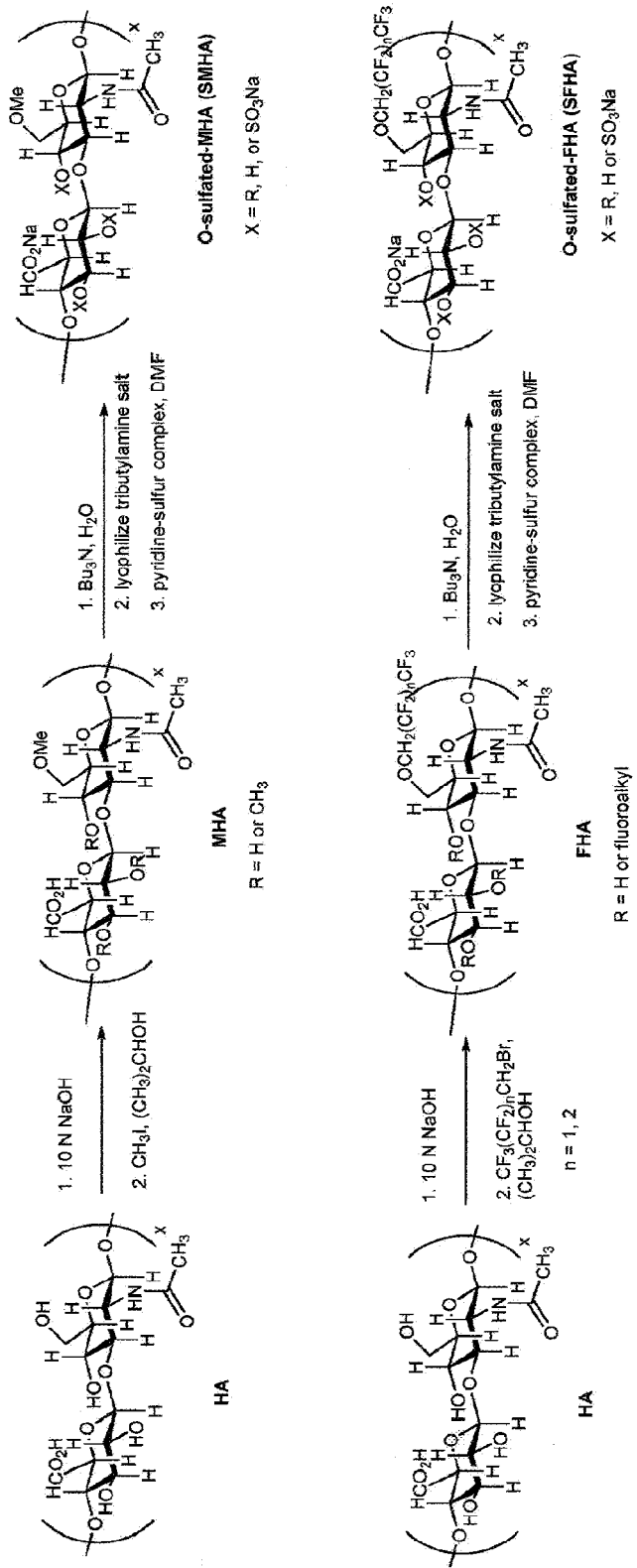
FIG. 1 shows a synthetic scheme for producing alkylated and fluoroalkylated hyaluronan and sulfated derivatives thereof.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," an and the include plural referents unless the context clearly dictates otherwise. Thus, for example, reference to "a pharmaceutical carrier" includes mixtures of two or more such carriers, and the like. "Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, hyaluronan that contains at least one —OH group can be represented by the formula Y—OH, where Y is the remainder (i.e., residue) of the hyaluronan molecule.

The term "treat" as used herein is defined as maintaining or reducing the symptoms of a pre-existing condition. The term "prevent" as used herein is defined as eliminating or reducing the likelihood of the occurrence of one or more symptoms of a disease or disorder. The term "inhibit" as used herein is the ability of the compounds described herein to completely eliminate the activity or reduce the activity when compared to the same activity in the absence of the compound.

Described herein are alkylated hyaluronan or derivatives thereof. In one aspect, at least one primary C-6 hydroxyl proton of the N-acetyl-glucosamine residue of hyaluronan is substituted with an alkyl group. The term "alkyl group" as used herein is a branched or unbranched saturated hydrocarbon group of 1 to 24 carbon atoms. In one aspect, the alkyl group is a $C_1$-$C_{10}$ branched or straight chain alkyl group. The alkyl group can be unsubstituted or substituted. The term "unsubstituted" with respect to the alkyl group is a saturated hydrocarbon composed only of hydrogen and carbon. Examples of unsubstituted alkyl groups include, but are not limited to, methyl, ethyl, n-propyl, isopropyl, n-butyl, isobutyl, f-butyl, pentyl, hexyl, heptyl, octyl, nonyl, decyl, tetradecyl, hexadecyl, eicosyl, tetracosyl and the like.

Described herein are methods for alkylating SAGEs. In one aspect, the SAGEs are produced by (a) reacting the hyaluronan or a derivative thereof with a sufficient amount of base to deprotonate at least one primary C-6 hydroxyl proton of the N-acetyl-glucosamine residue, and (b) reacting the deprotonated hyaluronan or a derivative thereof with an alkylating agent for a sufficient time and concentration to alkylate at least one deprotonated primary C-6 hydroxyl group. It will be understood by those skilled in the art that the basic conditions may also lead to cleavage of the glycosidic linkage, leading to lower molecular weight hyaluronan derivatives during the modification process. It will also be understood that the basic conditions deprotonate the acid to the carboxylate, and the secondary hydroxyl groups, and that each of these nucleophilic moieties may participate in the ensuing alkylation in proportion to their relative abundance at equilibrium and the nucleophilicity of the anionic species. For example, 2-O and/or 3-O hydroxyl protons of the glucuronic acid moiety or the C-4 hydroxyl position of the N-acetyl glucosamine moiety can be deprotonated and alkylated. An example of this is depicted in FIG. 1, where R can be hydrogen, an alkyl group, or an alkyl group. The hyaluronan starting material can exist as the free acid or the salt thereof.

Derivatives of hyaluronan starting material can also be used herein. The derivatives include any modification of the hyaluronan prior to the alkylation step. A wide variety of molecular weight hyaluronan can be used herein. In one aspect, the hyaluronan has a molecular weight greater than 10 kDa prior to alkylation. In another aspect, the hyaluronan has a molecular weight from 25 kDa to 1,000 kDa, 100 kDa to 1,000 kDa, 25 kDa to 500 kDa, 25 kDa to 250 kDa, or 25 kDa to 100 kDa prior to alkylation. In certain aspects, the hyaluronan starting material or a derivative thereof is not derived from an animal source. In these aspects, the hyaluronan can be derived from other sources such as bacteria. For example, a recombinant *B. subtilis* expression system or *Streptomyces* strain can be used to produce the hyaluronan starting material.

The hyaluronan starting material or derivative thereof is initially reacted with a sufficient amount of base to deprotonate at least one primary C-6 hydroxyl proton of the N-acetyl-glucosamine residue. The selection of the base can vary. For example, an alkali hydroxide such as sodium hydroxide or potassium hydroxide can be used herein. The concentration or amount of base can vary depending upon the desired degree of alkylation. In one aspect, the amount of base is sufficient to deprotonate at least 0.001% of the primary C-6 hydroxyl protons of the N-acetyl-glucosamine residue of the hyaluronan starting material or derivative thereof. In other aspects, the amount of base is sufficient to deprotonate from 0.001% to 50%, 1% to 50% 5% to 45%, 5% to 40%, 5% to 30%, 5% to 20%, 10% to 50%, 20% to 50%, or 30% to 50% of the primary C-6 hydroxyl protons of the N-acetyl-glucosamine residue of the hyaluronan starting material or derivative thereof. It is understood that the more basic the solution, the more likely are chain cleavage reactions and the higher the degree of alkylation that can be achieved. For example, other hydroxyl groups present on hyaluronan (e.g., 2-OH and/or 3-OH can be alkylated). In one aspect, all of the hydroxyl groups present on hyaluronan can be alkylated. In other aspects, 0.001%, 0.01%, 0.1%, 1%, 5%, 10%, 20%, 30%, 40%, 50%, 60%, 70%, 80%, 90%, 95%, 100%, or any range thereof of hydroxyl protons present on hyaluronan can be deprotonated and subsequently alkylated.

After the hyaluronan starting material or derivative thereof has been treated with a base, the deprotonated hyaluronan is reacted with an alkylating agent to produce the SAGE. Examples of alkylating agents include, but are not limited to, an alkyl halide. Alkyl bromides and iodides are particularly useful. Alkylating agents commonly used in organic synthesis can be used herein.

An exemplary synthetic procedure for making alkylated SAGEs is provided in FIG. 1. Referring to FIG. 1, hyaluronan (HA) is treated with a base (e.g., NaOH) and an alkylating agent (e.g., $CH_3I$) to methylate a primary C-6 hydroxyl proton of the N-acetyl-glucosamine residue of hyaluronan and produce methylated hyaluronan (MHA). FIG. 1 also provides an exemplary synthetic procedure for making a fluoroalkylated hyaluronan (FHA) using a fluoroalkylating agent (e.g., $CF_3(CF_2X_1CH_2Br)$, which is a substituted alkyl group as defined herein.

In certain aspects, it is desirable to sulfate the alkylated SAGEs described above. In one aspect, the alkylated SAGE is sulfated by reacting the alkylated SAGE with a sulfating agent to produce a sulfated product. The degree of sulfation can vary from partial sulfation to complete sulfation. In general, free hydroxyl groups present on the alkylated hyaluronan or a derivative thereof can be sulfated. In one aspect, at least one C-2 hydroxyl proton and/or C-3 hydroxyl proton is substituted with a sulfate group. An additional embodiment can comprise a sulfate at the C-4 hydroxyl position of the N-acetyl glucosamine moiety or any combination of sulfation at the C-2, C-3 positions of the glucuronic acid moiety and C-4 hydroxyl position of the N-acetyl glucosamine moiety of the compound. The degree of sulfation can be from 0.5, 1.0, 1.5, 2.0, 2.5, 3.0, 3.5 or any range thereof per disaccharide unit of the alkylated SAGE. In one aspect, the alkylated SAGE can be treated with a base to deprotonate one or more hydroxyl protons followed by the addition of the sulfating agent. The sulfating agent is any compound that reacts with a hydroxyl group or deprotonated hydroxyl group to produce a sulfate group. The molecular weight of the SAGE can vary depending upon reaction conditions. In one aspect, the molecular weight of the SAGE is from 2 kDa to 500 kDa, 2 kDa to 250 kDa, 2 kDa to 100 kDa, 2 kDa to 50 kDa, 2 kDa to 25 kDa, or from 2 kDa to 10 kDa. FIG. 1 depicts an exemplary synthesis of sulfated alkylated SAGEs (SMHA and SFHA, respectively).

Figure 2:
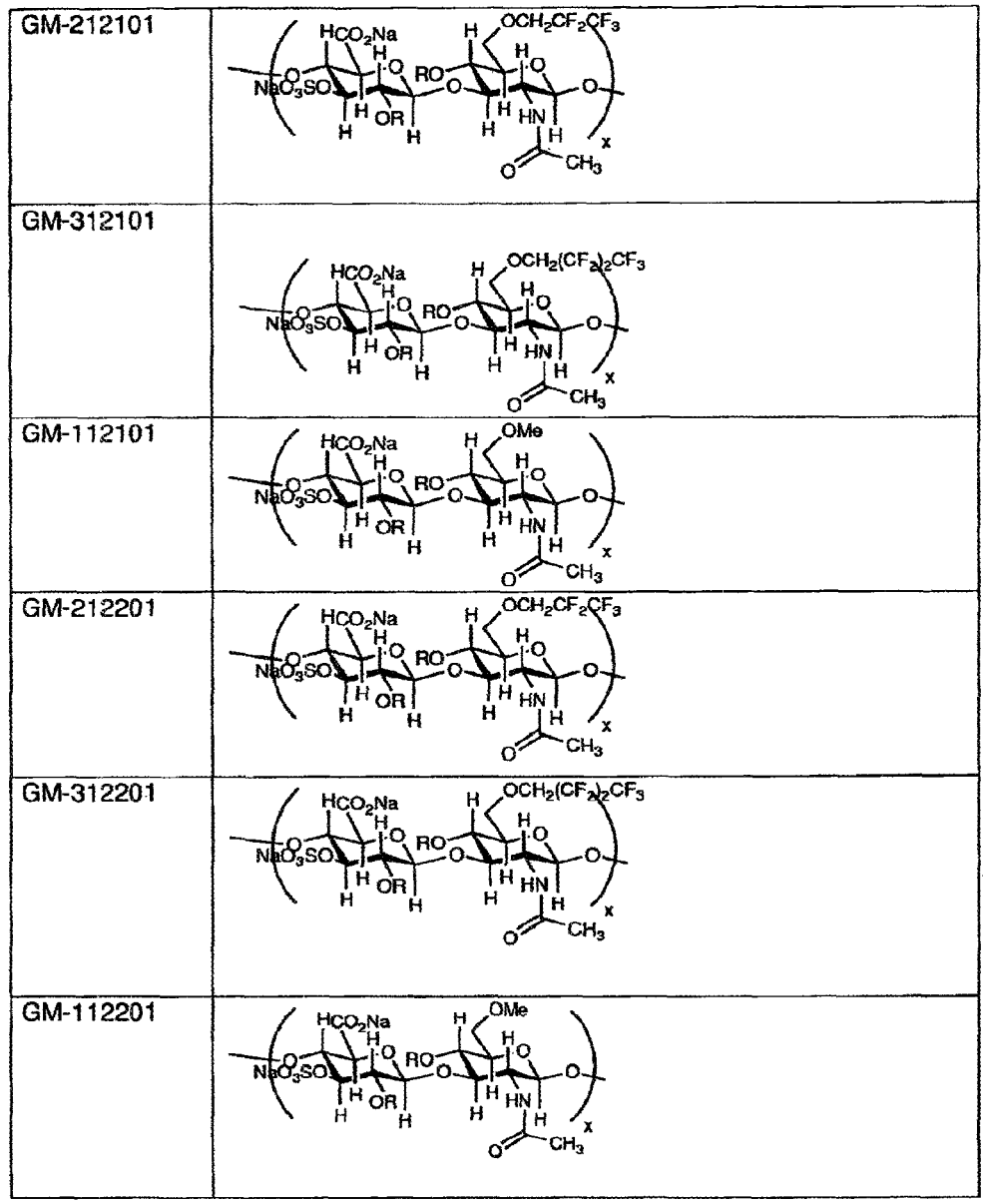
FIG. 2 shows the structures of several exemplary SAGEs.

FIG. 2 provides the structures of several exemplary SAGEs. Each SAGE is identified by the code GM-XYSTZZ, where:
  X=type of alkyl group, where 1=methyl, 2=pentafluoropropyl, 3=heptafluorobutyl, 4=benzylglycidyl ether;
  Y=size of HA, where 1=low, 2=medium, 3=high;
  S=degree of sulfation, where 1=partial, 2=full
  T=degree of alkylation, where 1=low, 2=high;
  ZZ=sequential lot number 01 or 02, where the 02 has been made and has all the same properties as the 01 batch.

Table 1, below, provides a list of several SAGEs as defined by the code system above.

In one aspect, the alkyl group of the SAGE is methyl and at least one C-2 hydroxyl proton and/or C-3 hydroxyl proton of hyaluronan is substituted with a sulfate group. In another aspect, the alkyl group of the SAGE is methyl, at least one C-2 hydroxyl proton and/or C-3 hydroxyl proton of hyaluronan is substituted with a sulfate group, and the compound has a molecular weight of 2 kDa to 200 kDa after alkylation. An example of such a compound is GM-111101 as shown in FIG. 2. An additional embodiment can comprise a sulfate at the C-4 hydroxyl position of the N-acetyl glucosamine moiety or any combination of sulfation at the C-2, C-3 positions of the glucuronic acid moiety and C-4 hydroxyl position of the N-acetyl glucosamine moiety of the compound.

The modified hyaluronans described herein can be prepared from different sources of hyaluronic acid with different polydispersities and initial average molecular weights. The in vitro biochemical results, in vivo biological activities, and alkylation/sulfation levels can vary based on the size and solubility of the starting HA. For example, starting with poorly soluble HA of size 60-70 kDa resulted in low levels of methylation, sulfation, and dramatically reduced biological activities. In contrast, starting with readily soluble HA of sizes 40-60 kDa (whether obtained commercially at this size

TABLE 1

| SAGE # | CHEMICAL NAME | MW(starting) | MW(GPC) | Alkylation | Alkylation SD | Sulfation |
|---|---|---|---|---|---|---|
| GM-211101 | LMW—P—OSFHA-1(DS 1) | 53K | 6K | Pentafluoropropyl (Pfp) | 1 | 1.0-1.5 |
| GM-311101 | LMW—P—OSFHA-2(DS 1) | 53K | 5.8K | Heptafluorobutyl (Hfb) | 1 | 1.0-1.5 |
| GM-111101 | LMW—P—OSMeHA(DS 1) | 53K | 5.6K | Methyl (Me) | 1 | 1.0-1.5 |
| GM-211201 | LMW—P—OSFHA-1(DS 2) | 53K | 6K | pentafluoropropyl | 2 | 1.0-1.5 |
| GM-311201 | LMW—P—OSFHA-2(DS 2) | 53K | 5.6K | heptafluorobutyl | 2 | 1.0-1.5 |
| GM-111201 | LMW—P—OSMeHA(DS 2) | 53K | 5.5K | methyl | 2 | 1.0-1.5 |
| GM-231101 | P—OSFHA-1(DS 1) | 950K | 112k | Pentafluoropropyl | 1 | 1.0-1.5 |
| GM-331101 | P—OSFHA-2(DS 1) | 950K | 110k | Heptafluorobutyl (Hfb) | 1 | 1.0-1.5 |
| GM-131101 | P—OSMeHA(DS 1) | 950K | 123k | methyl | 1 | 1.0-1.5 |
| GM-231201 | P—OSFHA-1(DS 2) | 950K | 108k | pentafluoropropyl | 2 | 1.0-1.5 |
| GM-331201 | P—OSFHA-2(DS 2) | 950K | 130k | heptafluorobutyl | 2 | 1.0-1.5 |
| GM-131201 | P—OSMeHA(DS 2) | 950K | 120K | methyl | 2 | 1.0-1.5 |
| GM-212101 | LMW—F—OSFHA-1(DS 1) | 53K | 5k | pentafluoropropyl | 1 | 1.5-2.0 |
| GM-312101 | LMW—F—OSFHA-2(DS 1) | 53K | 4.8k | heptafluorobutyl | 1 | 1.5-2.0 |
| GM-112101 | LMW—F—OSMeHA(DS 1) | 53K | 5.6k | methyl | 1 | 1.5-2.0 |
| GM-212201 | LMW—F—OSFHA-1(DS 2) | 53K | 6K | pentafluoropropyl | 2 | 1.5-2.0 |
| GM-312201 | LMW—F—OSFHA-2(DS 2) | 53K | 6K | heptafluorobutyl | 2 | 1.5-2.0 |
| GM-112201 | LMW—F—OSMeHA(DS 2) | 53K | 5.4k | methyl | 2 | 1.5-2.0 |
| GM-232101 | F—OSFHA-1(DS 1) | 950K | 110k | pentafluoropropyl | 1 | 1.5-2.0 |
| GM-332101 | F—OSFHA-2(DS 1) | 950K | 105k | heptafluorobutyl | 1 | 1.5-2.0 |
| GM-132101 | F—OSMeHA(DS 1) | 950K | 112k | Methyl | 1 | 1.5-2.0 |
| GM-232201 | F—OSFHA-1(DS 2) | 950K | 120k | pentafluoropropyl | 2 | 1.5-2.0 |
| GM-332201 | F—OSFHA-2(DS 2) | 950K | 118k | heptafluorobutyl | 2 | 1.5-2.0 |
| GM-132201 | F—OSMeHA(DS 2) | 950K | 116K | methyl | 2 | 1.5-2.0 |
| GM-431101 | P—OSBGHA | 950K | 105k | benzyl glycidyl ether (BG) | <1 | |
| GM-432101 | F—OSBGHA | 950K | 110k | benzyl glycidyl ether | <1 | |
| GM-411101 | P—OSBGHA | 53K | 6K | benzyl glycidyl ether | <1 | |
| GM-412101 | F—OSBGHA | 53K | 5.6k | benzyl glycidyl ether | <1 | |

GM-XYSTZZ coding
X = alkyl
1 = Me
2 = Pfp
3 = Hfb
4 = BG
Y = MW
1 = Low
2 = Medium
3 = High
S = sulfation
1 = partial
2 = full
T = Alkylation
1 = Low SD
2 = high SD
ZZ = Sequential no.

or prepared by partial depolymerization of a higher molecular weight HA starting material) resulted in reproducible levels of methylation, sulfation, and high biological activity.

Any of the alkylated SAGEs described herein can be the pharmaceutically acceptable salt or ester thereof. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of structural formula I to base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds, as illustrated in the examples below- and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine. Also, the esters can be fatty acid esters. For example, the palmitic ester has been prepared and can be used as an alternative esterase-activated prodrug.

The SAGEs described herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. For example, the pH of the composition is from about 5 to about 6, which is suitable for topical applications. Additionally, the pharmaceutical compositions can include carriers, thickeners, diluents, preservatives, surface active agents and the like in addition to the compounds described herein.

The pharmaceutical compositions can also include one or more active ingredients used in combination with the compounds described herein. The resulting pharmaceutical composition can provide a system for sustained, continuous delivery of drugs and other biologically-active agents to tissues adjacent to or distant from the application site. The biologically-active agent is capable of providing a local or systemic biological, physiological or therapeutic effect in the biological system to which it is applied. For example, the agent can act to control and/or prevent infection or inflammation, enhance cell growth and tissue regeneration, control tumor growth, act as an analgesic, promote anti-cell attachment, reduce alveolar bone and tooth loss, inhibit degeneration of cartilage and weight bearing joints, and enhance bone growth, among other functions. Additionally, any of the compounds described herein can contain combinations of two or more pharmaceutically-acceptable compounds.

Examples of such compounds include, but are not limited to, antimicrobial agents, antiinflammatory agents, anesthetics, and the like. Methods for using these compositions as drug delivery devices are described in detail below.

The pharmaceutical compositions can be prepared using techniques known in the art. In one aspect, the composition is prepared by admixing a SAGE described herein with a pharmaceutically-acceptable compound and/or carrier. The term "admixing" is defined as mixing the two components together so that there is no chemical reaction or physical interaction. The term "admixing" also includes the chemical reaction or physical interaction between the compound and the pharmaceutically-acceptable compound. Covalent bonding to reactive therapeutic drugs, e.g., those having nucleophilic groups, can be undertaken on the compound. Second, non-covalent entrapment of a pharmacologically active agent in a cross-linked polysaccharide is also possible. Third, electrostatic or hydrophobic interactions can facilitate retention of a pharmaceutically-acceptable compound in the compounds described herein.

It will be appreciated that the actual preferred amounts of SAGE in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999).

The pharmaceutical compositions described herein can be administered in a number of ways depending on whether local or systemic treatment is desired, and on the area to be treated. Administration can be topically (including ophthalmically, vaginally, rectally, intranasally, orally, or directly to the skin). Formulations for topical administration can include ointments, lotions, creams, gels, drops, suppositories, sprays, liquids and powders. Conventional pharmaceutical carriers, aqueous, powder or oily bases, thickeners and the like can be necessary or desirable. Administration can also be directly into the lung by inhalation of an aerosol or dry micronized powder. Administration can also be by direct injection into the inflamed or degenerating joint space.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates.

The SAGEs and pharmaceutical compositions described herein can be used in a variety of applications related to drug delivery, small molecule delivery, wound healing, treatment of inflammatory skin disorders, treatment of inflammatory dental disorders, treatment of inflammatory respiratory disorders, treatment of inflammatory eye disorders, burn injury healing, and tissue regeneration/engineering. In one aspect, the SAGEs and compositions described herein can improve wound healing in a subject in need of such improvement. The SAGEs and pharmaceutical compositions described herein can be placed directly in or on any biological system without purification as it is composed of biocompatible materials. Examples of sites the SAGEs can be placed include, but are not limited to, soft tissue such as muscle or fat; hard tissue such as bone or cartilage; areas of tissue regeneration; a void space such as periodontal pocket; surgical incision or other formed pocket or cavity; a natural cavity such as the oral, vaginal, rectal or nasal cavities, the joint space, the cul-de-sac of the eye, and the like; the peritoneal cavity and organs contained within, and other sites into or onto which the compounds can be placed including a skin surface defect such as a cut, scrape or burn area. It is contemplated that the tissue can be damaged due to injury or a degenerative condition or, in the alternative, the SAGEs and compositions described herein can be applied to undamaged tissue to prevent injury to the tissue.

In the case of inflammatory skin disorders such as psoriasis, acne, atopic dermatitis, rosacea or UV light dependent photo-aging, the SAGEs can be applied topically as part of an emollient to prevent or treat the intended condition. In the case of respiratory disorders such as asthma, chronic obstructive pulmonary disease, acute lung injury or cystic fibrosis, the SAGEs can be dissolved in a water-soluble isotonic vehicle compatible with airway lining fluid and delivered to the lung or nasal passages as an inhaled aerosol. Alternately, the SAGEs can be formulated into a micronized powder and inhaled into the lung as a dry powder. In the case of eye diseases, the SAGEs can be placed into an aqueous vehicle and applied to the eye topically as drops, or injected directly into the eye either by needle or using an implanted constant drug delivery device. In the case of dental disorders such as periodontal disease, the SAGEs can be added as a component of a mouthwash or formulated into creams or gingival packing materials to be applied directly to the gingival crevice.

The SAGEs can also be injected parenterally, either intravenously, intramuscularly or subcutaneously, to treat or prevent systemic inflammatory disorders such as diabetic vascular or renal disease or inflammatory gastrointestinal diseases. Similarly, the SAGEs can be injected intra-articularly to treat inflammatory and degenerative arthritis. The SAGEs can also be administered orally in capsules or formulated into an enema to be delivered intra-rectally as treatment for inflammatory bowel diseases.

The SAGEs and compositions described herein can deliver at least one pharmaceutically-acceptable compound to a patient in need of such delivery, comprising contacting at least one tissue capable of receiving the pharmaceutically- acceptable compound with one or more compositions described herein. The SAGEs can be used as a carrier for a wide variety of releasable biologically active substances having curative or therapeutic value for human or non-human animals. Many of these substances that can be carried by the SAGE are discussed above. Included among biologically active materials which are suitable for incorporation into the gels of the invention are therapeutic drugs, e.g., anti-inflammatory agents, anti-pyretic agents, steroidal and non-steroidal drugs for anti-inflammatory use, hormones, growth factors, contraceptive agents, antivirals, antibacterials, antifungals, analgesics, hypnotics, sedatives, tranquilizers, anti-convulsants, muscle relaxants, local anesthetics, antispasmodics, antiulcer drugs, peptidic agonists, sympathimometic agents, cardiovascular agents, antitumor agents, oligonucleotides and their analogues and so forth. A biologically active substance is added in pharmaceutically active amounts.

In one aspect, the sulfated and alkylated SAGEs described herein can inhibit the activity of the receptor for Advanced Glycation Endproducts (RAGE), P-selectin, or human leukocyte elastase. RAGE is highly expressed in human skin, where it is present on dermal fibroblasts, dendritic cells, keratinocytes, endothelial cells and monocytes. RAGE is upregulated in sun-exposed skin by Advanced Glycation End-Products (AGE) and by the cytokine tumor necrosis factor-α. RAGE plays a prominent role in UV-induced photo-ageing, where its ligation by AGE products such as UV-induced carboxymethyl lysine (CML) promotes skin aging through stimulation of extracellular matrix production by dermal fibroblasts. The role of RAGE is likely to be even more prominent in psoriasis because this disease is critically dependent on activated T-lymphocytes for initiation of inflammation. T-lymphocytes may also be mechanistically important in acne and atopic dermatitis. In the case of acne, elevated dermal levels of $CD3^+$ and $CD4^+$ T-lymphocytes and macrophages stimulate hyper-proliferation of keratinocytes in the ducts of follicles, producing the plugged follicular ducts that lead to formation of the acne comedone. In the case of atopic dermatitis, dermal antigens activate $T_H2$ lymphocytes which secrete cytokines such as interleukin-4 (IL-4) and interleukin-13 (IL-13), resulting in the recruitment of eosinophils into skin. Eosinophils, in turn, release cationic toxins such as major basic protein, which produces allergic skin disease. Thus, the potent RAGE inhibiting activity of the compounds described herein makes them useful in treating a variety of skin disorders including, but not limited to, acne, eczema, atopic dermatitis, psoriasis, or photo-dermal ageing.

In the adult state, RAGE is not always so entirely helpful to the organism. Malignant tumors secrete amphoterin (or high mobility box group protein-1, HMGB-1) as an autocrine factor and use the interaction of amphoterin with RAGE to promote primary tumor growth and metastasis. Blocking RAGE with a recombinant decoy (soluble RAGE or s-RAGE) reduces tumor growth and inhibits metastasis. During sepsis, monocytes and macrophages secrete amphoterin which interacts with RAGE on blood vessels and other inflammatory cells to enhance the severity of bacterial shock. Blocking this interaction with antibodies against RAGE prevents organ damage in severe sepsis. In the adult state, RAGE also functions as a vascular adhesion receptor promoting the recruitment of PMNs, monocytes and lymphocytes into areas of inflammation. Blocking RAGE blunts inflammatory cell influx. This has been previously demonstrated in animal models of multiple sclerosis, where competitive blockade of vascular endothelial RAGE with s-RAGE prevents the influx of activated encephalitogenic T-lymphocytes into the central nervous system, and retards onset and progression of neurologic inflammation and degeneration.

RAGE also interacts with a family of calcium binding proteins called S100 calgranulins, which are secreted by PMNs, monocytes and lymphocytes as potent inflammation-promoting factors. Elevated levels of S 100 calgranulins are a prominent marker of PMN inflammation in acute lung injury and in the airway secretions of patients with cystic fibrosis. In the eye, the interaction of S 100 calgranulins with RAGE plays a prominent role leading to blindness in age-related macular degeneration. RAGE also binds the Alzheimer's β-amyloid peptide and the βsheets of amyloid proteins. Through RAGE-related induction of neural cell death and inflammation, RAGE-β sheet fibrillar interactions mediate Alzheimer's dementia and organ damage in systemic amyloidosis.

RAGE is also prominent in diabetes mellitus. When blood glucose is elevated, the aldehyde group of glucose randomly attaches to the amines of cellular proteins, covalent adducts. In the presence of oxidants such as hypochlorous acid (HOCl), the oxidant produced by PMNs, this glucose moiety can then become oxidized. These oxidized, glycosylated proteins are known as Advanced Glycation End-Products, (AGE). AGEs also bind the RAGE receptor avidly, and trigger RAGE-mediated signaling. AGE-RAGE signaling accounts for the vascular endothelial dysfunction, poor wound healing and accelerated arterial atherosclerosis characteristic of poorly controlled diabetes. In the eye, AGE-RAGE signaling produces the proliferation of retinal microvessels that leads to diabetic retinopathy and blindness. In the kidney, AGE-RAGE signaling accounts for the initial renal hypertrophy and then fibrosis that causes diabetic renal failure (diabetic nephropathy). AGE-RAGE signaling likewise produces apoptosis of endothelium, inhibits blood vessel growth and retards healing of cutaneous diabetic ulcers. The ability of the SAGEs to block RAGE makes them particularly valuable as therapeutic agents for inflammation. RAGE functions in utero as a receptor binding the growth promoting nuclear protein amphoterin, or high mobility box protein-1. There, the amphoterin-RAGE interaction triggers growth signaling important for nervous system development. In the adult state, RAGE is expressed in the cells of vessel walls, neural tissues, cardiac myocytes, monocytes and macrophages, T-lymphocytes, renal mesangial cells, and in skin fibroblasts, dendrocytes and keratinocytes. Thus, in one aspect, the SAGEs and compositions described herein can be used to safely reduce or prevent inflammation in a subject produced by a variety of different maladies attributed to RAGE-related diseases including, but not limited to, cancer, multiple sclerosis, osteoarthritis, cystic fibrosis, sickle cell anemia, a cardiovascular inflammatory disorder, or a cardiovascular inflammatory disorder, or diabetic complications.

In other aspects, the SAGEs and compositions, as negatively charged entities, can also be administered to bind and inhibit cationic skin peptides derived from cathelicidins, thereby treating or preventing skin disorders. For example, the skin condition known as acne rosacea, which is known to occur from excess skin expression of active cathelicidin peptides, can be treated or prevented using the SAGEs described herein. Examples of skin disorders that can be treated or prevented using the SAGEs include, but are not limited to, rosacea, atopic dermatitis (eczema), allergic contact dermatitis, psoriasis, dermatitis herpetiformis, acne, diabetic skin ulcers and other diabetic wounds, burns (including relieving pain of thermal burns), sunburn (including relieving pain of sunburn), prevention of scarring after plastic surgery, actinic keratoses, inflammation from insect bites, poison ivy, radiation-induced dermatitis/burn, facilitation of skin healing, prevention and treatment of keloid scarring, or the treatment of seborrheic dermatitis.

Due to the ability of the SAGEs to inhibit RAGE activity and other biological mechanisms, the SAGEs have numerous therapeutic applications in addition to treating or preventing skin disorders. In one aspect, the SAGEs can be used in dental and oral surgery to treat gingivitis (periodontal disease) and aphthous ulcers. In other aspects, the SAGEs can be used in opthalmological applications such as, for example, in the treatment of age-related macular degeneration, diabetic retinopathy, dry eye syndrome and other inflammatory conjunctivitis, iritis, uveitis, allergic conjunctivitis, anti-inflammatory aid in cataract surgery, or in the prevention of corneal inflammation and scarring. In further aspects, the SAGEs can be used in genitourinary applications (e.g., prevention of urinary tract infection, treatment of the transitional cell cancer of the bladder and uroepithelial system; treatment of interstitial cystitis; and use as a vaginal lubricant/protective to prevent transmission of sexually transmitted diseases).

In another aspect, the SAGEs can be used to treat a number of respiratory disorders including cystic fibrosis, bronchiectasis, rhinitis (both allergic and perennial), sinusitis, emphysema and chronic bronchitis (COPD), acute lung injury/adult respiratory distress syndrome, interstitial lung fibrosis, SARS, asthma, and respiratory syncytial virus. In other aspects, the SAGEs can prevent and treat snoring and obstructive sleep apnea, prevent infection by common respiratory pathogens (*Streptococcus pneumoniae, Hemophilus influenzae, Staphylococcus, Mycoplasma pneumoniae, Chlamydial pneumonia*, Gram negative enteric infections) in immune suppressed hosts such as subjects who are HIV positive or who have hematopoietic malignancies, or prevent and treat otitis media.

The SAGEs can be used in cardiovascular applications (e.g., treating or preventing acute coronary syndrome or atherosclerosis); hematological/oncological applications (e.g., prevention and treatment of sickle cell anemia; prevention and treatment of metastatic disease; and prevention of hypercoagulable state of malignancy (Trousseau's syndrome)); treatment of infectious diseases (e.g., cerebral vascular occlusive syndromes and nephritis in Falciparum malaria, Yellow fever, Denge fever, systemic sepsis, and adjunctive treatment of HIV to prevent viral fusion with and infection of target cells); treatment of gastrointestinal diseases (e.g., ulcerative colitis, Crohn's disease of the bowel, Hemorrhoids, and the Prevention of stress ulceration of the stomach and esophagus); treatment of rheumatological and immunological diseases (e.g., prevention and treatment of osteoarthritis, rheumatoid arthritis, systemic lupus erythematosis, prevention and treatment of angioneurotic edema, Sjogren's syndrome, systemic sclerosis, systemic amyloidosis, and systemic mastocytosis); renal diseases (e.g., prevention and treatment of diabetic nephropathy and glomerulonephritis); and neurologic diseases (e.g., multiple sclerosis and Alzheimer's dementia). The SAGEs and compositions described herein are safer than other related therapies. For example, heparin and other sulfated polysaccharides can reduce diabetic complications in both animal and clinical studies, and are particularly effective against diabetic nephropathy. However, heparins cannot be used in general clinical settings to prevent diabetic complications because the anticoagulant properties present an excessive risk of bleeding. The SAGEs and compositions described herein possess low anticoagulant activity, which is an important consideration for long-term treatment, which is demonstrated below in the Examples. Additionally, the SAGEs have little to no toxicity, which is also demonstrated in the Examples.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions. Compounds described below are identified by code numbers as defined above and referred to in FIG. 2.

I. Synthesis of Alkylated HA Derivatives

A. Preparation of Methyl HA (DS-2)

Hyaluronic acid (HA, Novozymes Biopolymers, 950 kDa) (2.0 g) was dissolved in 20 mL of NaOH (40% w/v) in a 100 mL beaker and the mixture stirred for 2 h at room temperature (RT). The resulting viscous liquid was transferred to a 400 mL beaker that contained 100 mL of isopropanol, and mixing was continued. To a stirred mixture was added 10 mL of iodomethane, and the mixture was stirred for 24 h at rt. The resulting suspension was filtered to collect the crude methylated HA product. This crude MeHA was dissolved in 250 mL of distilled water, the solution was adjusted to pH ~7.0, and the solution was dialyzed against distilled water for 24 h, changing the external water bath four times during this period. The dialyzed MeHA product was lyophilized to afford 1.25 g of methyl HA as a cottony mesh. $^1$H NMR (D$_2$O, δ): 1.85 (s, 3H, NCH$_3$), 3.20-3.80 (m, 1OH, OCH+OCH$_3$). The substitution degree (SD) was determined by $^1$H NMR, SD=[(integration of methyl HA at δ 3.20-3.8)−(integration of HA at δ 3.20-3.8)]/(integration of NCH$_3$ at 1.85), and was estimated to be SD=2, or an average of 2 methyl groups per disaccharide unit. This suggests that both the primary hydroxyl and at least one secondary hydroxyl group were modified by this process.

B. Preparation of Methyl HA (DS-I)

Hyaluronic acid (HA, Novozymes Biopolymers, 950 kDa) (2.0 g) was dissolved in 20 mL of NaOH (40% w/v) in a 100 mL beaker and the mixture stirred for 2 h at room temperature (rt). The resulting viscous liquid was transferred to a 400 mL beaker that contained 100 mL of isopropanol, and mixing was continued. To stirred mixture was added 4 mL of iodomethane, and the mixture was stirred for 24 h at rt. The resulting suspension was filtered to collect the crude methylated HA product. This crude MeHA was dissolved in 250 mL of distilled water, the solution was adjusted to pH ~7.0, and the solution was dialyzed against distilled water for 24 h, changing the external water bath four times during this period. The dialyzed MeHA product was lyophilized to afford 1.25 g of methyl HA as a cottony mesh. $^1$H NMR (D$_2$O, δ): 1.8 S (s, 3H, NCH$_3$), 3.20-3.80 (m, 1OH, OCH+OCH$_3$). The substitution degree (SD) was determined by $^1$H NMR, SD=[(integration of methyl HA at δ 3.20-3.8)−(integration of HA at δ 3.20-3.8)]/(integration of NCH$_3$ at 1.85), and was estimated to be SD=1, or an average of 1 methyl groups per disaccharide unit. This suggests that the primary hydroxyl and at least one secondary hydroxyl group were modified by this process.

C. Preparation of FHA-2 (DS-1)

To a 25 mL flask containing 1.0 g of 2,2,3,3,4,4-heptafluoro-1-butanol (5 mmol), 1.3 mL of phosphorus tribromide (7.5 mmol) was added slowly. The mixture was stirred at 60° C. for 30 minutes, and then saturated sodium bicarbonate solution (15 mL) was slowly added to quench the reaction. The aqueous solution was extracted with three 15-mL portions of dichloromethane, the organic layer containing the heptafluorobutyl bromide was concentrated, and the residue was used without purification in the next step.

HA (2.0 g) was dissolved in 20 mL of NaOH (40% w/v) in a 100 mL beaker and the mixture stirred for 2 h at room temperature (rt). The resulting viscous liquid was transferred to a 400 mL beaker that contained 100 mL of isopropanol, and mixing was continued. To the stirred mixture was added the crude heptafluorobutyl bromide in 10 mL of isopropanol, and the mixture was stirred for 24 h at rt. The resulting suspension was filtered to collect the crude FHA-2 product. This crude FHA-2 was dissolved in 250 mL of distilled water, the solution was adjusted to pH ~7.0, and the solution was dialyzed against distilled water for 24 h, changing the external water bath four times during this period. The dialyzed FHA-2 product was lyophilized to afford 1.5 g of FHA-2, designed as FHA-2 as cottony mesh. $^1$H NfMR (D$_2$O, δ): 1.82 (s, 3H, NCH$_3$), 3.15-3.80 (m, 8H, 0CH+0CH$_2$). $^{19}$F NMR (D$_2$O, δ): −115.3, −120.8. The substitution degree (SD) was determined by $^1$H NMR as 1.0. SD=[(integration of FHA-2 at δ 3.15-3.80)−(integration of HA at δ 3.20-3.8)]/[(integration of NCH$_3$ at 1.82)×(⅔)].

D. Preparation of FHA-2 (DS-2)

To a 25 mL flask containing 3.0 g of 2,2,3,3,4,4-heptafluoro-1-butanol (15 mmol), 2.5. mL of phosphorus tribromide (16 mmol) was added slowly. The mixture was stirred at 60° C. for 30 minutes, and then saturated sodium bicarbonate solution (15 mL) was slowly added to quench the reaction. The aqueous solution was extracted with three 15-mL portions of dichloromethane, the organic layer containing the heptafluorobutyl bromide was concentrated, and the residue was used without purification in the next step.

HA (2.0 g) was dissolved in 20 mL of NaOH (40% w/v) in a 100 mL beaker and the mixture stirred for 2 h at room temperature (rt). The resulting viscous liquid was transferred to a 400 mL beaker that contained 100 mL of isopropanol, and mixing was continued. To the stirred mixture was added the crude heptafluorobutyl bromide in 10 mL of isopropanol, and the mixture was stirred for 24 h at rt. The resulting suspension was filtered to collect the crude FHA-2 product. This crude FHA-2 was dissolved in 250 mL of distilled water, the solution was adjusted to pH ~7.0, and the solution was dialyzed against distilled water for 24 h, changing the external water bath four times during this period. The dialyzed FHA-2 product was lyophilized to afford 1.5 g of FHA-2, designed as FHA-2 as cottony mesh. H NMR (D$_2$O, δ): 1.82 (s, 3H, NCH$_3$), 3.15-3.80 (m, 8H, OCH+OCH$_2$). $^{19}$F NMR (D$_2$O, δ): −1 15.3, −120.8. The substitution degree (SD) was determined by $^1$H NMR as 2.0. SD=[(integration of FHA-2 at δ 3.15-3.80)−(integration of HA at δ 3.20-3.8)]/[(integration of NCH$_3$ at 1.82)×(⅔)].

E. Preparation of FHA-I (DS-I)

To a 25 mL flask containing 1.0 g of 2,2,3,3,-pentafluoro-1-propanol (5 mmol), 1.3 mL of phosphorus tribromide (7.5 mmol) was added slowly. The mixture was stirred at 60° C. for 30 minutes, and then saturated sodium bicarbonate solution (15 mL) was slowly added to quench the reaction. The aqueous solution was extracted with three 15-mL portions of dichloromethane, the organic layer containing the heptafluorobutyl bromide was concentrated, and the residue was used without purification in the next step.

HA (2.0 g) was dissolved in 20 mL of NaOH (40% w/v) in a 100 mL beaker and the mixture stirred for 2 h at room temperature (rt). The resulting viscous liquid was transferred to a 400 mL beaker that contained 100 mL of isopropanol, and mixing was continued. To the stirred mixture was added the crude heptafluorobutyl bromide in 10 mL of isopropanol, and the mixture was stirred for 24 h at rt. The resulting suspension was filtered to collect the crude FHA-I product. This crude FHA-I was dissolved in 250 mL of distilled water, the solution was adjusted to pH ~7.0, and the solution was dialyzed against distilled water for 24 h, changing the external water bath four times during this period. The dialyzed FHA-I product was lyophilized to afford 1.5 g of FHA-I, designed as FHA-I as cottony mesh. H NMR ($D_2O$, δ): 1.80 (s, 3H, $NCH_3$), 3.15-3.80 (m, 8H, $OCH+OCH_2$). $^{19}F$ NMR ($D_2O$, δ): −113.6, −118.0. The substitution degree (SD) was determined by $^1H$ NMR as 1.0. SD=[(integration of FHA-I at δ 3.15-3.80)−(integration of HA at δ 3.20-3.8)]/[(integration of $NCH_3$ at 1.80)×(⅔)].

F. Preparation of FHA-I (DS-2)

To a 25 mL flask containing 3.0 g of 2,2,3,3,-pentafluoro-1-propanol (15 mmol), 3 mL of phosphorus tribromide (18 mmol) was added slowly. The mixture was stirred at 60 C for 30 minutes, and then saturated sodium bicarbonate solution (15 mL) was slowly added to quench the reaction. The aqueous solution was extracted with three 15-mL portions of dichloromethane, the organic layer containing the heptafluorobutyl bromide was concentrated, and the residue was used without purification in the next step.

HA (2.0 g) was dissolved in 20 mL of NaOH (40% w/v) in a 100 mL beaker and the mixture stirred for 2 h at room temperature (it). The resulting viscous liquid was transferred to a 400 mL beaker that contained 100 mL of isopropanol, and mixing was continued. To the stirred mixture was added the crude heptafluorobutyl bromide in 10 mL of isopropanol, and the mixture was stirred for 24 h at it. The resulting suspension was filtered to collect the crude FHA-I product. This crude FHA-I was dissolved in 250 mL of distilled water, the solution was adjusted to pH ~7.0, and the solution was dialyzed against distilled water for 24 h, changing the external water bath four times during this period. The dialyzed FHA-I product was lyophilized to afford 1.5 g of FHA-I, designed as FHA-I as cottony mesh. H NMR ($D_2O$, δ): 1.80 (s, 3H, $NCH_3$), 3.15-3.80 (m, 8H, $OCH+OCH_2$). $^{19}F$ NMR ($D_2O$, δ): −113.6, −118.0. The substitution degree (SD) was determined by $^1H$ NMR as 2.0. SD=[(integration of FHA-I at δ 3.15-3.80)−(integration of HA at δ 3.20-3.8)]/[(integration Of $NCH_3$ at 1.80)×(⅔)].

G. Preparation of BGHA

Hyaluronic acid (HA, Novozymes Biopolymers, 950 kDa) (2.0 g) was dissolved in 20 mL of NaOH (40% w/v) in a 100 mL beaker and the mixture stirred for 2 h at room temperature (rt). The resulting viscous liquid was transferred to a 400 mL beaker that contained 100 mL of isopropanol, and mixing was continued. To stirred mixture was added 10 mL of Benzyl Glycidyl Ether, and the mixture was stirred for 24 h at it. The resulting suspension was filtered to collect the crude BGHA product. This crude BGHA was dissolved in 250 mL of distilled water, the solution was adjusted to pH ~7.0, and the solution was dialyzed against distilled water for 24 h, changing the external water bath four times during this period. The dialyzed BGHA product was lyophilized to afford 1.25 g of BGHA as a cottony mesh. $^1H$ NMR ($D_2O$, δ): 1.85 (s, 3H, $NCH_3$), 3.20-3.80 (m, 1OH, OCHH—$OCH_3$). The substitution degree (SD) was determined by $^1H$ NMR, SD is less than 1.

H. Preparation of Low Molecular Weight Methyl HA (DS-2)

Hyaluronic acid (HA, Novozymes Biopolymers, 53 kDa) (2.0 g) was dissolved in 20 mL of NaOH (40% w/v) in a 100 mL beaker and the mixture stirred for 2 h at room temperature (it). The resulting viscous liquid was transferred to a 400 mL beaker that contained 100 mL of isopropanol, and mixing was continued. To stirred mixture was added 10 mL of iodomethane, and the mixture was stirred for 24 h at rt. The resulting suspension was filtered to collect the crude Low molecule methylated HA product. This crude LMW MeHA was dissolved in 250 mL of distilled water, the solution was adjusted to pH ~7.0, and the solution was dialyzed against distilled water for 24 h, changing the external water bath four times during this period. The dialyzed LMW MeHA product was lyophilized to afford 1.2 g of methyl HA as a cottony mesh. $^1H$ NMR ($D_2O$, δ): 1.85 (s, 3H, $NCH_3$), 3.20-3.80 (m, 1OH, $OCH+OCH_3$). The substitution degree (SD) was determined by $^1H$ NMR, as 2.

I. Preparation of Low Molecular Weight Methyl HA (DS-I)

Hyaluronic acid (HA, Novozymes Biopolymers, 53 kDa) (2.0 g) was dissolved in 20 mL of NaOH (40% w/v) in a 100 mL beaker and the mixture stirred for 2 h at room temperature (rt). The resulting viscous liquid was transferred to a 400 mL beaker that contained 100 mL of isopropanol, and mixing was continued. To stirred mixture was added 4 mL of iodomethane, and the mixture was stirred for 24 h at it. The resulting suspension was filtered to collect the crude low molecule methylated HA product. This crude LMW MeHA was dissolved in 250 mL of distilled water, the solution was adjusted to pH ~7.0, and the solution was dialyzed against distilled water for 24 h, changing the external water bath four times during this period. The dialyzed LMW MeHA product was lyophilized to afford 1.2 g of LMW MeHA as a cottony mesh. $^1H$ NMR ($D_2O$, δ): 1.85 (s, 3H, $NCH_3$), 3.20-3.80 (m, 1OH, $OCH+OCH_3$). The substitution degree (SD) was determined by $^1H$ NMR as 1.

J. Preparation of Low Molecular Weight FHA-2 (DS-1)

To a 25 mL flask containing 1.0 g of 2,2,3,3,4,4-heptafluoro-1-butanol (5 mmol), 1.3 mL of phosphorus tribromide (7.5 mmol) was added slowly. The mixture was stirred at 60° C. for 30 minutes, and then saturated sodium bicarbonate solution (15 mL) was slowly added to quench the reaction. The aqueous solution was extracted with three 15-mL portions of dichloromethane, the organic layer containing the heptafluorobutyl bromide was concentrated, and the residue was used without purification in the next step.

HA (2.0 g, 53 kDa was dissolved in 20 mL of NaOH (40% w/v) in a 100 mL beaker and the mixture stirred for 2 h at room temperature (rt). The resulting viscous liquid was transferred to a 400 mL beaker that contained 100 mL of isopropanol, and mixing was continued. To the stirred mixture was added the crude heptafluorobutyl bromide in 10 mL of isopropanol, and the mixture was stirred for 24 h at rt. The resulting suspension was filtered to collect the crude LMW FHA-2 product. This crude LMW FHA-2 was dissolved in 250 mL of distilled water, the solution was adjusted to pH ~7.0, and the solution was dialyzed against distilled water for 24 h, changing the external water bath four times during this period. The dialyzed LMW FHA-2 product was lyophilized to afford 1.5 g of LMW FHA-2, designed as LMW FHA-2 as cottony mesh. $^1$H NMR (D$_2$O, δ): 1.82 (s, 3H, NCH$_3$), 3.15-3.80 (m, 8H, OCH+OCHz). $^{19}$F NMR (D$_2$O, δ): −115.3, −120.8. The substitution degree (SD) was determined by $^1$H NMR as 1.0.

K. Preparation of Low Molecular Weight FHA-2 (DS-2)

To a 25 mL flask containing 3.0 g of 2,2,3,3,4,4-heptafluoro-l-butanol (15 mmol), 2.5. mL of phosphorus tribromide (16 mmol) was added slowly. The mixture was stirred at 60° C. for 30 minutes, and then saturated sodium bicarbonate solution (15 mL) was slowly added to quench the reaction. The aqueous solution was extracted with three 15-mL portions of dichloromethane, the organic layer containing the heptafluorobutyl bromide was concentrated, and the residue was used without purification in the next step. HA (2.0 g, 53 kDa) was dissolved in 20 mL of NaOH (40% w/v) in a 100 mL beaker and the mixture stirred for 2 h at room temperature (rt). The resulting viscous liquid was transferred to a 400 mL beaker that contained 100 mL of isopropanol, and mixing was continued. To the stirred mixture was added the crude heptafluorobutyl bromide in 10 mL of isopropanol, and the mixture was stirred for 24 h at rt. The resulting suspension was filtered to collect the crude LMW FHA-2 product. This crude LMW FHA-2 was dissolved in 250 mL of distilled water, the solution was adjusted to pH ~7.0, and the solution was dialyzed against distilled water for 24 h, changing the external water bath four times during this period. The dialyzed LMW FHA-2 product was lyophilized to afford 1.5 g of LMW FHA-2, designed as LMW FHA-2 as cottony mesh. H NMR (D$_2$O, δ): 1.82 (s, 3H, NCH$_3$), 3.15-3.80 (m, 8H, 0CH+0CH$_2$). $^{19}$F NMR (D$_2$O, δ): −115.3, −120.8. The substitution degree (SD) was determined by $^1$H NMR as 2.0.

L. Preparation of Low Molecular Weight FHA-I (DS-I)

To a 25 mL flask containing 1.0 g of 2,2,3,3,-pentafluoro-l-propanol (5 mmol), 1.3 mL of phosphorus tribromide (7.5 mmol) was added slowly. The mixture was stirred at 60° C. for 30 minutes, and then saturated sodium bicarbonate solution (15 mL) was slowly added to quench the reaction. The aqueous solution was extracted with three 15-mL portions of dichloromethane, the organic layer containing the heptafluorobutyl bromide was concentrated, and the residue was used without purification in the next step.

HA (2.0 g, 53 kDa) was dissolved in 20 mL of NaOH (40% w/v) in a 100 mL beaker and the mixture stirred for 2 h at room temperature (rt). The resulting viscous liquid was transferred to a 400 mL beaker that contained 100 mL of isopropanol, and mixing was continued. To the stirred mixture was added the crude heptafluorobutyl bromide in 10 mL of isopropanol, and the mixture was stirred for 24 h at rt. The resulting suspension was filtered to collect the crude LMW FHA-I product. This crude LMW FHA-I was dissolved in 250 mL of distilled water, the solution was adjusted to pH ~7.0, and the solution was dialyzed against distilled water for 24 h, changing the external water bath four times during this period. The dialyzed LMW FHA-I product was lyophilized to afford 1.5 g of LMW FHA-I, designed as LMW FHA-I as cottony mesh. H NMR (D$_2$O, δ): 1.80 (s, 3H, NCH$_3$), 3.15-3.80 (m, 8H, OCH+OCH$_2$). $^{19}$F NMR (D$_2$O, δ): −113.6, −118.0. The substitution degree (SD) was determined by $^1$H NMR as 1.0.

M. Preparation of LMW FHA-I (DS-2)

To a 25 mL flask containing 3.0 g of 2,2,3,3,-pentafluoro-l-propanol (15 mmol), 3 mL of phosphorus tribromide (18 mmol) was added slowly. The mixture was stirred at 60° C. for 30 minutes, and then saturated sodium bicarbonate solution (15 mL) was slowly added to quench the reaction. The aqueous solution was extracted with three 15-mL portions of dichloromethane, the organic layer containing the heptafluorobutyl bromide was concentrated, and the residue was used without purification in the next step.

HA (2.0 g, 53 kDa) was dissolved in 20 mL of NaOH (40% w/v) in a 100 mL beaker and the mixture stirred for 2 h at room temperature (rt). The resulting viscous liquid was transferred to a 400 mL beaker that contained 100 mL of isopropanol, and mixing was continued. To the stirred mixture was added the crude heptaflubrobutyl bromide in 10 mL of isopropanol, and the mixture was stirred for 24 h at rt. The resulting suspension was filtered to collect the crude LMW FHA-I product. This crude LMW FHA-I was dissolved in 250 mL of distilled water, the solution was adjusted to pH ~7.0, and the solution was dialyzed against distilled water for 24 h, changing the external water bath four times during this period. The dialyzed LMW FHA-I product was lyophilized to afford 1.5 g of LMW FHA-I, designed as LMW FHA-I as cottony mesh. $^1$H NMR (D$_2$O, δ): 1.80 (s, 3H, NCH$_3$), 3.15-3.80 (m, 8H, OCH+OCH$_2$). $^{19}$F NMR (D$_2$O, δ): −1 13.6, −118.0. The substitution degree (SD) was determined by $^1$H NMR as 2.0.

N. Preparation of Low Molecular Weight BGHA

Hyaluronic acid (HA, Novozymes Biopolymers, 53 kDa) (2.0 g) was dissolved in 20 mL of NaOH (40% w/v) in a 100 mL beaker and the mixture stirred for 2 h at room temperature (rt). The resulting viscous liquid was transferred to a 400 mL beaker that contained 100 mL of isopropanol, and mixing was continued. To a stirred mixture was added 10 mL of Benzyl Glycidyl Ether, and the mixture was stirred for 24 h at rt. The resulting suspension was filtered to collect the crude LMW BGHA product. This crude LMW BGHA was dissolved in 250 mL of distilled water, the solution was adjusted to pH ~7.0, and the solution was dialyzed against distilled water for 24 h, changing the external water bath four times during this period. The dialyzed LMW BGHA product was lyophilized to afford 1.25 g of LMW BGHA as a cottony mesh. $^1$H NMR (D$_2$O, δ): 1.85 (s, 3H, NCH$_3$), 3.20-3.80 (m, 1OH, OCH+OCH$_3$). The substitution degree (SD) was determined by $^1$H NMR, SD is less than 1.

II. Sulfation of Alkylated HA Derivatives

1. Preparation of LMW-P-OSFHA-I (DS-I) (GM-211101)

First, the tributylammonium (TBA) salt of LMW FHA-I (DS-I) was prepared by the addition of 1 mL of tributylamine to LMW FHA-I (1.0 g) in 100 mL of deionized water which was adjusted to pH 3.0 with IN HCl. The mixture was mixed vigorously, dried by lyophilization. The resulting salt (FHA-I-TBA) was dissolved in 25 mL of DMF to which the required excess (6 mol/equiv of available hydroxy group in HA) of pyridine-sulfur trioxide complex (0.4 g) was added. After stirring for 3 h at 40° C., the reaction was quenched by addition of 50 mL of water, and the crude material was precipitated by adding 75 mL of cold ethanol saturated with anhydrous sodium acetate, and then collected by filtration. The resulting crude partially O-sulfated HA was dissolved in distilled water and dialyzed against 100 mM of NaCl solution for two days, changing the solution four times a day, and lyophilized to give the product (330 mg) in 75% yield and characterized by $^1$H NMR, sulfation SD=1.0. The substitution degree is determined by comparing the NMR shift of OCH to those in literature (Carbohydrate Research, 1998, 306, 35-43).

2. Preparation of LMW-P-OSFHA-2 (DS I) (GM-311101)

The TBA salt of LMW FHA-2 (FHA-2 from MW 53 kDa HA) was prepared by adding 0.5 mL of tributylamine to the FHA-2 (0.25 g) in 50 mL of distilled water and processing as above in 1. The resulting salt (LMW FHA-2-TBA) was dissolved in 25 mL of DMF to which the required excess (6 mol/equiv of available hydroxy group in HA) of pyridine-sulfur trioxide complex (0.4 g) was added. After stirring for 3 h at 40° C., the reaction was quenched by addition of 50 mL of water, and the crude material was precipitated by adding 75 mL of cold ethanol saturated with anhydrous sodium acetate, and then collected by filtration. The resulting crude partially O-sulfated LMW FHA-2 was dissolved in water, dialyzed, and lyophilized as in 1. to give the product (300 mg) in 68% yield and characterized by $^1$H NMR, sulfation SD=1.0.

3. Preparation of LMW-P-OSMeHA (DS-I) (GM-111101)

The TBA salt of LMW MeHA (DS-I) (from MW 53 kDa HA) was prepared from 0.5 mL of TBA and LMW MeHA (0.5 g) in 50 mL of distilled water as in 1. The resulting salt (LMW MeHA-TBA) was dissolved in 50 mL of DMF to which the required excess (6 mol/equiv of available hydroxy groups in MeHA) of pyridine-sulfur trioxide complex (0.8 g) was added. After stirring for 3 h at 400 C, the reaction was quenched by adding 100 mL of water, and crude material was precipitated by adding 150 mL of cold ethanol saturated with anhydrous sodium acetate, and then collected by filtration. The resulting crude partially O-sulfated MeHA was dissolved in water, dialyzed, and lyophilized as in 1 to give the product (540 mg) in 62% yield, which was shown by 1H NMR to have a sulfation SD=1.0-1.5.

4. Preparation of LMW-P-OSFHA-I (DS-2) (GM-211201)

The TBA salt of LMW FHA-I (FHA-I from MW 53 kDa HA) was prepared by adding 0.5 mL of tributylamine to the FHA-1 (0.25 g) in 50 mL of distilled water and processing as above in 1. The resulting salt (FHA-I-TBA) was dissolved in 25 mL of DMF to which the required excess (6 mol/equiv of available hydroxy group in HA) of pyridine-sulfur trioxide complex (0.4 g) was added. After stirring for 3 h at 40° C., the reaction was quenched by addition of 50 mL of water, and the crude material was precipitated by adding 75 mL of cold ethanol saturated with anhydrous sodium acetate, and then collected by filtration. The resulting crude partially O-sulfated HA was dissolved in distilled water and dialyzed against 100 mM of NaCl solution for two days, changing the solution four times a day, and lyophilized to give the product (300 mg) in 70% yield and characterized by 1H NMR, sulfation SD=1.0.

5. Preparation of LMW-P-OSFHA-2 (DS-2) (GM-311201)

The TBA salt of LMW FHA-2 (FHA-2 from MW 53 kDa HA) was prepared by adding 0.5 mL of tributylamine to the FHA-2 (0.25 g) in 50 mL of distilled water and processing as above in 1. The resulting salt (LMW FHA-2-TBA) was dissolved in 25 mL of DMF to which the required excess (6 mol/equiv of available hydroxy group in HA) of pyridine-sulfur trioxide complex (0.4 g) was added. After stirring for 3 h at 400 C, the reaction was quenched by addition of 50 mL of water, and the crude material was precipitated by adding 75 mL of cold ethanol saturated with anhydrous sodium acetate, and then collected by filtration. The resulting crude partially O-sulfated LMW FHA-2 was dissolved in water, dialyzed, and lyophilized as in 1. to give the product (310 mg) in 70% yield and characterized by 1H NMR, sulfation SD=1.0.

6. Preparation of LMW-P-OSMeHA (DS-2) (GM-111201)

The TBA salt of LMW MeHA (DS-I) (from MW 53 kDa HA) was prepared from 0.5 mL of TBA and LMW MeHA (0.5 g) in 50 mL of distilled water as in 1. The resulting salt (LMW MeHA-TBA) was dissolved in 50 mL of DMF to which the required excess (6 mol/equiv of available hydroxy groups in MeHA) of pyridine-sulfur trioxide complex (0.8 g) was added. After stirring for 3 h at 400 C, the reaction was quenched by adding 100 mL of water, and crude material was precipitated by adding 150 mL of cold ethanol saturated with anhydrous sodium acetate, and then collected by filtration.

The resulting crude partially (^-sulfated MeHA was dissolved in water, dialyzed, and lyophilized as in 1 to give the product (560 mg) in 64% yield, which was shown by 1H NMR to have a sulfation SD=1.0-1.5.

7. Preparation of P-OSFHA I (DS-I) (GM-231101)

The TBA salt of FHA-1 (FHA-1 from MW 950 kDa HA) was prepared by adding 0.5 mL of tributylamine to the FHA-1 (0.25 g) in 50 mL of distilled water and processing as above in 1. The resulting salt (FHA-I-TBA) was dissolved in 25 mL of DMF to which the required excess (6 mol/equiv of available hydroxy group in HA) of pyridine-sulfur trioxide complex (0.4 g) was added. After stirring for 3 h at 400 C, the reaction was quenched by addition of 50 mL of water, and the crude material was precipitated by adding 75 mL of cold ethanol saturated with anhydrous sodium acetate, and then collected by filtration. The resulting crude partially O-sulfated HA was dissolved in distilled water and dialyzed against 100 mM of NaCl solution for two days, changing the solution four times a day, and lyophilized to give the product (300 mg) in 68% yield and characterized by 1H NMR, sulfation SD=1.0-1.5.

8. Preparation of P-OSFHA-2 (DS-I) (GM-331101)

The TBA salt of FHA-2 (FHA-2 from MW 950 kDa HA) was prepared by adding 0.5 mL of tributylamine to the FHA-2 (0.25 g) in 50 mL of distilled water and processing as above in 1. The resulting salt (FHA-2-TBA) was dissolved in 25 mL of DMF to which the required excess (6 mol/equiv of available hydroxy group in HA) of pyridine-sulfur trioxide complex (0.4 g) was added. After stirring for 3 h at 400 C, the reaction was quenched by addition of 50 mL of water, and the crude material was precipitated by adding 75 mL of cold ethanol saturated with anhydrous sodium acetate, and then collected by filtration. The resulting crude partially O-sulfated FHA-2 was dissolved in water, dialyzed, and lyophilized as in 1. to give the product (320 mg) in 70% yield and characterized by 1H NMR, sulfation SD=1.0-1.5.

9. Preparation of P-OSMeHA (DS-I) (GM-131101)

The TBA salt of MeHA (DS-I) (from MW 950 kDa HA) was prepared from 0.5 mL of TBA and MeHA (0.5 g) in 50 mL of distilled water as in 1. The resulting salt (MeHA-TBA) was dissolved in 50 mL of DMF to which the required excess (6 mol/equiv of available hydroxy groups in MeHA) of pyridine-sulfur trioxide complex (0.8 g) was added. After stirring for 3 h at 40° C., the reaction was quenched by addition of 100 mL of water, and crude material was precipitated by adding 150 mL of cold ethanol saturated with anhydrous sodium acetate, and then collected by filtration. The resulting crude partially Osulfated MeHA was dissolved in water, dialyzed, and lyophilized as in 1 to give the product (510 mg) in 60% yield, which was shown by 1H NMR to have a sulfation SD=1.0-1.5.

10. Preparation of P-OSFHA-I (DS-2) (GM-231201)

TBA salt of FHA-I (FHA-I from MW 950 kDa HA) was prepared by adding 0.5 mL of tributylamine to the FHA-I (0.25 g) in 50 mL of distilled water and processing as above in 1. The resulting salt (FHA-I-TBA) was dissolved in 25 mL of DMF to which the required excess (6 mol/equiv of available hydroxy group in HA) of pyridine-sulfur trioxide complex (0.4 g) was added. After stirring for 3 h at 40° C., the reaction was quenched by addition of 50 mL of water, and the crude material was precipitated by adding 75 mL of cold ethanol saturated with anhydrous sodium acetate, and then collected by filtration. The resulting crude partially O-sulfated HA was dissolved in distilled water and dialyzed against 100 mM of NaCl solution for two days, changing the solution four times a day, and lyophilized to give the product (280 mg) in 68% yield and characterized by 1H NMR, sulfation SD=1.0-1.5.

11. Preparation of P-OSFHA-2 (DS-2) (GM-331201)

The TBA salt of FHA-2 (FHA-2 from MW 950 kDa HA) was prepared by adding 0.5 mL of tributylamine to the FHA-2 (0.25 g) in 50 mL of distilled water and processing as above in 1. The resulting salt (FHA-2-TBA) was dissolved in 25 mL of DMF to which the required excess (6 mol/equiv of available hydroxy group in HA) of pyridine-sulfur trioxide complex (0.4 g) was added. After stirring for 3 h at 400 C, the reaction was quenched by addition of 50 mL of water, and the crude material was precipitated by adding 75 mL of cold ethanol saturated with anhydrous sodium acetate, and then collected by filtration. The resulting crude partially O-sulfated FHA-2 was dissolved in water, dialyzed, and lyophilized as in 1. to give the product (300 mg) in 69% yield and characterized by 1H NMR, sulfation SD=1.0-1.5.

12. Preparation of P-OSMeHA (DS-2) (GM-131201)

The TBA salt of MeHA (DS-I) (from MW 950 kDa HA) was prepared from 0.5 mL of TBA and MeHA (0.5 g) in 50 mL of distilled water as in 1. The resulting salt (MeHA-TBA) was dissolved in 50 mL of DMF to which the required excess (6 mol/equiv of available hydroxy groups in MeHA) of pyridine-sulfur trioxide complex (0.8 g) was added. After stirring for 3 h at 400 C, the reaction was quenched by adding 100 mL of water, and crude material was precipitated by adding 150 mL of cold ethanol saturated with anhydrous sodium acetate, and then collected by filtration. The resulting crude partially 0-sulfated MeHA was dissolved in water, dialyzed, and lyophilized as in 1 to give the product (560 mg) in 64% yield, which was shown by 1H NMR to have a sulfation SD=1.0-1.5.

13. Preparation of LMW-F-OSFHA-I (DS-I) (GM-212101)

The TBA salt of LMW FHA-I (FHA-I from MW 53 kDa HA) was prepared by adding 0.5 mL of tributylamine to the FHA-I (0.25 g) in 50 mL of distilled water and processing as above in 1. The resulting salt (FHA-I-TBA) was dissolved in 25 mL of DMF to which the required excess (12 mol/equiv of available hydroxy group in HA) of pyridine-sulfur trioxide complex (0.8 g) was added. After stirring for 3 h at 40° C., the reaction was quenched by addition of 50 mL of water, and the crude material was precipitated by adding 75 mL of cold ethanol saturated with anhydrous sodium acetate, and then collected by filtration. The resulting crude partially O-sulfated HA was dissolved in distilled water and dialyzed against 100 mM of NaCl solution for two days, changing the solution four times a day, and lyophilized to give the product (300 mg) in 71% yield and characterized by 1H NMR, sulfation SD=1.5-2.0.

14. Preparation of LMW-F-OSFHA-2 (DS-I) (GM-312101)

The TBA salt of LMW FHA-2 (FHA-2 from MW 53 kDa HA) was prepared by adding 0.5 mL of tributylamine to the FHA-2 (0.25 g) in 50 mL of distilled water and processing as above in 1. The resulting salt (LMW FHA-2-TBA) was dissolved in 25 mL of DMF to which the required excess (12 mol/equiv of available hydroxy group in HA) of pyridine-sulfur trioxide complex (0.8 g) was added. After stirring for 3 h at 400 C, the reaction was quenched by addition of 50 mL of water, and the crude material was precipitated by adding 75 mL of cold ethanol saturated with anhydrous sodium acetate, and then collected by filtration. The resulting crude partially O-•sulfated LMW FHA-2 was dissolved in water, dialyzed, and lyophilized as in 1. to give the product (260 mg) in 65% yield and characterized by 1H NMR, sulfation SD=1.5-2.0.

15. Preparation of LMW-F-OSMeHA (DS-I) (GM-112101)

The TBA salt of LMW MeHA (DS-I) (from MW 53 kDa HA) was prepared from 0.5 mL of TBA and LMW MeHA (0.5 g) in 50 mL of distilled water as in 1. The resulting salt (LMW MeHA-TBA) was dissolved in 50 mL of DMF to which the required excess (12 mol/equiv of available hydroxy groups in MeHA) of pyridine-sulfur trioxide complex (1.8 g) was added. After stirring for 3 h at 40° C., the reaction was quenched by adding 100 mL of water, and crude material was precipitated by adding 150 mL of cold ethanol saturated with anhydrous sodium acetate, and then collected by filtration. The resulting crude partially O-sulfated MeHA was dissolved in water, dialyzed, and lyophilized as in 1 to give the product (480 mg) in 60% yield, which was shown by 1H NMR to have a sulfation SD=1.5-2.0.

16. Preparation of LMW-F-OSFHA-I (DS-2) (GM-212201)

The TBA salt of LMW FHA-I (FHA-I from MW 53 kDa HA) was prepared by adding 0.5 mL of tributylamine to the FHA-I (0.25 g) in 50 mL of distilled water and processing as above in 1. The resulting salt (FHA-I-TBA) was dissolved in 25 mL of DMF to which the required excess (12 mol/equiv of available hydroxy group in HA) of pyridine-sulfur trioxide complex (0.8 g) was added. After stirring for 3 h at 40° C., the reaction was quenched by addition of 50 mL of water, and the crude material was precipitated by adding 75 mL of cold ethanol saturated with anhydrous sodium acetate, and then collected by filtration. The resulting crude partially O-sulfated HA was dissolved in distilled water and dialyzed against 100 mM of NaCl solution for two days, changing the solution four times a day, and lyophilized to give the product (300 mg) in 70% yield and characterized by 1H NMR, sulfation SD=1.5-2.0.

17. Preparation of LMW-F-OSFHA-2 (DS-2) (GM-312201)

The TBA salt of LMW FHA-2 (FHA-2 from MW 53 kDa HA) was prepared by adding 0.5 mL of tributylamine to the FHA-2 (0.25 g) in 50 mL of distilled water and processing as above in 1. The resulting salt (LMW FHA-2-TBA) was dissolved in 25 mL of DMF to which the required excess (12 mol/equiv of available hydroxy group in HA) of pyridine-sulfur trioxide complex (0.8 g) was added. After stirring for 3 h at 40° C., the reaction was quenched by addition of 50 mL of water, and the crude material was precipitated by adding 75 mL of cold ethanol saturated with anhydrous sodium acetate, and then collected by filtration. The resulting crude partially O-sulfated LMW FHA-2 was dissolved in water, dialyzed, and lyophilized as in 1. to give the product (300 mg) in 68% yield and characterized by 1H NMR, sulfation SD=1.5-2.0.

18. Preparation of LMW-F-OSMeHA (DS-2) (GM-112201)

The TBA salt of LMW MeHA (DS-I) (from MW 53 kDa HA) was prepared from 0.5 mL of TBA and LMW MeHA (0.5 g) in 50 mL of distilled water as in 1. The resulting salt (LMW MeHA-TBA) was dissolved in 50 mL of DMF to which the required excess (12 mol/equiv of available hydroxy groups in MeHA) of pyridine-sulfur trioxide complex (1.6 g) was added. After stirring for 3 h at 40° C., the reaction was quenched by adding 100 mL of water, and crude material was precipitated by adding 150 mL of cold ethanol saturated with anhydrous sodium acetate, and then collected by filtration. The resulting crude partially 0-sulfated MeHA was dissolved in water, dialyzed, and lyophilized as in 1 to give the product (550 mg) in 63% yield, which was shown by 1H NMR to have a sulfation SD=1.5.

19. Preparation of F-OSFHA-I (DS I) (GM-232101)

The TBA salt of FHA-I (FHA-I from MW 950 kDa HA) was prepared by adding 0.5 mL of tributylamine to the FHA-I (0.25 g) in 50 mL of distilled water and processing as above in 1The resulting salt (FHA-I-TBA) was dissolved in 25 mL of DMF to which the required excess (12 mol/equiv of available hydroxy group in HA) of pyridine-sulfur trioxide complex (0.8 g) was added. After stirring for 3 h at 400 C, the reaction was quenched by addition of 50 mL of water, and the crude material was precipitated by adding 75 mL of cold ethanol saturated with anhydrous sodium acetate, and then collected by filtration. The resulting crude partially O-sulfated HA was dissolved in distilled water and dialyzed against 100 mM of NaCl solution for two days, changing the solution four times a day, and lyophilized to give the product (300 mg) in 68% yield and characterized by 1H NMR, sulfation SD=1.5.

20. Preparation of F-OSFHA-2 (DS-I) (GM-332101)

The TBA salt of FHA-2 (FHA-2 from MW 950 kDa HA) was prepared by adding 0.5 mL of tributylamine to the FHA-2 (0.25 g) in 50 mL of distilled water and processing as above in 1. The resulting salt (FHA-2-TBA) was dissolved in 25 mL of DMF to which the required excess (12 mol/equiv of available hydroxy group in HA) of pyridine-sulfur trioxide complex (0.8 g) was added. After stirring for 3 h at 400 C, the reaction was quenched by addition of 50 mL of water, and the crude material was precipitated by adding 75 mL of cold ethanol saturated with anhydrous sodium acetate, and then collected by filtration. The resulting crude partially O-sulfated FHA-2 was dissolved in water, dialyzed, and lyophilized as in 1. to give the product (310 mg) in 70% yield and characterized by 1H NMR, sulfation SD=1.5-2.0.

21. Preparation of F-OSMeHA (DS-I) (GM-132101)

The TBA salt of MeHA (DS-I) (from MW 950 kDa HA) was prepared from 0.5 mL of TBA and MeHA (0.5 g) in 50 mL of distilled water as in 1. The resulting salt (MeHA-TBA) was dissolved in 50 mL of DMF to which the required excess (12 mol/equiv of available hydroxy groups in MeHA) of pyridine-sulfur trioxide complex (1.6 g) was added. After stirring for 3 h at 400 C, the reaction was quenched by adding 100 mL of water, and crude material was precipitated by adding 150 mL of cold ethanol saturated with anhydrous sodium acetate, and then collected by filtration. The resulting crude partially O-sulfated MeHA was dissolved in water, dialyzed, and lyophilized as in 1 to give the product (500 mg) in 60% yield, which was shown by 1H NMR to have a sulfation SD=1.5-2.0.

22. Preparation of F-OSFHA-I (DS-2) (GM-232201)

The TBA salt of FHA-I (FHA-I from MW 950 kDa HA) was prepared by adding 0.5 mL of tributylamine to the FHA-I (0.25 g) in 50 mL of distilled water and processing as above in 1. The resulting salt (FHA-I-TBA) was dissolved in 25 mL of DMF to which the required excess (12 mol/equiv of available hydroxy group in HA) of pyridine-sulfur trioxide complex (0.8 g) was added. After stirring for 3 h at 400 C, the reaction was quenched by addition of 50 mL of water, and the crude material was precipitated by adding 75 mL of cold ethanol saturated with anhydrous sodium acetate, and then collected by filtration. The resulting crude partially O-sulfated HA was dissolved in distilled water and dialyzed against 100 mM of NaCl solution for two days, changing the solution four times a day, and lyophilized to give the product (300 mg) in 69% yield and characterized by 1H NMR, sulfation SD=1.5-2.0.

23. Preparation of F-OSFHA-2 (DS-2) (GM-332201)

The TBA salt of FHA-2 (FHA-2 from MW 950 kDa HA) was prepared by adding 0.5 mL of tributylamine to the FHA-2 (0.25 g) in 50 mL of distilled water and processing as above in 1. The resulting salt (FHA-2-TBA) was dissolved in 25 mL of DMF to which the required excess (12 mol/equiv of available hydroxy group in HA) of pyridine-sulfur trioxide complex (0.8 g) was added. After stirring for 3 h at 400 C, the reaction was quenched by addition of 50 mL of water, and the crude material was precipitated by adding 75 mL of cold ethanol saturated with anhydrous sodium acetate, and then collected by filtration. The resulting crude partially O-sulfated FHA-2 was dissolved in water, dialyzed, and lyophilized as in 1. to give the product (300 mg) in 69% yield and characterized by 1H NMR, sulfation SD=1.5-2.0.

24. Preparation of F-OSMeHA (DS-2) (GM-132201)

The TBA salt of MeHA (DS-I) (from MW 950 kDa HA) was prepared from 0.5 mL of TBA and MeHA (0.5 g) in 50 mL of distilled water as in 1. The resulting salt (MeHA-TBA) was dissolved in 50 mL of DMF to which the required excess (12 mol/equiv of available hydroxy groups in MeHA) of pyridine-sulfur trioxide complex (1.6 g) was added. After stirring for 3 h at 40° C., the reaction was quenched by adding 100 mL of water, and crude material was precipitated by adding 150 mL of cold ethanol saturated with anhydrous sodium acetate, and then collected by filtration. The resulting crude partially O-sulfated MeHA was dissolved in water, dialyzed, and lyophilized as in 1 to give the product (550 mg) in 63% yield, which was shown by 1H NMR to have a sulfation SD=1.5-2.0.

25. Preparation of P-OSBGHA (GM-431101)

The TBA salt of BGHA (from MW 950 kDa HA) was prepared from 0.5 mL of TBA and BGHA (0.5 g) in 50 mL of distilled water as in 1. The resulting salt (BGHA-TBA) was dissolved in 50 mL of DMF to which the required excess (6 mol/equiv of available hydroxyl groups in BGHA) of pyridine-sulfur trioxide complex (0.8 g) was added. After stirring for 3 h at 400 C, the reaction was quenched by adding 100 mL of water, and crude material was precipitated by adding 150 mL of cold ethanol saturated with anhydrous sodium acetate, and then collected by filtration. The resulting crude O-sulfated BGHA was dissolved in water, dialyzed, and lyophilized as in 1 to give the product (500 mg) in 60% yield, which was shown by 1H NMR to have a sulfation SD<1.

26. Preparation of F-OSBGHA (GM-432101)

The TBA salt of BGHA (from MW 950 kDa HA) was prepared from 0.5 mL of TBA and BGHA (0.5 g) in 50 mL of distilled water as in 1. The resulting salt (BGHA-TBA) was dissolved in 50 mL of DMF to which the required excess (12 mol/equiv of available hydroxyl groups in BGHA) of pyridine-sulfur trioxide complex (1.6 g) was added. After stirring for 3 h at 400 C, the reaction was quenched by adding 100 mL of water, and crude material was precipitated by adding 150 mL of cold ethanol saturated with anhydrous sodium acetate, and then collected by filtration. The resulting crude O-sulfated BGHA was dissolved in water, dialyzed, and lyophilized as in 1 to give the product (520 mg) in 61% yield, which was shown by 1H NMR to have a sulfation SD<1.

27. Preparation of P-OSBGHA (GM-411101)

The TBA salt of BGHA (from MW 53 kDa HA) was prepared from 0.5 mL of TBA and BGHA (0.5 g) in 50 mL of distilled water as in 1. The resulting salt (BGHA-TBA) was dissolved in 50 mL of DMF to which the required excess (6 mol/equiv of available hydroxyl groups in BGHA) of pyridine-sulfur trioxide complex (0.8 g) was added. After stirring for 3 h at 400 C, the reaction was quenched by adding 100 mL of water, and crude material was precipitated by adding 150 mL of cold ethanol saturated with anhydrous sodium acetate, and then collected by filtration. The resulting crude O-sulfated BGHA was dissolved in water, dialyzed, and lyophilized as in 1 to give the product (500 mg) in 60% yield, which was shown by H NMR to have a sulfation SD<1.

28. Preparation of P-OSBGHA (GM-412101)

The TBA salt of BGHA (from MW 53 kDa HA) was prepared from 0.5 mL of TBA and BGHA (0.5 g) in 50 mL of distilled water as in 1. The resulting salt (BGHA-TBA) was dissolved in 50 mL of DMF to which the required excess (12 mol/equiv of available hydroxyl groups in BGHA) of pyridine-sulfur trioxide complex (1.6 g) was added. After stirring for 3 h at 400 C, the reaction was quenched by adding 100 mL of water, and crude material was precipitated by adding 150 mL of cold ethanol saturated with anhydrous sodium acetate, and then collected by filtration. The resulting crude O-sulfated BGHA was dissolved in water, dialyzed, and lyophilized as in 1 to give the product (500 mg) in 60% yield, which was shown by 1H NMR to have a sulfation SD<1.

III. Preparation of Fluorescent SAGEs and Palmitoylated SAGE a. Preparation of LMW-F-OSFHA-I (DS-2) Fluorescent Conjugate LMW-F-OSFHA-1 (50 mg) and NHS (40 mg) were dissolved in 10 mL water, and then Alaxa fluo@488 (1 mg) in 4 mL DMF was added. And then pH was adjusted to 4.75. after that, 100 mg EDCI was added in solid form. The pH was kept at 4.75 by adding NaOH solution. The solution was stirred for overnight at room temperature with aluminum foil coverage. Then the product was purified by dialyzing against distilled water (cut-off MW 3500) and following methanol/water solution (50/50, v/v). further purified by gel filtration column (Sephadex G-25). Further purified by PD-10 column and lyophized to dry to obtain 40 mg.

b. Preparation of LMW-P-OSMeHA (DS-I) Fluorescent Conjugate

LMW-P-OSMeHA (50 mg) and NHS (40 mg) were dissolved in 10 mL water, and then Alaxa fluo@488 (1 mg) in 4 mL DMF was added. And then pH was adjusted to 4.75. after that, 100 mg EDCI was added in solid form. The pH was kept at 4.75 by adding NaOH solution. The solution was stirred for overnight at room temperature with aluminum foil coverage. Then the product was purified by dialyzing against distilled water (cut-off MW 3500) and following methanol/water solution (50/50, v/v), further purified by gel filtration column (Sephadex G-25), and further purified by PD-10 column and lyophized to dry to obtain 43 mg.

c. Preparation of Palmitoylated SAGE

LMW-P-OSMeHA (50 mg) was dissolved in 50 mL of DMF, triethylamine (0.3 mL) was added to the DMF solution while stirred. After 5 min, the palmitoyl chloride (0.5 mL) was added. The resulting mixture was kept stirring for overnight. The solution was evaporated, and the residue was dissolved in distilled water, dialyzed for one day (change water four times), and lyophilized to dry to obtained 35 mg.

IV. SAGEs are Potent Inhibitors of P-Selectin, Human Leukocyte Elastase and the Interaction of Rage with all of its Ligands Materials. Polyclonal goat anti-human RAGE, recombinant human high mobility box protein-1 (HMGB-I), recombinant human P-selectin/Fc chimera, recombinant human RAGE/Fc chimera, human azurocidin and polyclonal goat anti-human azurocidin were purchased from R&D Systems (Minneapolis, Minn.). Human S1006 calgranulin was from Calbiochem (San Diego, Calif.). The advanced glycation end-product carboxymethyl lysine-bovine serum albumin (CML-BSA) was obtained from MBL International (Woburn, Mass.). U937 human monocyte cells were obtained from American Type Culture Collection (Manassas, Va.). Protein A, horse radish peroxidase-conjugated rabbit anti-goat IgG, carbonate-bicarbonate buffer and bovine serum albumin blocker (1O×) were obtained from Piercenet (Rockford, Ill.). Calcein AM, Dulbecco's modified Eagle's medium (DMEM), ethylenediamine tetraacetic acid (EDTA), fetal bovine serum (FBS), HEPES, non-essential amino acids, penicillin/streptomycin/L-glutamine solution, RPMI-1640 without L-glutamine and sodium bicarbonate were obtained from Invitrogen (Carlsbad, Calif.). High-bind 96-well microplates were obtained from Corning Life Sciences (Corning, N.Y.). All other chemicals not specified were purchased from Sigma-Aldrich (St. Louis, Mo.).

Cell culture. U937 monocytes were grown in suspension culture at 37° C. in humidified 5% CO2-95% air in RPMI-1640 supplemented with 10% heat inactivated FBS, 2 mM L-glutamine, 1 mM sodium pyruvate, 0.1 mM MEM non-essential amino acids, 100 units/ml penicillin and 100 mg/ml streptomycin. Experiments were performed on cells from passages 1-5.

Cell Binding Assays. The effect of SAGEs on binding of U937 monocytes to P-selectin or RAGE was studied in high-bind micro plates coated with 8 µg/ml protein A (50 µg/well) in 0.2 M carbonate-bicarbonate buffer (pH 9.4). Plates were washed with phosphate buffered saline containing 1% BSA (PBS-BSA), and P-selectin-Fc or RAGE-Fc chimera (50 µL containing 1 µg) was added to each well and incubated for 2 h at room temperature or overnight at 4° C., respectively. Following incubation, wells were washed twice with PBS-BSA. Fifty (50) µL of SAGEs (0 to 1,000 µg/ml) serially diluted in 20 mM HEPES buffer (containing 125 mM NaCl, 2 mM calcium and 2 mM magnesium) were added to each well and incubated at room temperature for 15 min. As a negative control, 50 µL of 10 mM EDTA was added to select wells to prevent cell binding through sequestration of calcium. At the end of the incubation period, 50 µL of U937 cells (105 cells/well, calcein-labeled according to manufacturer's instructions) were added to each well and plates were incubated an additional 30 min at room temperature. The wells were then washed thrice with PBS, and bound cells were lysed by addition of 100 µL of Tris-TritonX-100 containing buffer. Fluorescence was measured on a microplate reader using excitation of 494 nm and emission of 517 nm.

Solid phase binding assays. Solid phase binding assays were used to study the ability of SAGEs to inhibit RAGE binding to its ligands. For studies of the effect of SAGEs on RAGE binding to its ligands, polyvinyl 96-well plates were coated with 5 µg/well of specific ligand (CML-BSA, HMGB-I or S100b calgranulin). Plates were incubated overnight at 4° C. and washed thrice with PBS-0.05% Tween-20 (PBST). Separately, RAGE-Fc chimera (100 µL containing 0.5 µg/ml in PBST-0.1% BSA) was incubated with an equal volume of serially diluted SAGEs (0.001 to 1,000 µg/ml in PBST-BSA) overnight at 4° C. The following day, 50 µL of RAGE-SAGE mix was transferred to each respective ligand-coated well and incubated at 37° C. for 2 h. Wells were then washed four times with PBST. To detect bound RAGE, 50 µL of anti-RAGE antibody (0.5 µg/ml) was added to each well, the mixture was incubated for 1 h at room temperature, and wells were washed again four times with PBST. Horse-radish peroxidase conjugated secondary antibody (1:10,000 antibody dilution in PBST; 50 µL per well) was added, wells were incubated for 1 h at room temperature, and then washed once with PBST. A colorimetric reaction was initiated by addition of 50 µL of tetramethyl benzidine chromogen (TMB single solution chromogen) and terminated after 15 min by addition of 50 µL of 1 N HCl. Absorbance at 450 nm was read using an automated microplate reader.

Enzymatic assays. To characterize SAGE inhibition of the cationic PMN protease HLE an activity assay (Fryer A, Huang Y-C, Rao G, Jacoby D, Mancilla E, Whorton R, Piantadosi C A, Kennedy T, Hoidal J. Selective O-desulfation produces nonanticoagulant heparin that retains pharmacologic activity in the lung. J Pharmacol Exp Ther 282:208-219, 1997) was employed, which measured the ability of purified HLE to cleave a chromogenic substrate. HLE (10 OnM) was incubated with SAGE (1-100 nM) in 0.5 M HEPES buffer for 15 min. Following incubation, the elastase substrate Suc-Ala-Ala-Val-p-nitroanaline (p-NA) was added to the reaction mixture to a final concentration of 0.3 mM. The hydrolysis of p-NA released was followed for 15 min by measuring the absorbance at 405 nm. In order to characterize the ability of SAGEs to activate Factor XII or complement, activity assays were employed that are similar to those recently used to screen for toxicity of adulterated commercial heparin (Kishimoto T K, Viswanathan K, Ganguly T, Elankumaran S, Smith S, Pelzer K, Lansing J C, Sriranganathan N, Zhao G, Galcheva-Gargova Z, Al-Hakim A, Bailey G S, Fraser B, Roy S, Rogers-Cotrone T, Buhse L, Whary M, Fox J, Nasr M, Dal Pan G J, Shriver Z, Langer R S, Venkataranam G, Austen K F, Woodcock J, Sasisekharan R. Contaminated heparin associated with adverse clinical events and activation of the contact system. N Engl J Med 358:2457-2467, 2008; Guerrini M, Beccati D, Shriver Z, Naggi A, Viswanathan K, Bisio A, Capila I, Lansing J C, Guglieri S, Fraser B, Al-Hakim A, Gunay N S, Zhang Z, Robinson L, Buhse L, Nasr M, Woodcock J, Langer R Venkataraman G, Li nhardt R J, Casu B, Torn G, Sasisekharan R. Oversulfated chondroitin sulfate is a contaminant in heparin associated with adverse clinical events. Nat Biotech 26:669-675, 2008). Pooled human plasma (5 µl) was incubated with 100 µl of SAHA (0.1 to 1000 µg/ml) in 0.05 M HEPES containing Triton X-100 for 5 min at 5° C. Amidolytic activity specific for Hageman factor was determined by adding 0.5 mM D-cyclohydrotyrosyl-Glyc-L-Arg-p-NA and following the change in absorbance at 405 nm (Silverberg M, Dunn J T, Garen L, Kaplan A P. Autoactivation of human Hageman factor. Demonstration using a synthetic substrate. J Biol Chem 255:7281-7286, 1980).

Amidolytic activity specific for active kallikrein was determined by adding D-Pro-Phe-Arg-/7-NA and following change in absorbance at 450 nm.

Figure 3:
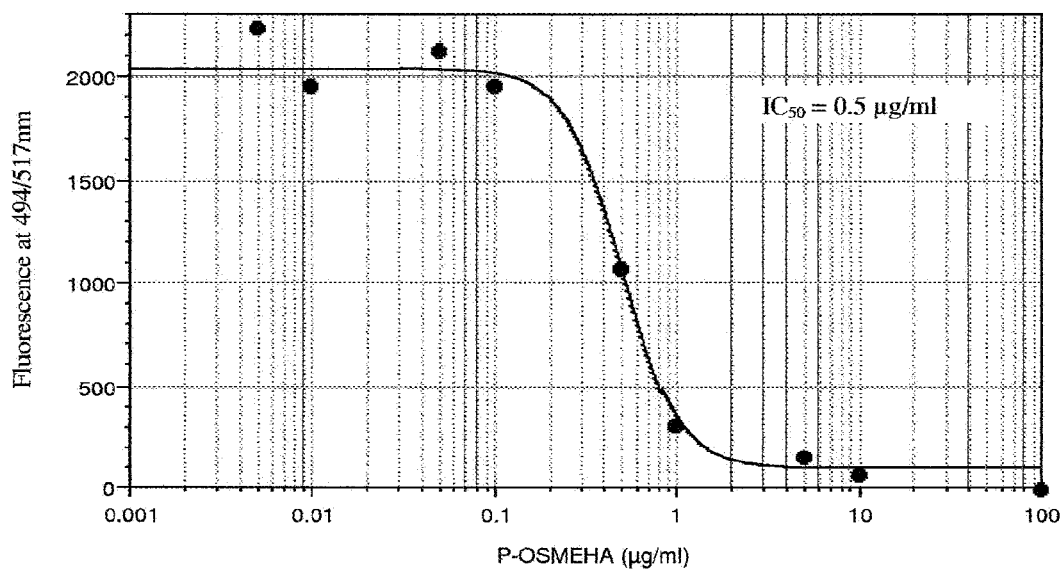
FIG. 3 shows the inhibition of P-Selectin by partially O-sulfated and methylated HA (P-OSMEHA, or GM-131201).

Results: The results of the assays are shown in Table 2. SAGEs are potent inhibitors of P-selectin. The competitor-mediated displacement of U937 human monocytes, which firmly adhere to P-selectin through P-selectin glycoprotein ligand-1 (PSGL-I), was studied using fluorescently-labeled cells. FIG. 3 shows that a SAGE inhibits U937 binding to P-selectin with a 50% inhibitory concentration (IC50) of 0.5 µg/ml.

TABLE 2

SAGE In Vitro Data

| SAGE | P-Selectin/PSGL | RAGE/Mac-1 | RAGE/CML-BSA | RAGE/S100B | RAGE/HMGB1 | Leukocyte Elastase | Hageman Factor |
|---|---|---|---|---|---|---|---|
| GM-111101 | 0.14 | 0.042 | 2.27 | 1.56 | 0.455 | 0.22 | 4 |
| GM-111201 | 0.017 | 0.033 | 0.082 | 0.077 | 1.033 | 0.54 | 0.4 |
| GM-112101 | 2.164 | 0.113 | 0.002 | 0.042 | 0.537 | 0.187 | 0.4 |
| GM-112201 | 0.496 | 0.152 | 0.005 | 0.017 | 0.634 | 0.117 | 0.4 |
| GM-131101 | 5.61 | 0.51 | 6.09 | 31.069 | 2.68 | 0.285 | NR |
| GM-131201 | 0.5 | 0.3 | 0.044 | 0.06 | 1.66 | 0.42 | 0.4 |
| GM-132101 | 0.0794 | 0.0297 | 0.015 | 0.004 | 0.501 | 0.127 | 0.4 |
| GM-132201 | 0.22 | 0.004 | 0.1 | 0.04 | 0.228 | 0.24 | 0.4 |
| GM-211101 | 6.53 | 2.11 | NR | NR | NR | 0.133 | NR |
| GM-211201 | NR | NR | NR | NR |  | 0.54 | 400 |
| GM-212101 | 5.13 | 6.51 | 10.5 | 15.671 | NR | 0.357 | NR |
| GM-212201 |  |  | 0.019 | 0.015 |  | 0.217 | 0.4 |
| GM-231101 | 12.048 | NR | NR | 14.6 | NR | 0.185 | 400 |
| GM-231201 | 0.126 | 28.4 | 2.579 | 8.82 | NR | 0.487 | 400 |
| GM-232101 | 0.883 | 4.78 | 0.041 | 0.02 | 0.408 | 0.19 | 4 |
| GM-232201 | 0.579 | 0.142 | 0.019 | 0.021 | 0.51 | 0.202 | 0.4 |
| GM-311101 | NR | 4.7 | 2.452 | 7.358 | NR | 0.439 | NR |
| GM-311201 | NR | NR | NR | NR |  | 0.52 | 400 |
| GM-312101 | 0.897 | 0.34 | 0.299 | 0.56 | 0.454 | 0.261 | NR |
| GM-312201 | 0.036 | 0.009 | 0.059 | 0.075 |  | 0.47 | 0.4 |
| GM-331101 | 8.958 | NR | NR | 4.557 | NR | 0.375 | 400 |
| GM-331201 |  |  | 1.682 | 2.28 | NR | 0.353 | 40 |
| GM-332101 |  | 0.108 | 0.015 | 0.021 | 0.371 | 0.184 | 40 |
| GM-332201 | 38.3 | 0.0879 | 0.096 | 0.22 | 1.074 | 0.392 | 4 |
| GM-411101 | 0.342 | 0.0515 | 14.602 | NR | NR | 0.884 | NR |
| GM-412101 | 1.05 | 0.146 | 0.053 | 0.3 | 0.606 | 0.234 | 0.4 |
| GM-431101 | 0.059 | NR | NR | 89.5 | NR | 0.268 | NR |
| GM-432101 | 2.586 | 4.36 | 1.327 | 0.85 | 0.184 | 0.195 | NR |
| IC50 values (ug/ml) | | | | | | | |
| Heparin | 0.3 | 0.11 | 0.39 | 1.29 | 0.04 | 0.21 | 0.4 |
| ODSH | 1.1 | 0.09 | 8.6 | 4.2 | 0.23 | 0.22 | NR |

TABLE 3

IC$_{50}$ values (μg/mL) for GM-1111 batches

| SAGE | RAGE/CM L-BSA | RAGE/S 100B | RAGE/HM GB1 | Leukocyte Elastase | Hagemann Factor | Sulfation |
|---|---|---|---|---|---|---|
| GM-111101 | 2.27 | 1.51 | 0.438 | 0.22 | 4 | 12% |
| GM-111102 | 0.0815 | 0.0293 | 0.734 | 0.201 | NA | 14% |
| GM-111103 | 0.0108 | tbd | 0.409 | 0.211 | 0.4 | 12% |
| GM-111104 | 6.2 | 4.33 | 62.8 | 0.321 | NA | 4% |
| GM-111105 | 20.7 | 2.45 | 89.4 | 0.447 | 400 | 3% |
| GM-111106 | 0.00499 | 0.0343 | 0.299 | 0.337 | 4-400 | 7% |
| GM-111107 | 0.0689 | 0.0158 | 1.05 | tbd | 0.4-40 | 8% |
| GM-111108 | tbd | tbd | tbd | tbd | tbd | 12% |

Figure 4:
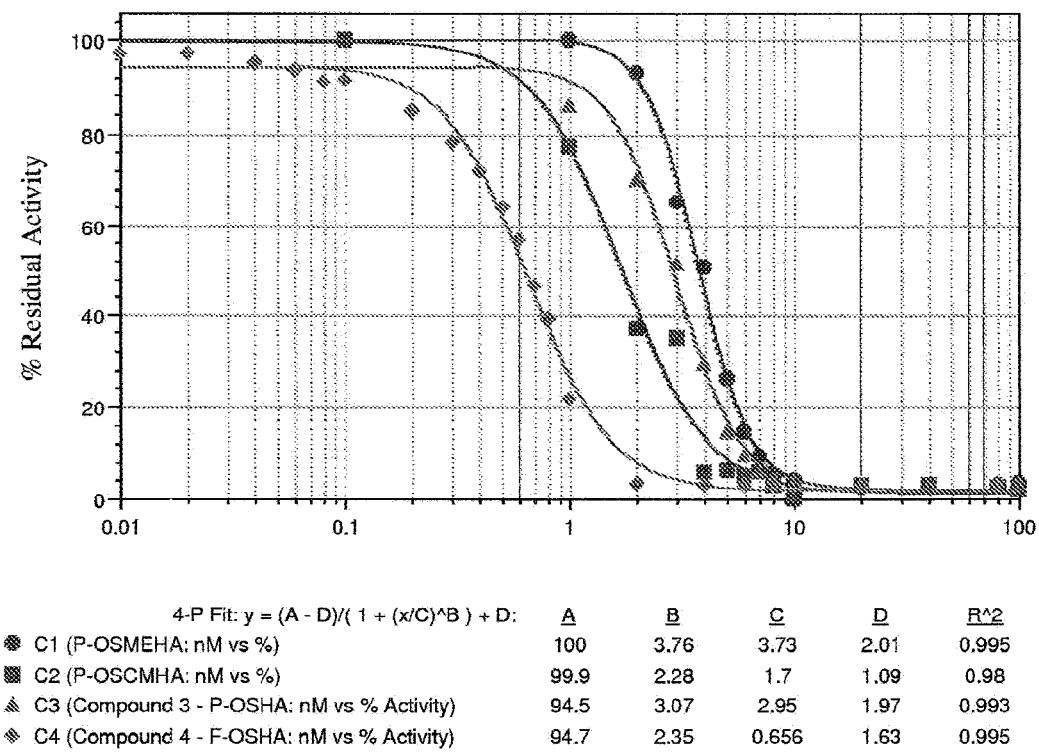
FIG. 4 shows the inhibition of human leukocyte elastase by sulfated hyaluronan derivatives, including alkylated and non-alkylated hyaluronans, which are also sulfated.

Second, as highly sulfated polyanions, alkylated and sulfated SAGEs are potent inhibitors of polymorphonuclear leukocyte proteases. FIG. 4 shows that alkylated and/or fluoroalkyated and sulfated SAGEs inhibit human leukocyte elastase (HLE) with impressively potent IC50 values. Specifically, the non-alkylated, fully O-sulfated HA (F-OSHA) shows an 0.66 nM IC50 for HLE. For the modified and sulfated HA derivatives, IC50 values were I.89 nM for partially O-sulfated ■ carboxymethylated HA (P-OSCHMHA); 1.97 nM for partially O-sulfated HA (P-OSHA); and 3.46 nM for partially O-sulfated methylated HA (P-OSMEHA; GM-131101).

Figure 5:
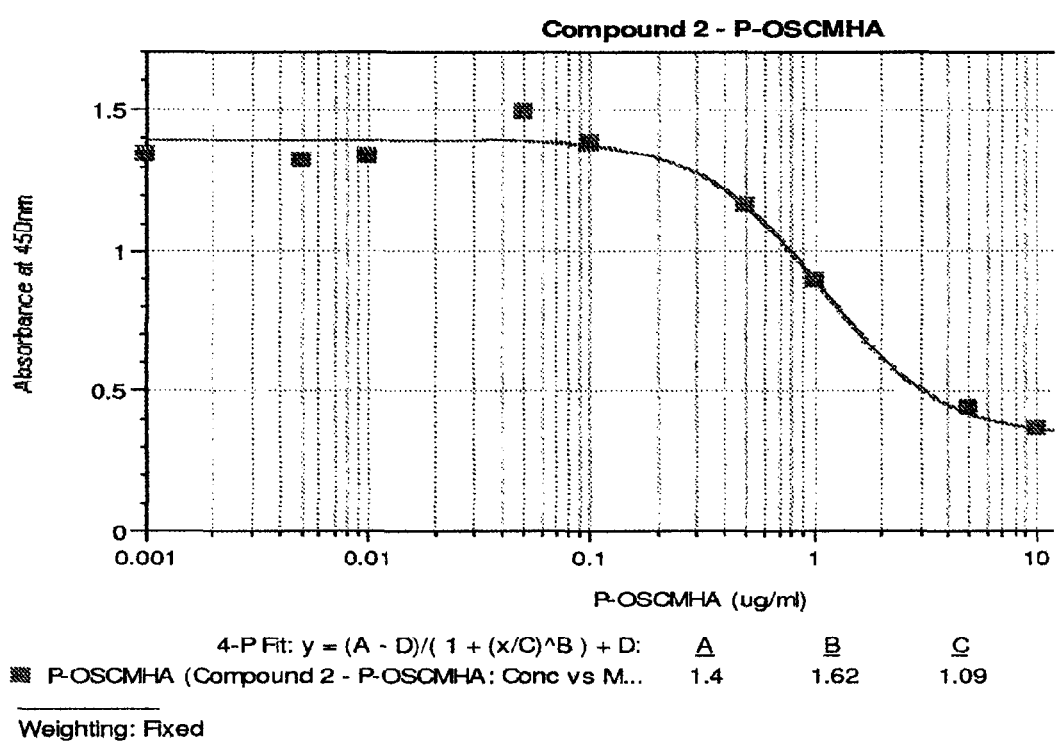
FIG. 5 shows the inhibition of amphoterin, also known as high mobility group box protein-1 (HMGB-I) binding to immobilized RAGE by P-OSMEHA
Figure 6:
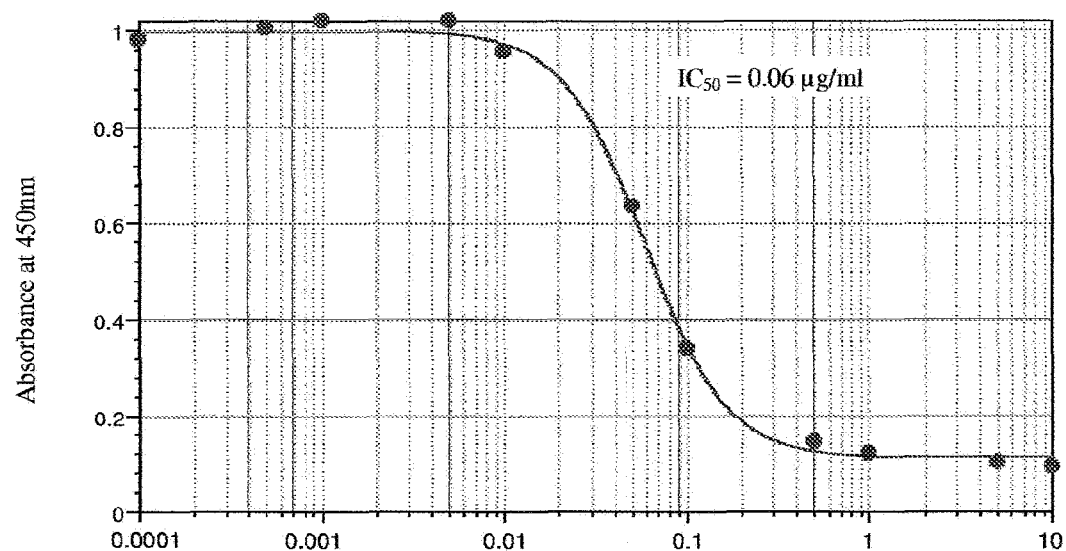
FIG. 6 shows the inhibition of S100b calgranulin binding to immobilized RAGE by P-OSMEHA (GM-131201).
Figure 7:
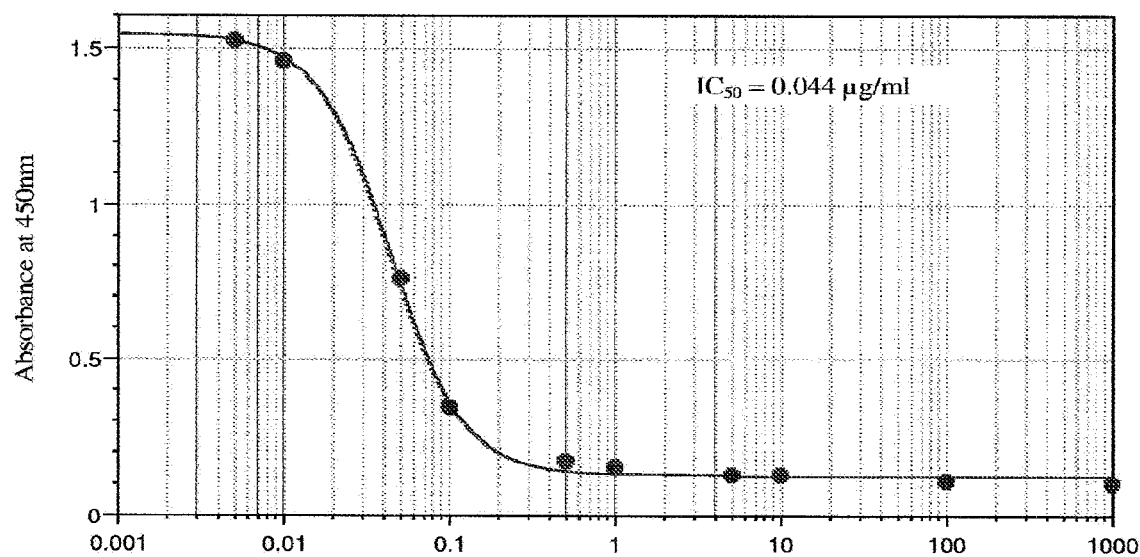
FIG. 7 shows the inhibition of carboxymethyl lysine-BSA (CML-BSA) binding to immobilized RAGE by P-OSMEHA (GM-131201).

Third, SAGEs are extremely potent inhibitors of RAGE. SAGEs inhibited the interaction of RAGE and amphoterin (HMGB-I) with an IC50 of 1.1 μg/ml (FIG. 5), the interaction of RAGE and S100 calgranulins with an ICs0 of 60 ng/ml (FIG. 6), and the binding of RAGE to the AGE product carboxymethyl-lysine BSA with an IC50 of 44 ng/ml (FIG. 7). These values are 5 to 10-fold more potent than corresponding levels of RAGE-ligand inhibition we have measured with heparin and 2-0,3-0 desulfated heparin.

Figure 8:
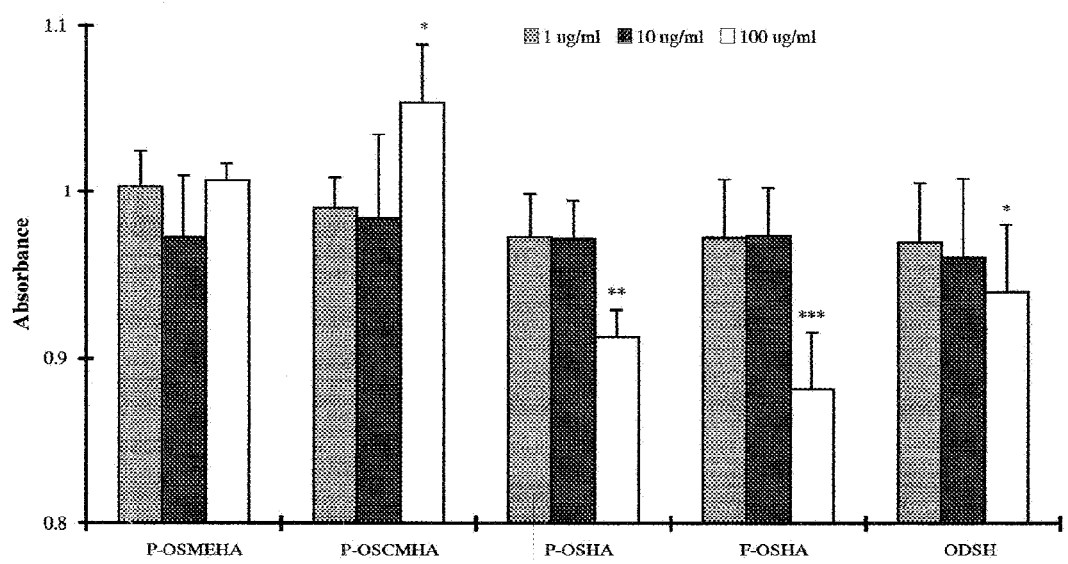
FIG. 8 shows the inhibition of keratinocyte proliferation by high molecular weight hyaluronan derivatives, including alkylated and non-alkylated hyaluronans, that are also sulfated.
Figure 9:
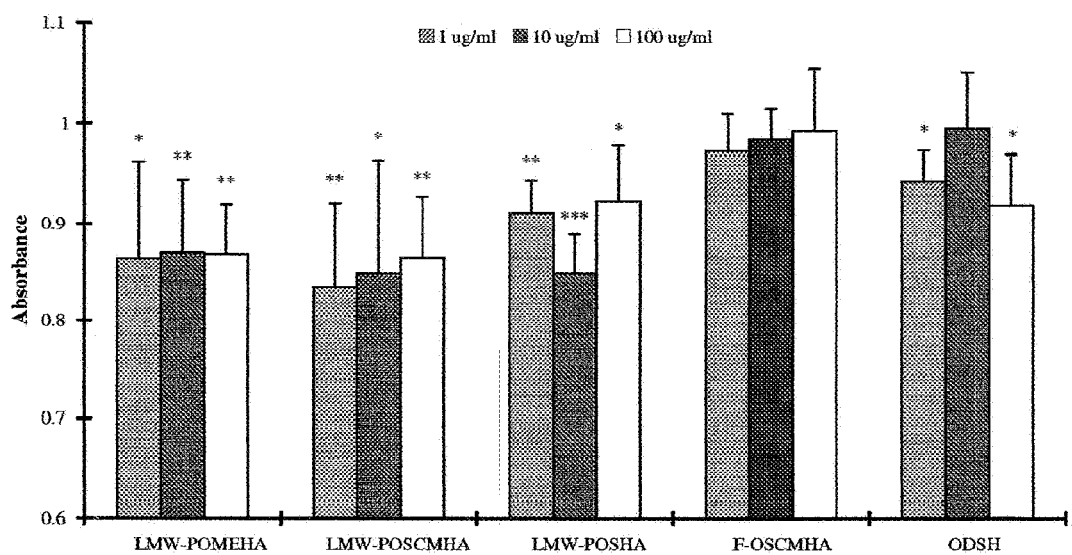
FIG. 9 shows the inhibition of keratinocyte proliferation by low molecular weight hyaluronan derivatives, including alkylated and non-alkylated hyaluronans, which are also sulfated, and by 2,3-O desulfated heparin (ODSH).

Fourth, SAGEs are potent inhibitors of the proliferation of human keratinocytes. In these assays human neonatal epidermal keratinocytes were cultured in the presence and absence of SAGEs or other inhibitors, and proliferation was measured by adding a dye that is reduced in direct proportion to the number of viable cells present. In the figures displayed, absorbance values were normalized to controls, which were assigned a relative absorbance of 1.0. FIG. 8 shows that the high molecular weight partially O-sulfated HA (P-OSHA) and fully O-sulfated HA (F-OSHA) were more effective than the heparin derivative 2-0, 3-0 desulfated heparin (ODSH) at preventing keratinocyte proliferation when added in concentrations of 100 μg/ml. Higher sulfation appears advantageous, since partially sulfated carboxymethylated HA (P-OSCMHA) and methylated HA (P-OSMEHA; GM-131101) were less active at inhibiting keratinocyte proliferation. FIG. 9 shows that overall lower molecular weight (LMW) derivatives were more effective than higher molecular weight derivatives at reducing keratinocyte proliferation in this assay. In particular, the LMW partially O-sulfated MeHA (LMW-P-OMEHA; GM-111201), partially O-sulfated CMHA (LMW-P-OSCMHA) and partially O-sulfated 53 kDa HA itself (LMW-P-OSHA) all reduced proliferation relative to controls at concentrations as low as 1 μg/ml.

GM-1111 can be prepared from different sources of hyaluronic acid with different polydispersities and initial average molecular weights. The in vitro biochemical results, in vivo biological activities, and alkylation/sulfation levels vary based on the size and solubility of the starting HA. To our surprise, starting with poorly soluble HA of size 60-70 kDa resulted in low levels of methylation, sulfation, and dramatically reduced biological activities. In contrast, starting with readily soluble HA of sizes 40-60 kDa (whether obtained commercially at this size or prepared by partial depolymerization of a higher molecular weight HA starting material) resulted in reproducible levels of methylation, sulfation, and high biological activity.

V. In Vivo Studies for the Treatment of Rosacea and Inflammation Materials and Methods Chemicals. GM-111101, GM-131101, GM-312101 and GM-212101 were evaluated. Medium was bought from American Type Culture Collection (ATCC). EpiLife medium was purchased from Invitrogen (Madison, Wis.).

Cells. The Human Dermal Fibroblasts (nHDF) were purchased from ATCC. Human neonatal epidermal keratinocytes (HEKn) were obtained from Invitrogen (Madison, Wis.).

Cytotoxicity. 4,000 nHDF cells were seeded 100 μl medium in each well of 96-well flat-bottomed microplates, and incubated at 37° C. in 5% CO2 for 12 hours. All the medium was changed with complete medium containing a variety of sulfated hyaluronan (HA) derivatives at final concentrations of 10, 100, 1000, 10000, 100000, 1000000 ng/ml to each column. At 48 hours, 20 μl MTS (Promega, Madison, Wis.) was pipetted into each well, and cells were further incubated for 2 hours. The absorbance of the samples was measured at 490 nm using a 96-well plate reader.

Skin irritation test in mice. GM-111101 and GM-212101 were tested in vivo to determine the dermal irritation potential to the skin of the mice. The two test agents were prepared with two different concentrations individually, 0.1 mg/ml and 1 mg/ml. 10% formic acid and PBS were used as positive and negative control respectively (n=6). Balb/c mice, which had not been used in previous experiments and were observed to be free from any skin irritation, trauma, or adverse clinical signs prior to initiation of the studies, were randomized and grouped for designed test conditions. The back of the animals was clipped free of fur with an electric clipper at least 4 hours before application of the sample. Just prior to test substance application, each mouse received four parallel epidermal abrasions with a sterile needle at the bottom area of the test site while the upper area of the test site remained intact. Under anesthesia, two 0.5-ml samples of the test solution were applied to the entire test site by introduction under a double gauze layer to an area of skin approximately 2.5 cm square. The patches were backed with plastic, covered with a non reactive tape and the entire test site wrapped with a bandage. Animals were returned to their cages. After a 24 hr exposure to the agent, the bandage and soaked test gauze were removed. The test sites were wiped with tap water to remove any remaining test compound. At 24 and 72 hours after compound application, the test sites were examined for dermal reactions in accordance with the FHSA-recommended Draize scoring criteria. The Primary Irritation Index (P.I.I.) of the test article will be calculated following test completion. A material producing a P.I.I, score of greater than or equal to 5.00 would be considered positive; the material would be considered a primary irritant to the skin. Animals. Balb/c mice were purchased commercially from a vendor approved by the Univ. of Utah veterinary medicine department and vivarium. After they are quarantined for the prescribed period following receipt, they are ready for use.

LL37 peptide and SAGE injection roceasea models. Chronic disease of the skin leaves an indelible mark on the patients life, especially, as in the case of rosacea, when it presents on the face. As a species, we react positively or adversely to one another's appearance, instinctively recoiling from those who appear abnormal and unlike ourselves. While skin diseases are not often life-threatening, they are life-altering in ways that normal individuals do not fathom. Rosacea is one of those life-altering illnesses. Rosacea is a common disfiguring facial skin disease affecting 3% of the U.S. population, or about 14 million Americans, with onset usually between the ages of 30 and 50 years. It strikes primarily in Caucasians of Celtic descent, and appears to be more problematic and common in women than men. Over a third of patients have a family history, strongly suggesting an inherited illness. The condition is particularly stigmatizing because of the common misconception that the facial redness and the knobby nose of rosacea are the consequence of excessive alcohol consumption. Rosacea presents as several clinical phenotypes. The most common presentation is characterized by transient or persistent central flushing and erythema of the face, with dilated capillaries on the cheeks and nose. This phenotype ranges from a "ruddy complexion" to persistent, readily visible dilated vessels. This subtype is without an effective topical treatment. In a second common presentation, papules and pustules occur on the central convexities of the face, frequently superimposed upon a background of erythema. On biopsy, the skin is richly infiltrated with PMNs. Papulopustular rosacea is treated empirically with topical or systemic antibiotics, but is not clearly related to documented cutaneous infection. Macrolides, either topically or systemically, been most often used as therapy, and may produce improvement not because of their anti-bacterial activity so much as their ability to retard PMN chemotaxis into areas of inflammation. In a third and fortunately more rare phenotype, rosacea produces rhinophyma from hyperplasia of both the sebaceous glands and connective tissue of the nose, creating the classical "W.C. Fields" nose, or "whiskey nose". Treatment of this condition requires surgical excision of the tissue, or laser therapy, to remove hypertrophied tissue. In a fourth phenotype, rosacea can produce dry, itchy eyes with irritation of the lids (blepharitis), photosensitivity, blurred vision and conjunctivitis. Prolonged disease can result in keratitis and even corneal scarring. This phenotype, which arises from inflammation of the lids and the meibomian glands on the lower lid surface, is common and overlaps clinically with the "dry-eye" syndrome seen frequently by ophthalmologists. The occurrence of rosacea exclusively on sun-exposed facial areas in those with fair skin and light eyes points to a pathogenic role for solar radiation in causing the condition. The pathogenesis of rosacea has recently been elucidated (Yamasaki K, Di Nardo A, Bardan A, Murakami M, Ohtake T, Coda A, Dorschner R A, Bonnart C, Descargues P, Hovnanian A, Morhenn V B, Gallop R L. Increased serine protease activity and cathelicidin promotes skin inflammation in rosacea. Nat Med 13:975-980, 2007; Bevins C L, Liu F-T. Rosacea: skin innate immunity gone awry? Nat Med 13:904-906, 2007). In elegant work Yamasaki et al. demonstrated that the skin involved with rosacea contains high levels of cathelicidins and their processing protease SCTE. Cathelicidins, a major family of antimicrobial peptides in mammals, are expressed in leukocytes and epithelial cells of many organs, where they mediate innate immune responses to bacteria (Nizet V, Ohtake T, Lauth X, Trowbridge J k, Rudisill J, Dorschner R A, Prestonjamasp V, Piraino J, Huttner K, Gallop R L. Innate antimicrobial peptide protects the skin from invasive bacterial infection. Nature 414:454-457, 2001). Cathelicidins also signal vascular growth, PMN migration and wound healing (Bevins, ibid). Human cathelicidin is secreted by keritinocytes as an 18-kDa hCAP18 pro-peptide and cleaved by SCTE to the C-terminal active anti-microbial peptide LL-37, designated after its 37 amino acid length and two N-terminal leucines. Skin involved with rosacea demonstrates inappropriately high levels of both cathelicidins and SCTE without clearly inciting microbial invasion as a stimulus. When placed in the culture media covering primary human keritinocytes LL-37 greatly augments production of chemotactic cytokines such as IL-8. When injected intradermally into mice in levels similar to those found in rosacea-involved skin, LL-37 produces erythema and stimulates prominent dermal infiltration by PMNs. Intradermal injection of SCTE also produces skin erythema and PMN infiltration of the dermis in wild type, but not in cathelicidin'7" mice. Thus, there is a growing body of evidence which supports the concept that rosacea is mediated by V local over-expression of pro-inflammatory, cationic skin peptides which produce the inflammation, excessive angiogenesis and sebaceous hyperplasia characteristic of the disease. Because nearly every patient with rosacea can tell which of his parents has a pattern of reactive facial flushing and blushing, it is apparent to clinicians that rosacea is genetically driven. To produce a model of rosacea, LL-37 was injected intradermally every 12 h for 48 h. This model produced erythema of the skin and prominent intradermal infiltration of polymorphonuclear leukocytes (PMNs), as reported by Yamasaki et al. Balb/c mice were shaved prior to study to expose an area of skin on the back. Twenty-four hours later, we injected 40 μL of vehicle (phosphate buffered saline, PBS), cationic peptide (at 320 μM concentration in PBS), SAGE (320 to 1,280 μM in PBS), or cationic peptide+SAGE mix (peptide+Ix to 4x molar concentrations of SAGE) intradermally into the shaved skin using a 31 gauge needle in a manner designed to raise an intact epidermal bleb, thereby identifying that administration was at the level of the lower epidermis or dermis. SAGE selected for injection were chosen from over twelve newly synthesized SAGEs, which were tested extremely active in biochemical assays as inhibitors of human leukocyte elastase (as another cationic protein) and as antagonists for activation of the receptor for advanced glycation end-products (RAGE) by four common ligands.

SAGEs and peptides were mixed together in PBS prior to injection and allowed to incubate 15 min at room temperature before being injected. Injections were repeated every 12 h thereafter. Forty-eight hours after the initial injection (four injections in total), animals were lightly anesthetized with 25 mg/kg pentobarbital When the mouse was asleep, the area of injected skin was photographed to visually record the severity of erythema and edema. The intensity of erythema was assessed as a redness score (from 1 to 5), and the area of erythema was measured with calipers. The area of injected skin was then excisionally biopsied using a 6 mm hole punch for hematoxylin-eosin staining to examine the histopathologic changes and to assess PMN infiltration through measurement of myeloperoxidase (MPO) activity. One representative image of skin surface and histology from each skin was viewed under high power viewing under a microscope.

SAGE topical treatment rosacea model. Balb/c mice were shaved in time from LL37 exposure on area of skin on the back. We then began topical application of a hyaluronan-cased emollient containing 5% SAGEs (active emollient) or hyaluronic acid based emollient alone to this area of skin every 12 hours. Twenty-four hours later, we injected 40 µL of vehicle (PBS) or cationic peptide (at 320 µM concentration) subcutaneously into the shaved skin in the manner described previously. Injections and topical emollient applications were repeated every 12 h thereafter. Forty-eight hours after the initial injection (four injections in total), animals were lightly anesthetized as described previously. The area of injected skin was photographed to visually record the severity of erythema and edema. The intensity of erythema was assessed as a redness score (from 1 to 5), and the area of erythema was measured with calipers. The area of injected skin was then excisionally biopsied using a 6 mm hole punch for H&E staining to examine the histopathologic changes and to assess PMN infiltration through measurement of myeloperoxidase (MPO) activity.

SAGE dermis penetration. Balb/c mice were shaved prior to study to expose an area of skin on the back. Topical application of SAGE was carried out to the skin every 12 h. Forty-eight hours later animals were euthanized and the skin was biopsied. Sections of skin were then studied by fluorescence microscopy to determine the depth to which SAGEs penetrate into the skin.

*Croton* oil inflammation model. As another model of PMN-mediated skin inflammation, *croton* oil was employed. *Croton* oil contains phorbol esters, which activate protein kinase C in skin cells. As a result, skin cell produce abundant chemokines and chemotaxins which signal the influx of PMNs from the circulation. Activated PMNs produce erythema and edema of skin tissues. *Croton* oil induced inflammation is a commonly employe model of PMN-mediated skin inflammation in the screening of anti-inflammatory compounds for dermatologic use.

To produce this model, *croton* oil (Sigma-Aldrich, St. Louis, Mo.) was mixed as a 0.8% solution in acetone. Using a pipette, 10 µl were painted onto each side of one ear of the mouse, with the other ear remaining as a control. At 4, 8 and 24 hours later, ear thickness was measured near the top of the ear distal to the cartilaginous ridges. Change in ear thickness from control was then taken as an index of edema. The intensity of erythema was assessed as a redness score (from 1 to 5), and the area of erythema was measured with calipers. Following the 24 hour measurements, mice were euthanized and ear punch biopsies (6 mm hole punch) were taken immediately, weighted, frozen and stored at −800 C for H&E staining to examine the histopathologic changes and to assess PMN infiltration through measurement of myeloperoxidase (MPO) activity. A single investigator performed all ear measurements and biopsies in order to standardize the procedure and reduce error. The remainder of ears were removed, embedded and frozen for immunohistochemistry.

Myeloperoxidase (MPO) assay. For each mouse, tissue biopsies (6 mm diameter hole punch) were taken immediately, weighted, frozen and stored at −800 C. Tissue MPO activity was measured using a method by Suzuki et. al. (Suzuki K, Ota H, Sasagawa S, Sakatani T, Fujikura T. Assay method for myeloperoxidase in human polymorphonuclear leukocytes. Anal Biochem 132:345-352, 1983) as modified by Young et. al. (Young J M, Spires D A, Bedord C J, Wagner B, Ballaron S J, De oung L M. The mouse ear inflammatory response to typical arachidonic acid. J Invest Dermatol 82:367-371, 1984). Each mouse tissue biopsy was placed in 0.75 mL of 80 mM phosphate-buffered saline (PBS) pH 5.4 containing 0.5% hexadecyltrimethyl-ammonium bromide (HTAB). Each sample was homogenized for 45 s at 4° C. with a small laboratory Tissue Tearor Homogenizer Model 985-370 (Biospec Products, Bartlesville, Okla.). The homogenate was transferred quantitatively to a microcentrifuge tube with an additional 0.75 mL HTAB in PBS. The 1.5 mL sample was centrifuged at 12,000×g for 15 min, maintained at 4° C. Triplicate 30 uL samples of the resulting supernatant were added to 96-well microtier plate wells. For the MPO assay, 200 uL of a mixture containing 100 uL of 80 mM PBS (pH 5.4), 85 uL of 0.22 M PBS (pH 5.4), and 15 uL of 0.017% hydrogen peroxide were added to each well. 20 uL of 18.4 mM tetramethylbenzidine HCl in 8% aqueous dimethylformamide was added to start the reaction. Microtiter plates were incubated at 37° C. for 3 min, and then placed on ice. The reaction was stopped with the addition of 30 uL of 1.46 M sodium acetate. MPO enzyme activity was assessed at an absorbance wavelength of 630 nm. MPO activity was expressed as optical density (OD)/biopsy.

Statistical Analyses. All experiments were performed in triplicate for in vitro tests. Significance differences between samples were calculated by comparison of means using the Aspin-Welch test. Significance was declared at/?<0.05.

Results

Figure 10:
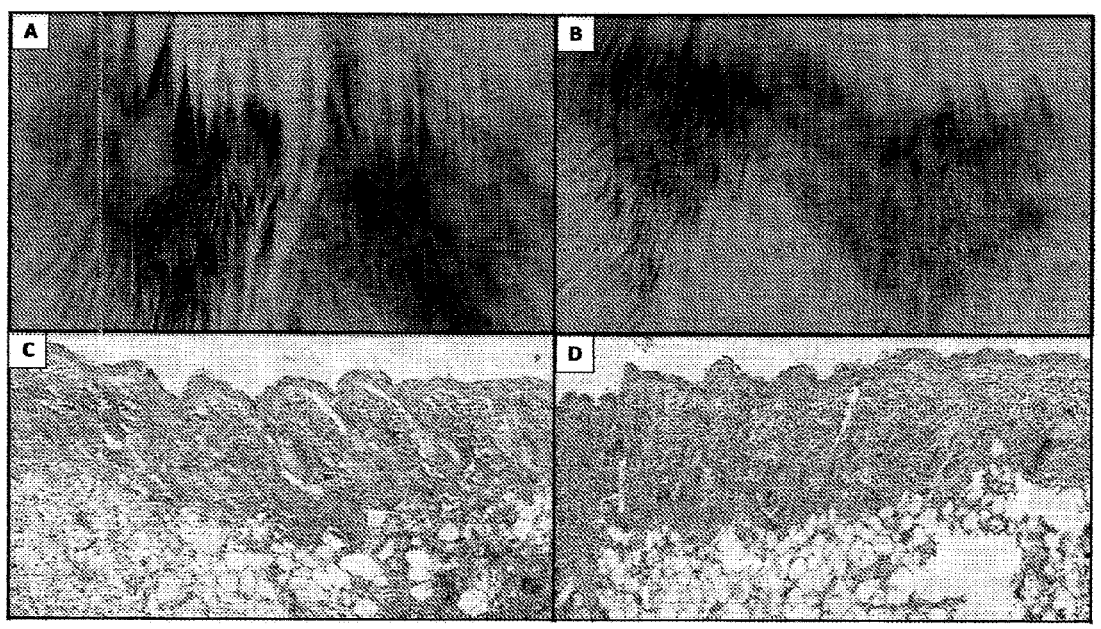
FIG. 10 shows SAGE (GM-111101) co-injection with LL-37 rosacea model, (a) Gross picture of LL-37 injected skin region and (b) co-injection model of LL-37 and SAGE, (c) H&E-stained cross-sectional view of a LL-37 injected skin sample, (d) H&E-stained cross-sectional view of a LL-37 mixed with SAGE injected skin region, (e) Polymorphonuclear leukocyte (PMN) infiltration into skin as measured by activity of the PMN enzyme myeloperoxidase (MPO) in skin biopsies from mice injected with LL-37 only, LL-37 plus SAGE or SAGE only injection groups, (f) area of erythema and (g) erythema score in mice injected with LL-37 only or LL-37 plus SAGE.
Figure 10:
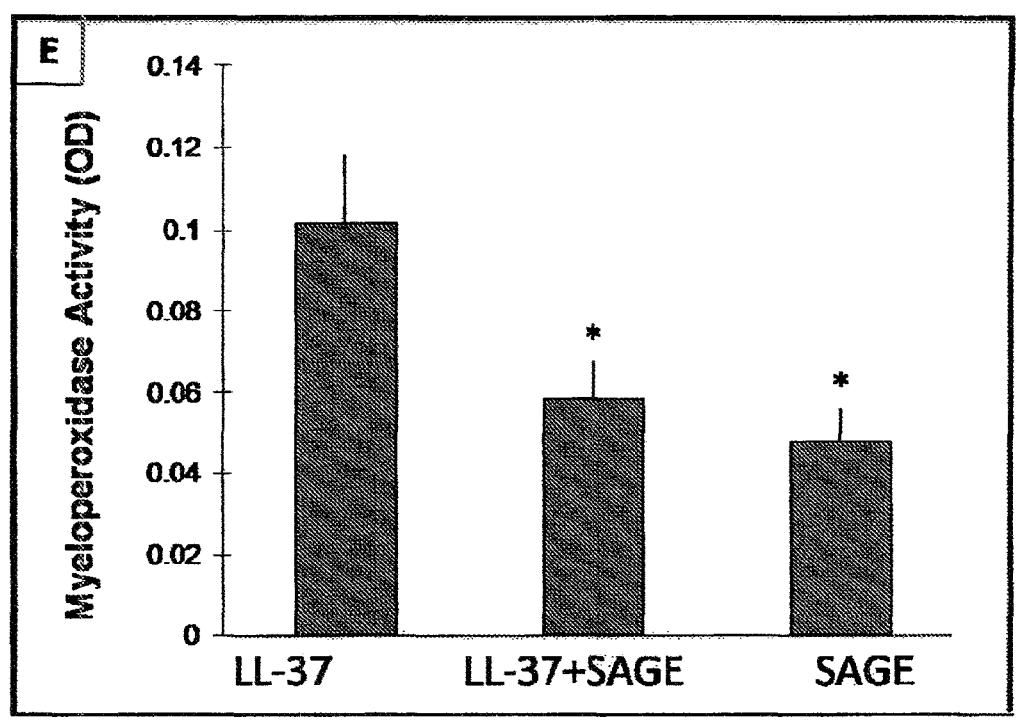
Figure 10:
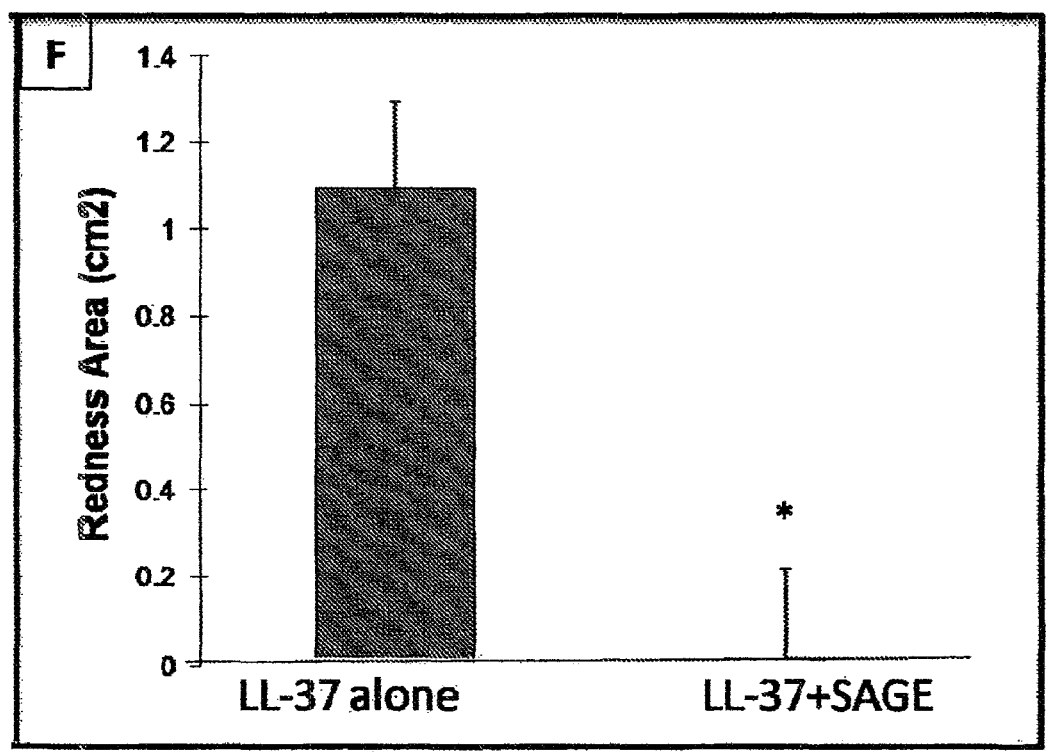
Figure 10:
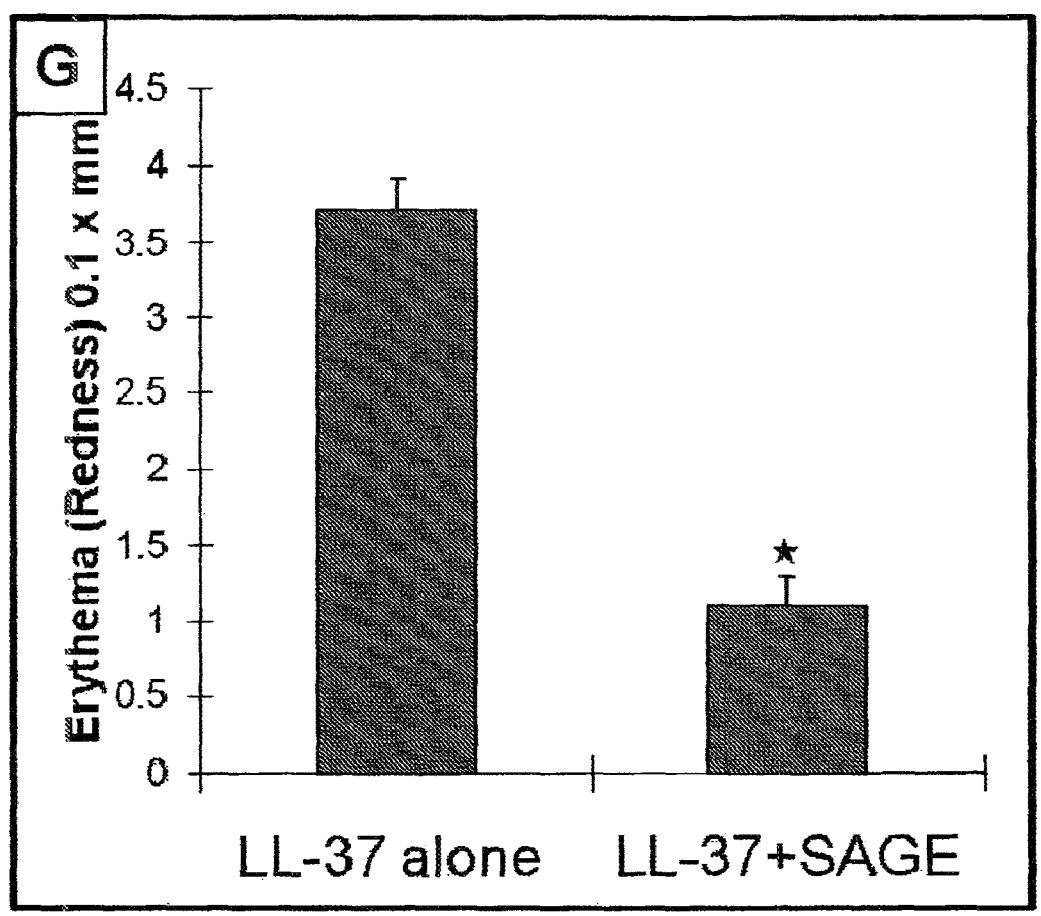

LL37 peptide and SAGE injection roceasea models. To determine if direct neutralization of cationic cathelicidins prevented their inflammatory activity in the skin, LL37 only, SAGE (GM-111101) only, vehicle (PBS) only, or mixture of LL37 and SAGE were subcutaneously injected into the shaved back area of mice every 12 h thereafter. After 48 hours, mice were sacrificed and gross pictures in different treatment groups were taken (FIGS. 10a and 10b). Histological studies using hematoxylin and eosin staining showed increased number of leukocytic infiltration and marked dermal edema, whereas SAGE administration immediately after challenge resulted in the inhibition of skin swelling response (FIGS. 10c and 10d). Individual results of dermal scoring were expressed by erythema area (FIG. 10f) and erythema redness score (FIG. 10g). After 48 hours, the SAGE treated group demonstrated a dramatically decreased area of erythema and a significant reduction of redness score. Myeloperoxidase activity was measured in the tissue punch biopsies taken 48 hr after injection as an index of PMN infiltration. SAGE coadministration with LL-37 peptide significantly reduced MPO activity by 50% (FIG. 10e). Therefore, co-injection of SAGE with LL-37 peptide substantially induced the inflammatory activity of the LL-37 cathelicidin peptide. This indicates that SAGEs inhibit LL37 mediated inflammation and would be useful treatments for rosacea.

Figure 11:
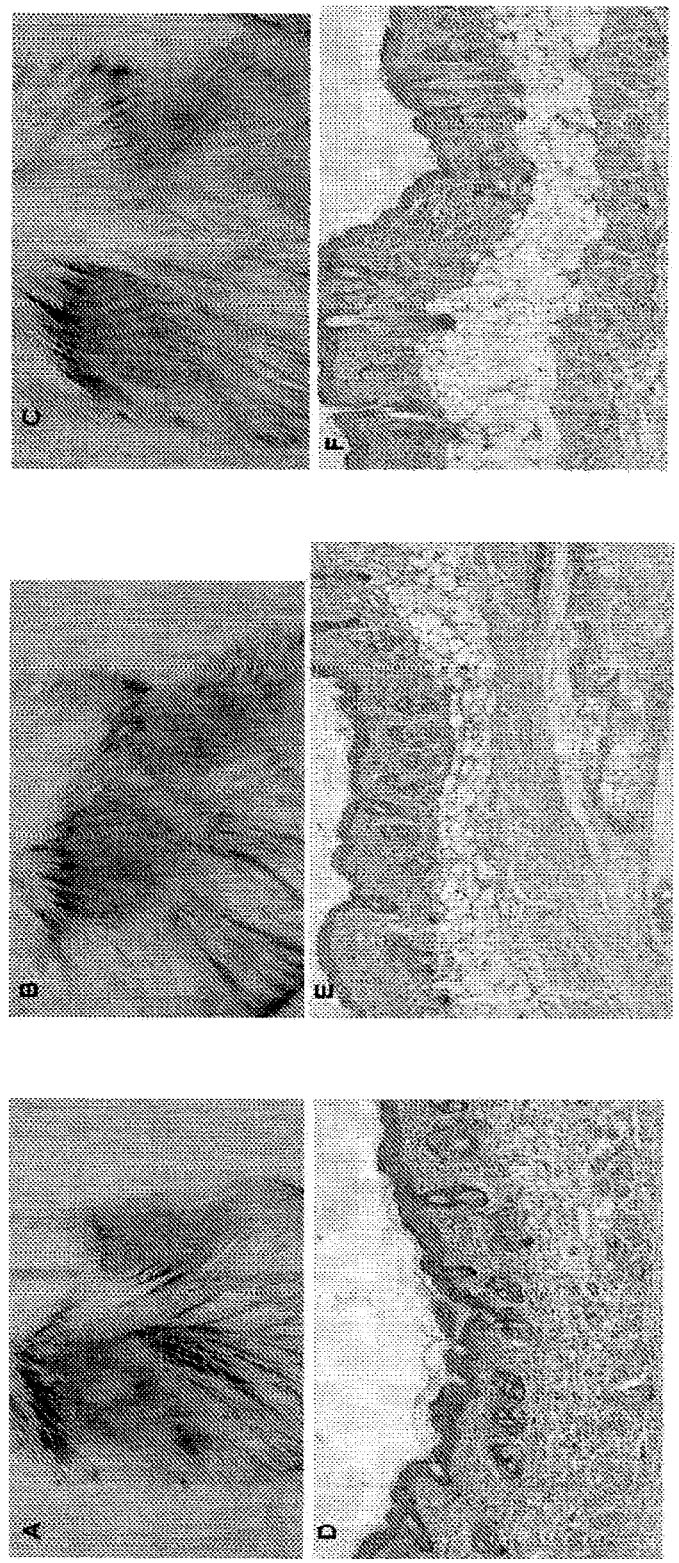
FIG. 11 shows SAGE (GM-111101) topical treatment in the LL-37 rosacea model, (a) Gross picture of LL-37 injected skin region, (b) SAGE treatment immediately after LL-37 injection and (c) SAGE treatment 12 h after LL-37 injection, (d) H&E-stained cross-sectional view of a LL-37 injected skin sample, (e) H&E-stained cross-sectional view of SAGE immediate treatment in LL-37 injected skin region, (f) H&E-stained cross-sectional view of SAGE 12 h treatment in LL-37 injected skin region, (g) MPO activity measurement of LL-37 injection model with different SAGE treatment strategies, (h) area of erythema and (g) erythema score demonstration of LL-37 rosacea model treated with topical application of SAGE.
Figure 11:
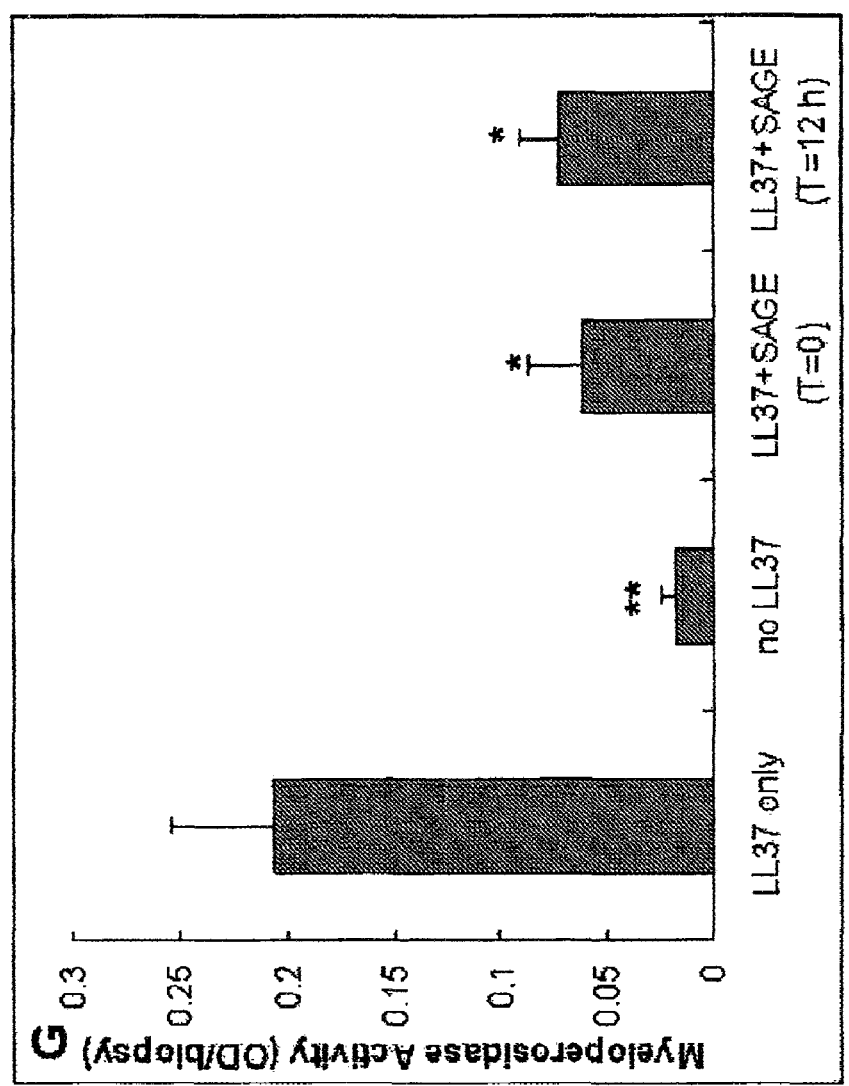
Figure 11:
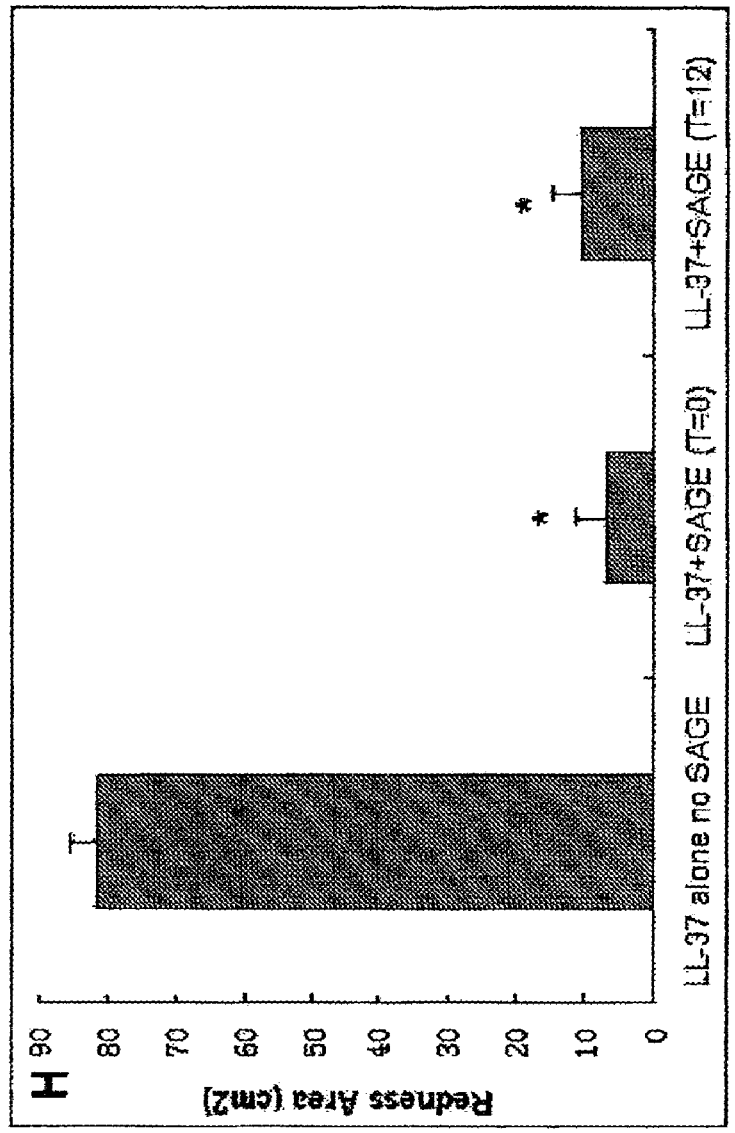
Figure 11:
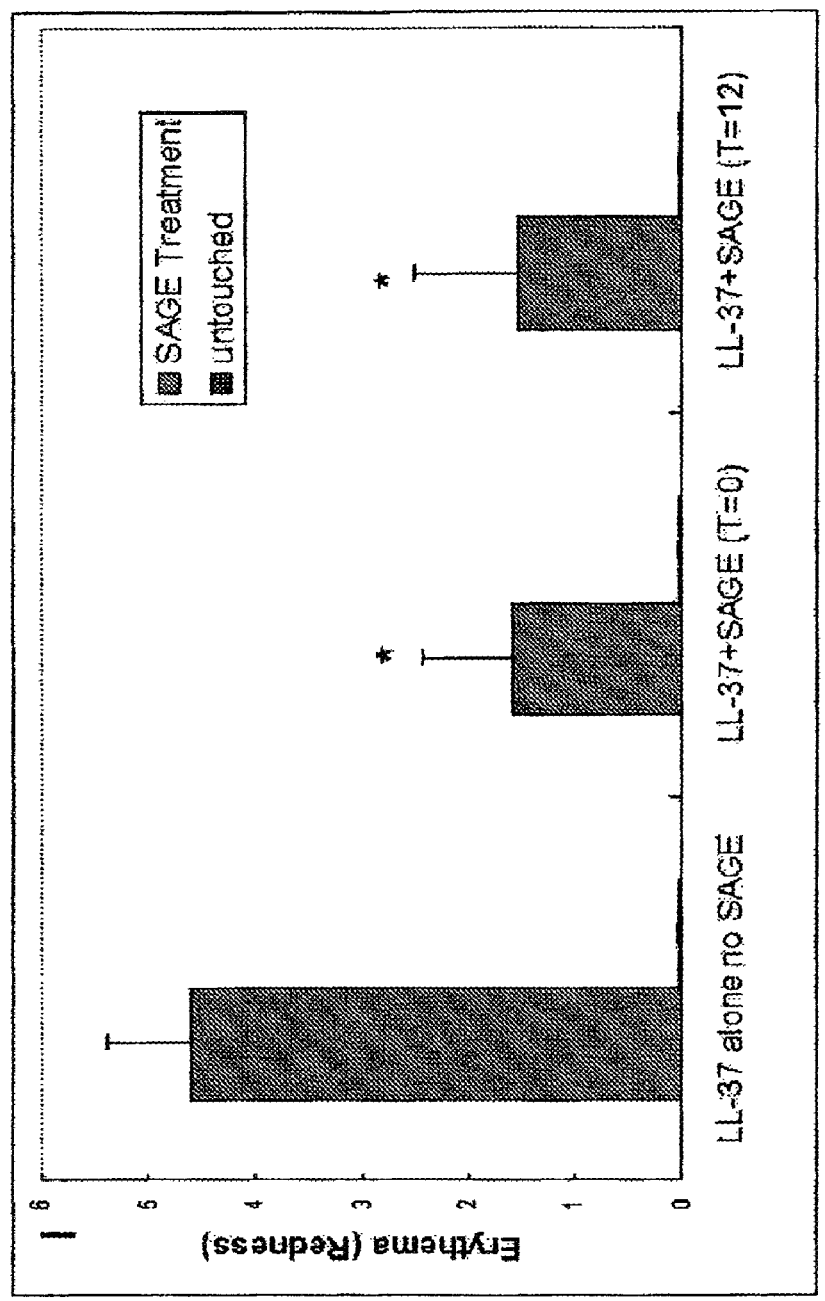

SAGE Topical Rosacea Treatment Model. Topical treatment of SAGE (GM-111101) is used to test if treatment remote in time from LL-37 exposure can also prevent peptide-induced skin inflammation. Therefore, after the LL-37 injection into the mouse back skin area, SAGE was applied right after. The gross pictures showed strong edema and erythema at 48 hours after the LL-37 application (FIGS. 11a, 11h, and 11i), while topical treatment with SAGE significantly decreased the redness and its affected area both for immediately treatment (FIGS. 11b) and 12 h delayed treatment (FIG. 11c). The H&E staining indicated much more leukocytic infiltration and dermal edema than the two SAGE treatment groups, which was in agreement with the results of SAGE as inhibitor of skin swelling response and MPO activities (FIG. 11g). These results indicate that SAGEs can be applied topically in a conventional and pharmaceutically acceptable emollient to treat the cathelicidin-mediated inflammation of rosacea.

Figure 12:
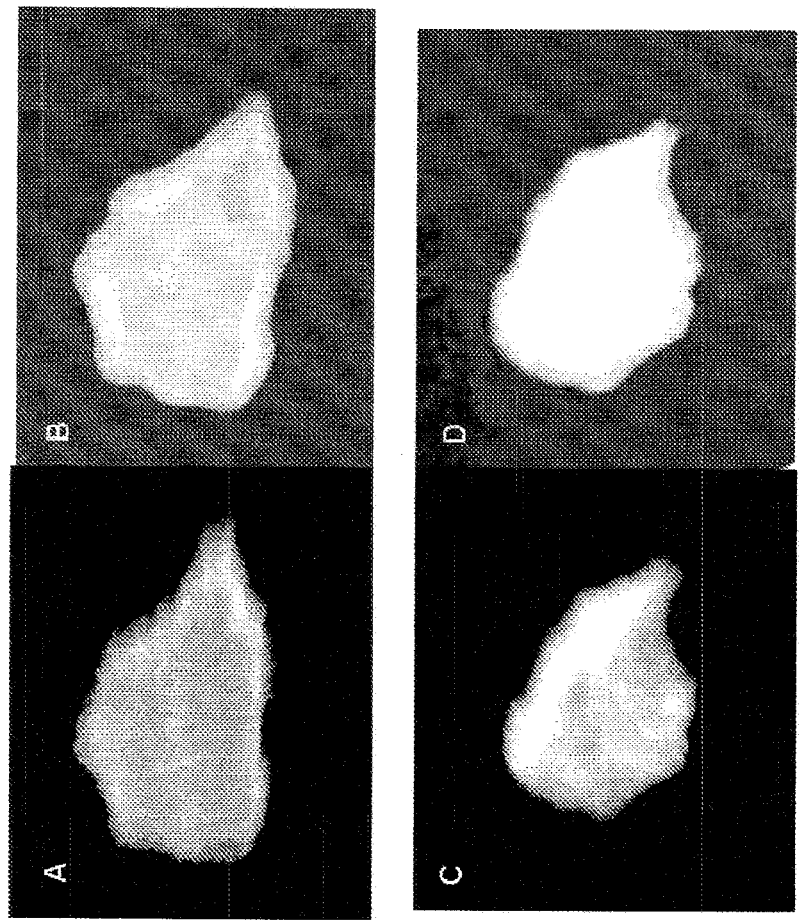
FIG. 12 shows the outer Skin under natural light (treated with 1 mg/ml fluorescently labeled SAGE) (Panel a) and outer Skin fluorescent image (Panel b); Inner Skin under natural light (Panel c) and inner skin under fluorescent condition (Panel d).

SAGE dermis penetration. To determine the level of which SAGE penetrates into the dermis. SAGE compound fluorescent-GM-212101 and fluorescent-GM-111101 were used as test article, and 0.1 mg/ml, 1 mg/ml and 10 mg/ml fluorescent compound were applied on the abraded and untouched skin area of Balb/c mice. After 24 hours, mice were sacrificed and the whole tested skin area was excised and photographed under both natural light and long wavelength UV light condition. (FIG. 12) Layers of fluorescence were observed under both natural and UV light condition for both inner and outer treatment area skin. Significant penetration of SAGEs was distributed even on a micrometer-length scale.

Figure 13:
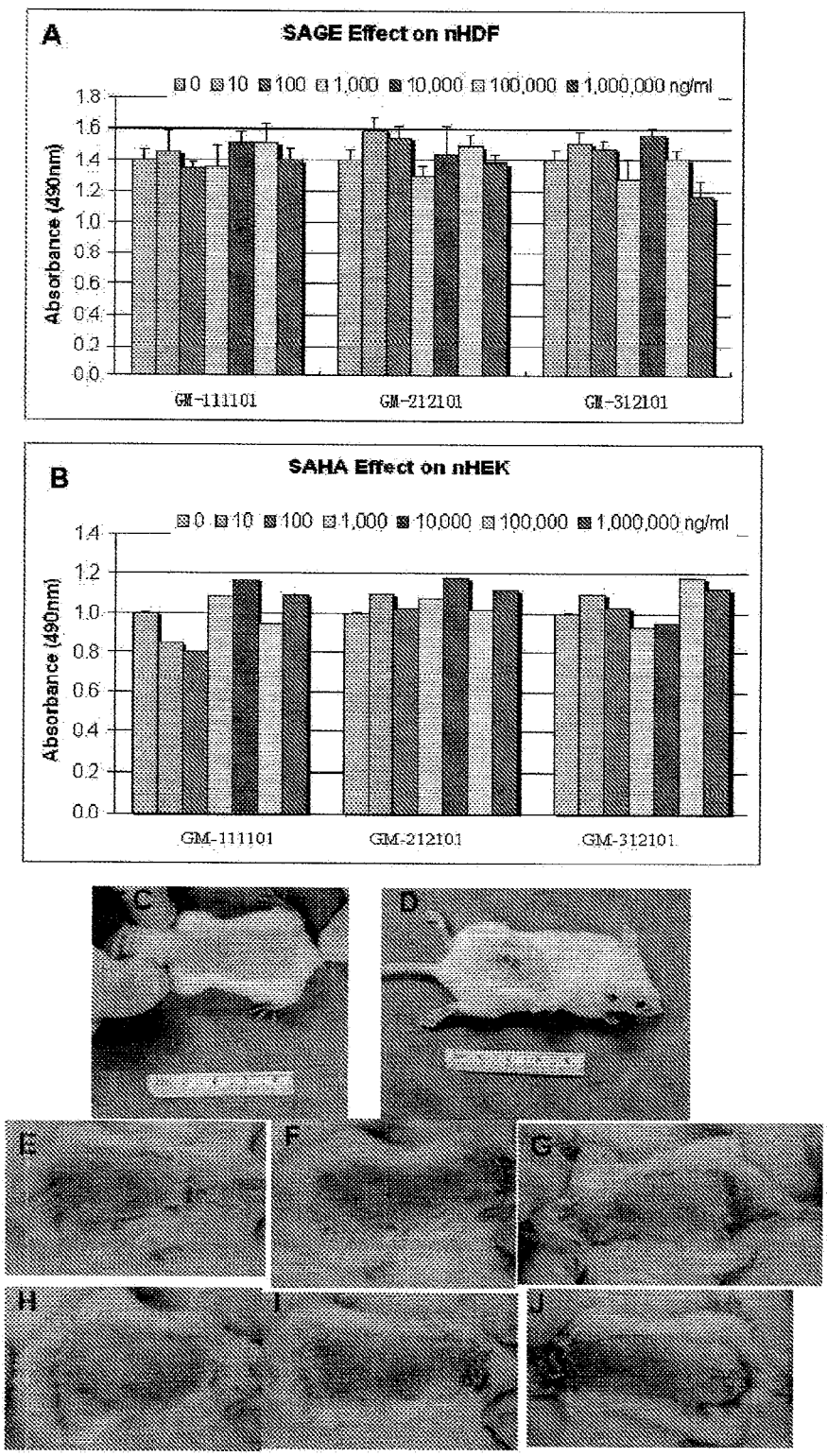
FIG. 13 shows the effects of HA derivatives on the proliferation of nHDF cells (a) and effect on nHEK (b) Gross pictures of mice treated with different concentrations of GM-111101 and GM-212101; the intact area (c) and formic acid irritated area (d) were compared with 0.1 mg/ml GM-111101 (e), 1 mg/ml GM-1 11101 (f), 10 mg/ml GM-111101 (g), 0.1 mg/ml GM-212101 (h), 1 mg/ml GM-212101 (i) and 10 mg/ml GM-212101 (j).
Figure 14:
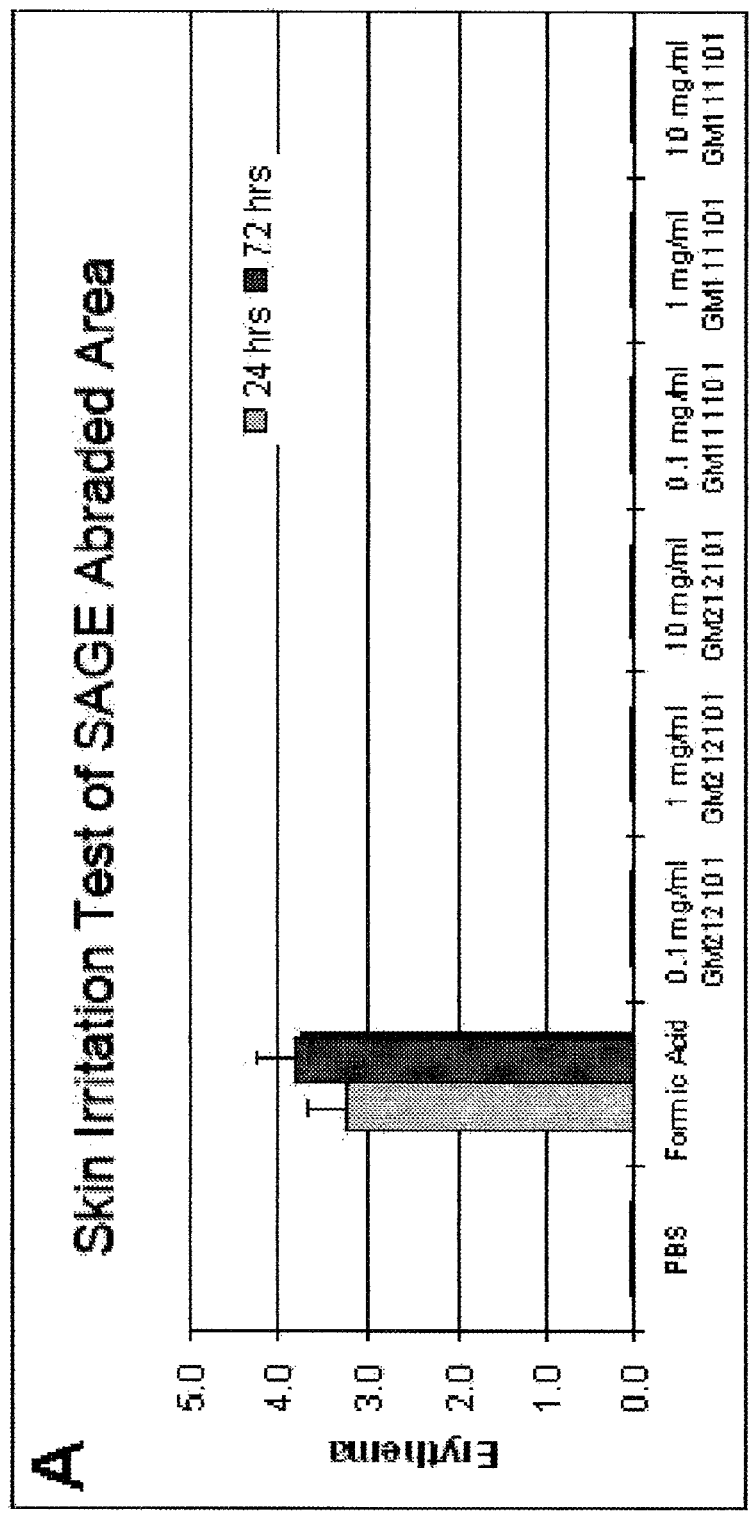
FIG. 14 shows the results of a skin irritation test in mice: (a) Erythema scoring of SAGE in abraded area, (b) Edema scoring of SAGE in abraded area (c) Erythema scoring of SAGE in intact area, (d) Edema scoring of SAGE in intact area.
Figure 14:
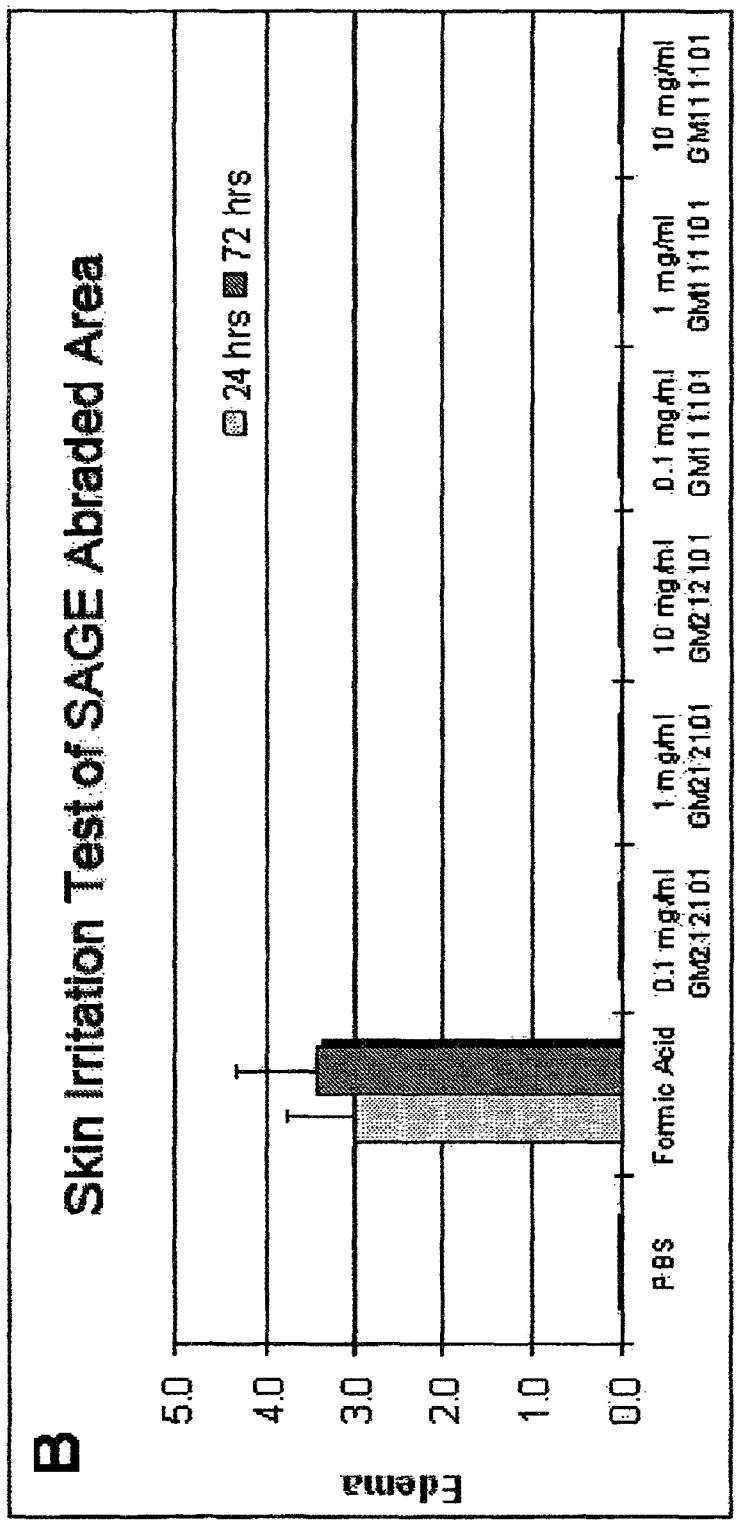
Figure 14:
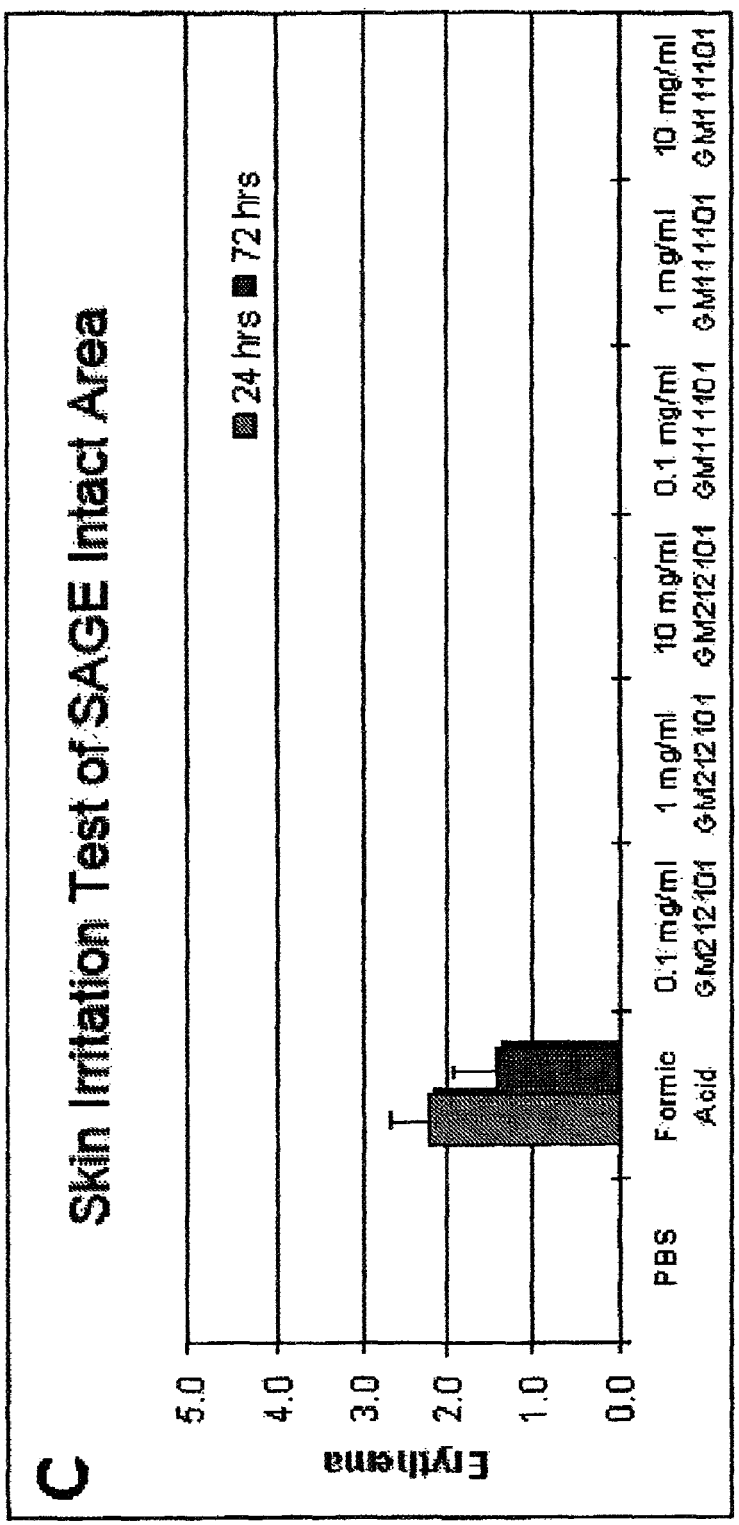
Figure 14:
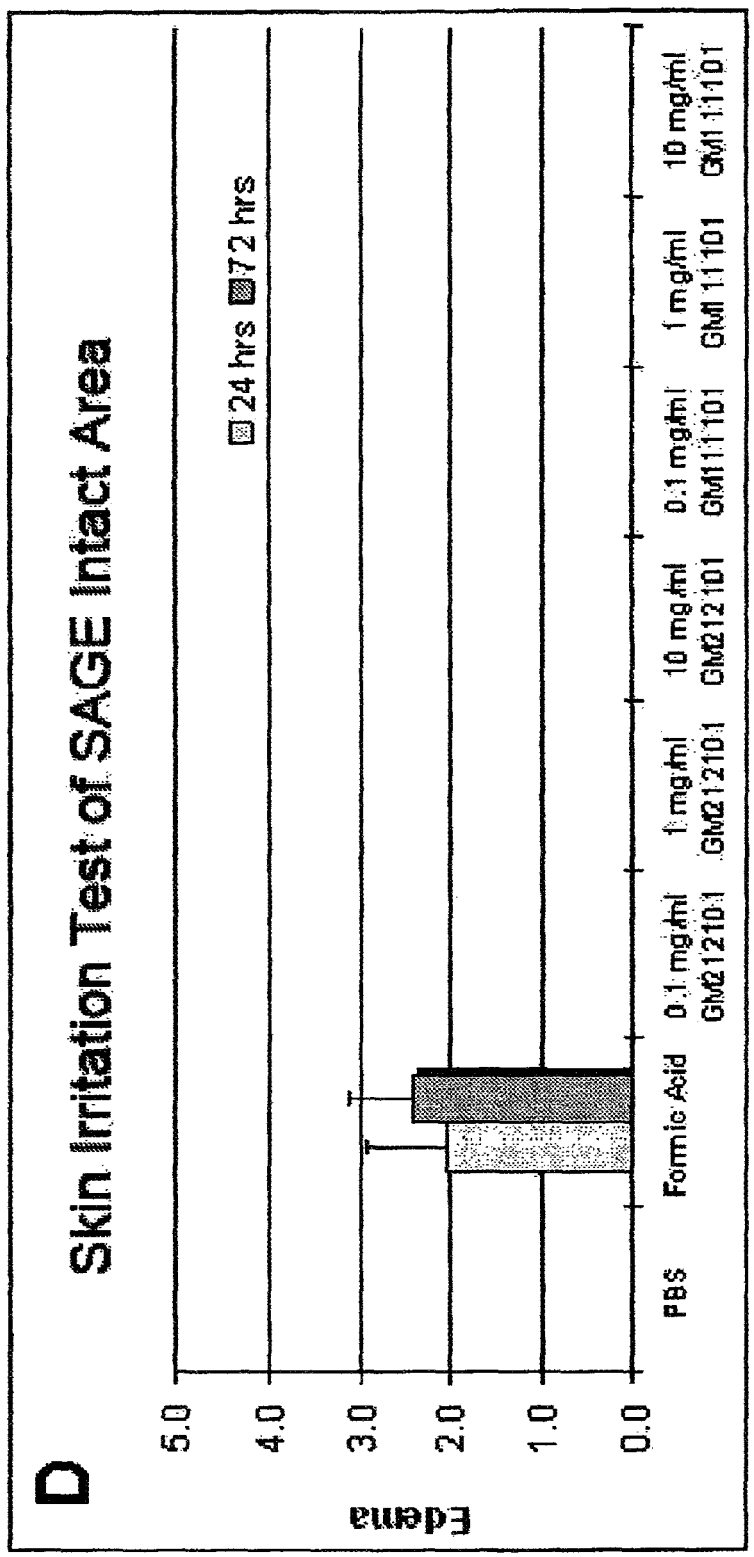

Cytotoxicity and Skin Irritation in Vivo Tests. The cytotoxicity of SAGE derivatives (SAGEs) GM-131101, GM-312101 and GM-212101 was evaluated in nHDF cells and the results are demonstrated in FIG. 13a. All compounds were also found to be non-toxic to the nHEK cells up to 10 mg/ml concentration (FIG. 13b). For the in vivo skin irritation tests, gross pictures of mice in different treatment groups were represented in FIG. 13c-13j. The Primary Irritation Index of the test substances was calculated to be 0.00 for both GM-111101 and GM-212101; No irritation were observed on the skin of the mice (FIG. 14). Both the GM-111101 and GM-212101 have not been found cytotoxic. The concentration threshold of all SAGEs could be determined from this test. Under the conditions of this test, the test agents would not be considered a primary skin irritant; as defined in the guidelines of the FHSA Regulations, 16 CFR 1500, a substance with an empirical score of less than 5.00 is not a primary irritant to the skin. These results indicate that SAGEs are non-irritating themselves for skin and can be employed as safe treatments for inflammatory skin disorders.

Figure 15:
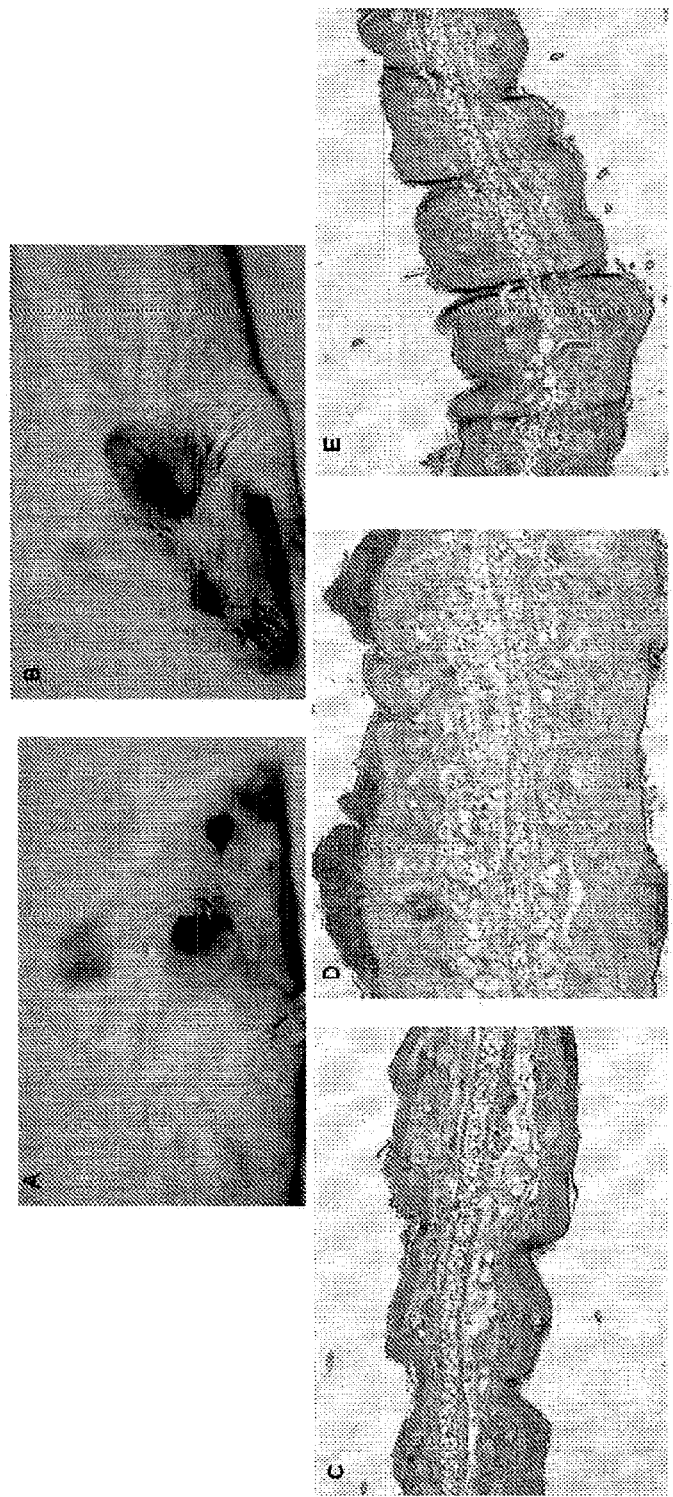
FIG. 15 shows topical SAGE treatment using *croton* oil inflammatory model. Four hours after *croton* oil treatment in control (CTL) group.
Figure 15:
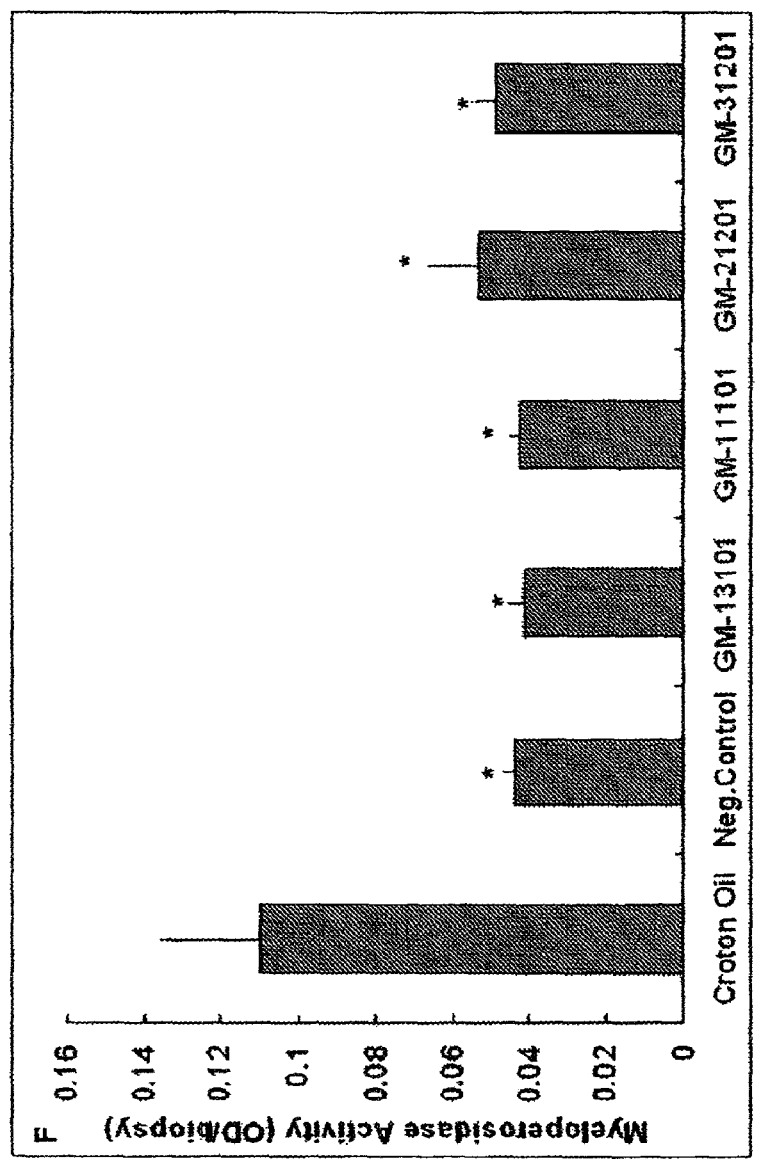
Figure 15:
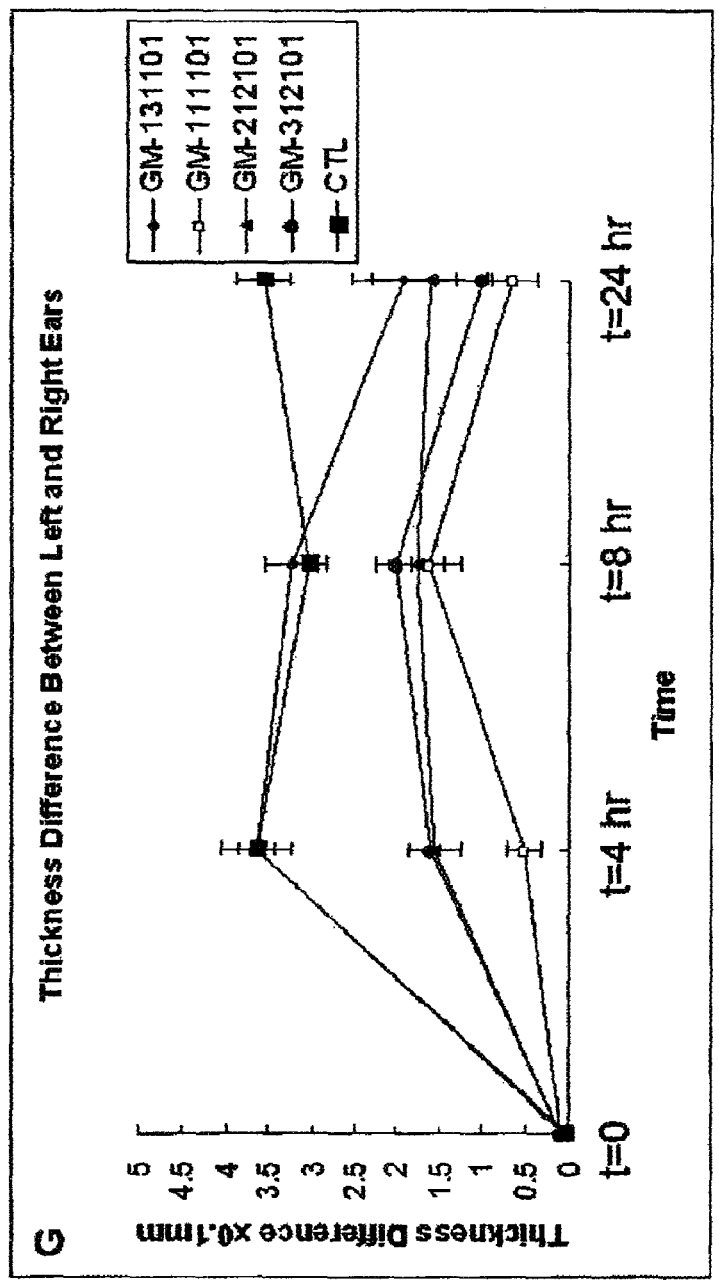
Figure 15:
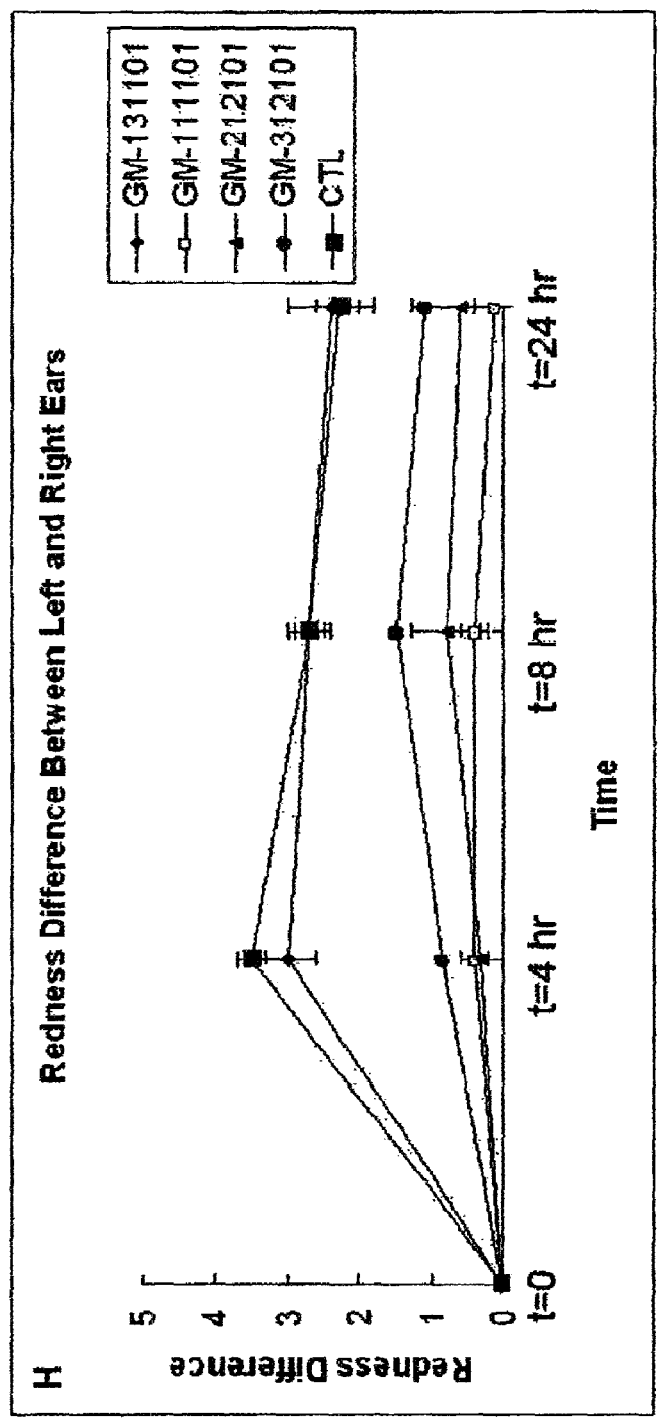

Croton oil inflammation model. The application of croton oil to mouse skin was used as a convenient and highly reproducible model of PMN-mediated skin inflammation. This model was used to test the anti-inflammatory activity of SAGEs. Gross pictures of mice in different treatment groups were represented in FIGS. 15a and 15b, as well as the ear thickness measured for both the treated and untreated ears, and compared in all the five groups. Individual results of dermal scoring were expressed by erythema for abraded area and intact area. The results showed significant reduction of redness and thickness in the SAGE (GM-111101) treatment groups compared with non-treatment groups (FIGS. 15g and 15h). Histopathological exams revealed that in croton oil painted ears, there was an increased number of leukocytic infiltration and marked dermal edema, whereas SAGE administration immediately after challenge resulted in the inhibition of ear swelling response, which was comparable to that of vehicle-treated mice. These histological findings further confirmed those of the measurement data. MPO activity was also measured in the ear punch biopsies taken after croton oil application. SAGE treatment every 4 hr starting immediately after croton oil application significantly reduced MPO activity (FIG. 15f). These results indicate that SAGEs can be employed as topical treatments for inflammatory skin disorders other than rosacea.

Figure 16:
FIG. 16 shows a comparison between Right (untreated) (Panel a) and Left (*croton* oil painted) (Panel b) ears of the same mouse in CTL group. H&E staining was done for negative control with PBS painting (Panel c), positive control with *croton* oil (Panel d) and *croton* oil followed by SAGE treatment (Panel e). Leukocytic infiltration and edema was identified in the *croton* oil positive control group. Myeloperoxidase activity (Panel f) is an index of polymorphonuclear leukocyte activation and was measured in ear punches after SAGE treatment. Panel g and Panel h are changes in ear thickness (from edema) and ear redness (from irritation) after SAGE treatment. ($p<0.05$)
Figure 16:
Figure 16:
Figure 16:
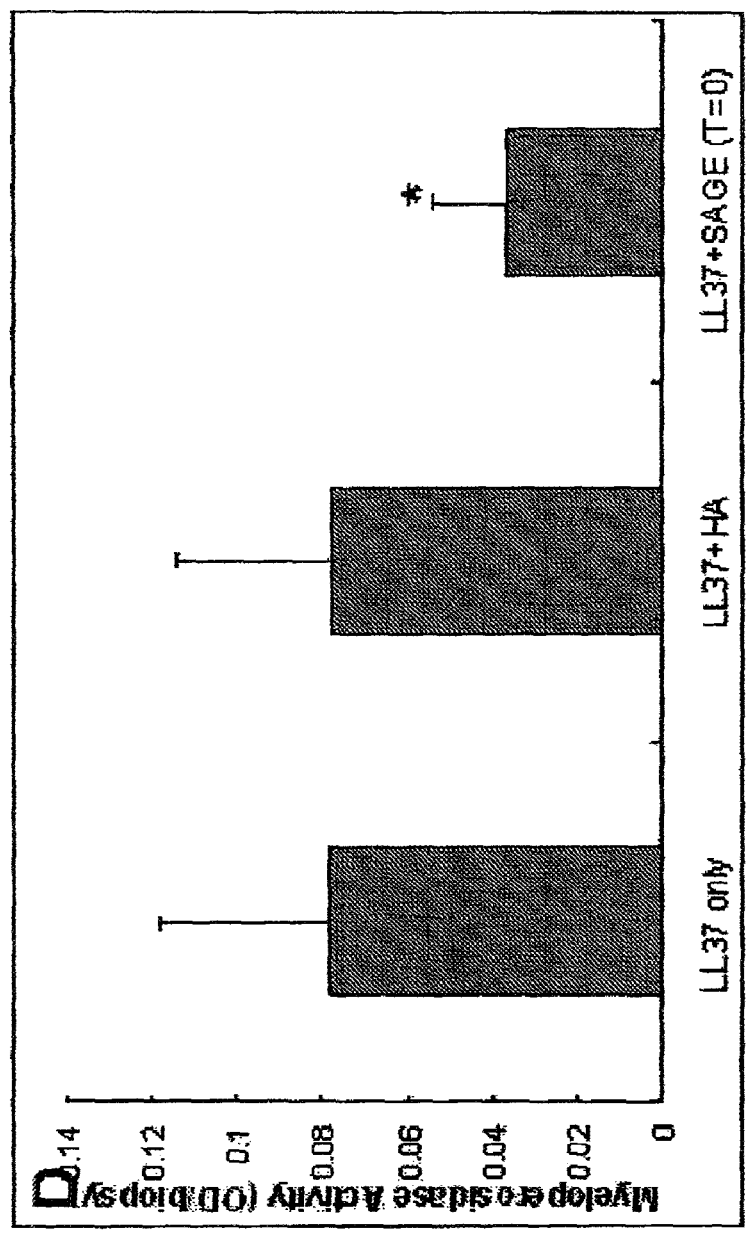
Figure 16:
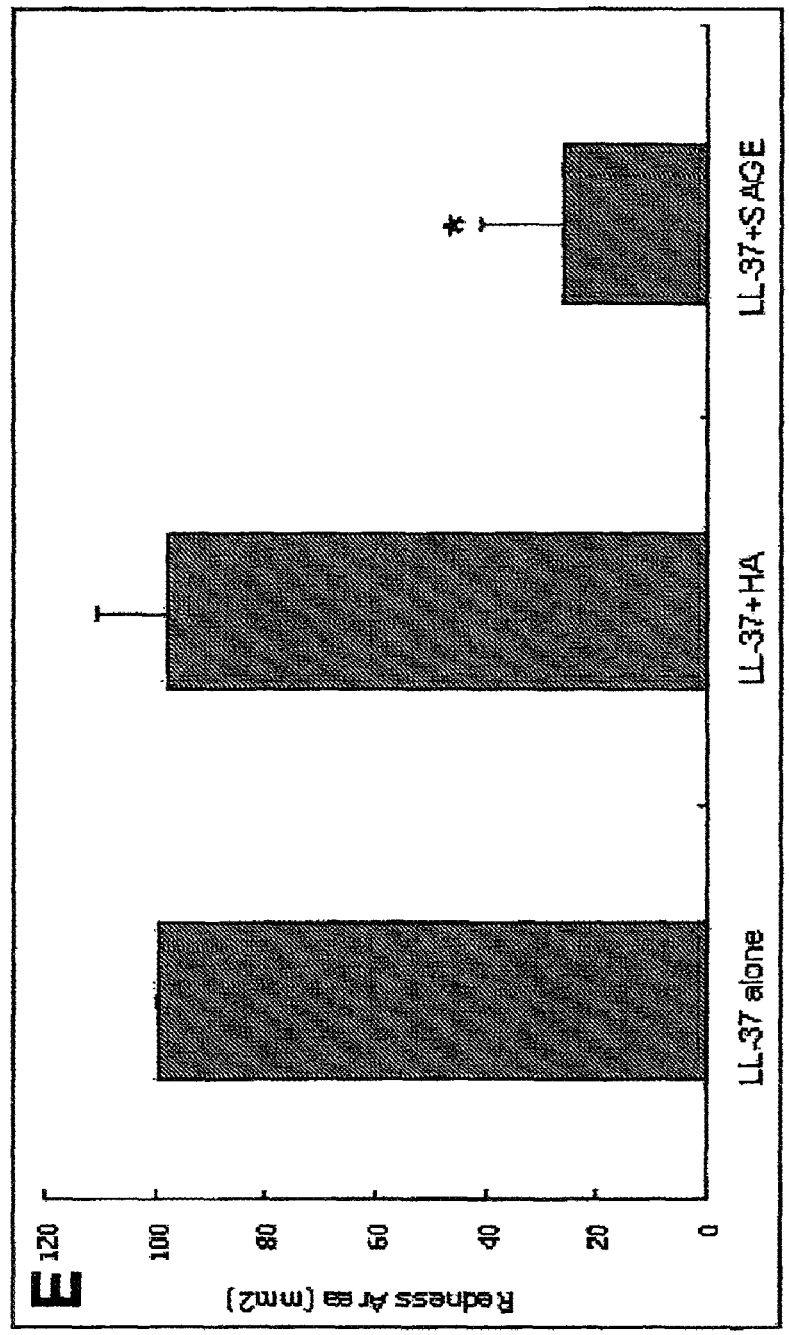
Figure 16:
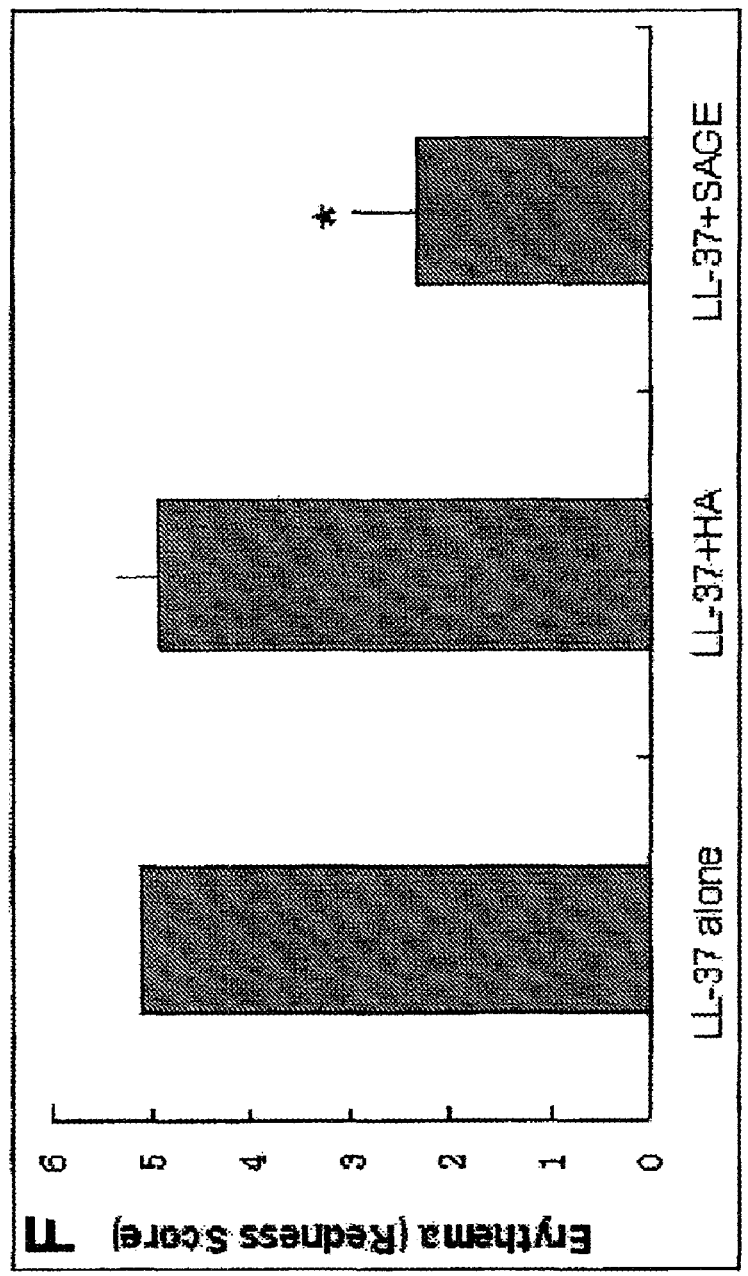

Hyaluronic Acid (HA) Topical Treatment in Rosacea Model. The previous topical treatment of LL-37 rosacea model was used to compare SAGE (GM-111101) vs. HA. The results clearly showed that HA in the topical administration did not alleviate inflammation (FIGS. 16b, 16e, and IT) and MPO activities (FIG. 16d). Conversely, SAGE possessed highly enhanced anti-inflammatory properties (FIG. 16c-f) and could be considered as an inhibitor of inflammatory and rosacea. These data indicate that the pharmacologic activity of SAGEs is not inherent in hyaluronic acid, but require the novel chemical modifications of hyaluronan. In Vivo Acute Intraveneous Toxicity Study in Rats. The objective of the study was to evaluate the acute intravenous toxicity of SAGEs GM-11 1101 and GM-212101 when administered as a single dose to rats and also to evaluate the toxicity of GM-11 1101 when administered once daily for a period of seven days at a single dose level.

One dose group consisting of three male and three female Sprague-Dawley rats was exposed to a single dose of 3 mg/kg GM-111101, then a single dose of 10 mg/kg GM-111101 one week following and finally once daily doses of 10 mg/kg GM-111101 for a total of seven days initiating one week following the last single dose. Two groups of three male and three female Sprague-Dawley rats were exposed to GM-111101 at doses of 30 or 100 mg/kg. In addition, two groups of three male and three female Sprague-Dawley rats were exposed to GM-212101 at doses of 30 or 100 mg/kg. Two groups of three male and three female Sprague-Dawley rats were exposed to 0.9% Sodium Chloride for Injection and were used as negative control groups. All doses were administered at a dose volume of 1 ml/kg by intravenous injection via the caudal tail vein. Dose calculations were determined based upon the most recently documented body weight.

All animals exposed acutely (single dose) were observed immediately following injection, and again at 2 hours and 4 hours following dose administration on Day 0 for apparent signs of clinical toxicity. In addition, all surviving animals were observed once daily on days 1-14 for apparent signs of clinical toxicity. All animals exposed once daily for seven days were observed once daily from days 1-14 for apparent signs of clinical toxicity. Body weight was recorded on day 0 (Acute dose) or day 1 (Repeat dose) prior to dose administration, on day 6 or 7, and on day 14, prior to termination. Gross necropsy evaluations were performed on each of the surviving animals on day 14 of the study. Animals that died on study underwent a gross necropsy examination immediately following observation of mortality.

Clinical signs of moderate abnormal gait, moderate ataxia, and reddish-orange discolored urine were observed in one female animal from the 30 mg/kg GM-212101 dose group within the first 2 hours following dose administration. These observations, with the exception of mild ataxia, were no longer present as of the 4 hour observation period and remained that way throughout the remainder of the study. The observation of ataxia was no longer present on the day following dose administration. In addition, one male rat from the 100 mg/kg GM-212101 dose group was found dead within the first four minutes following dose administration. All animals gained body weight throughout the study period. There were no visible lesions observed at necropsy with the exception of dark red foci measuring ~1-2 mm in diameter throughout the thymus in the one animal from the 100 mg/kg GM-212101 dose group that died on study. Based upon the results of this study, GM-111101 did not produce signs of toxicity at any of the dose levels evaluated, including single acute doses of 3, 10, 30, and 100 mg/kg and a seven day repeat dose of 10 mg/kg. Therefore, the no observable effect level (NOEL) for intravenous exposure to GM-111 101 in rats is considered to be at least 100 mg/kg. GM-212101 produced signs of toxicity or mortality at doses of 30 and 100 mg/kg. Therefore, the NOEL for intravenous exposure to GM-212101 in rats is considered to be 10 mg/kg. Due to the absence of mortality observed at all doses of GM-111 101 and mortality observed in only 17% of the animals at a dose of 100 mg/kg GM-212101, the intravenous LD50 in rats for GM-11 1 101 and GM-212101 is considered to be greater than 100 mg/kg. These results indicate that SAGEs are safe to employ as systemic or injected treatments for diseases.

VI. Investigation of SAGEs for Treating Age-Related Macular Degeneration

Figure 17:
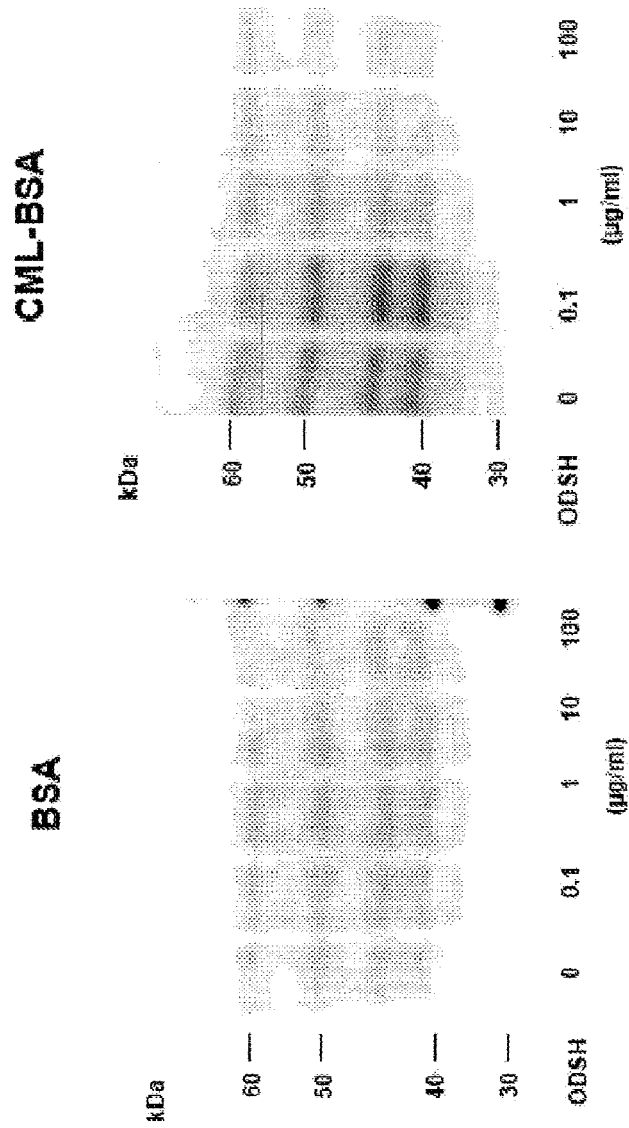
FIG. 17 shows AGE-induced RAGE expression in ARPE-19 cells is increased by growth on the AGE product carboxymethyl lysine-bovine serum albumin (CML-BSA) and prevented by modified heparin.

Activated complement and RAGE induce angiogenic and pro-inflammatory signaling in cultured RPE cells. Experiments studying the biology of RAGE in cultured RPE cells using the ARPE-19 human RPE cell line were consucted. As shown in immunoblots (FIG. 17), ARPE-19 cells express at least 4 isoforms of RAGE ranging from 45-50 kDa in cell lysates, and secrete these isoforms into conditioned media. When cells were grown on plates coated with the AGE product CML-BSA, expression of all four RAGE isoforms was markedly upregulated (compare right immunoblot to that on the left in FIG. 17). Because RAGE ligation activates the transcription factor NF-κB, enhanced expression of RAGE greatly promotes pro-inflammatory signaling. The addition of the nonanticoagulant heparin 2-O, 3-0 desulfated heparin (ODSH) to this system prevented up-regulation of RAGE expression by blocking interaction of CML-BSA with RAGE on ARPE-19 cells. This would prevent "feed-forward" pro-inflammatory increases in RAGE expression itself by RAGE ligation.

Figure 18:
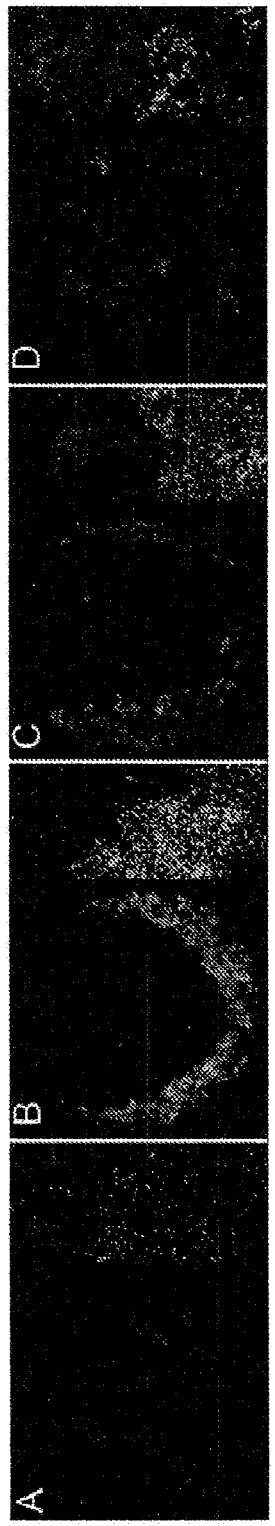
FIG. 18 shows that compared to control (a), the AGE product CML-BSA induces apoptosis in ARPE-19 cells (b) that is inhibited by ODSH (c) and almost eliminated by SAGE treatment (d).

The ability of AGE products to induce RPE cell apoptosis was investigated. ARPE-19 cells were grown to confluence on round coverslips, then transferred to new dishes for exposure to 25 μM AGE-BSA for 40 h. Apoptosis was then assayed with Molecular Probes Fixable Live/Dead Cell Stain Kit (LI 1101, Eugene, Oreg.). Each panel shows the entire coverslip and an enlarged view of the live/dead interface. Nuclei are stained red with DAPI; dead cells are stained green. A. BSA control. Some dead cells are noted at the edges of the coverslip, but live and dead cells are interspersed at the interface. B. AGE-BSA (25 μM). Significant cell death is seen around the edges, and the boundary between live and dead cells is stark. C. AGE-BSA (25 μM)+ODSH (200 μM). ODSH appears to provide some protection but significant apoptosis still occurs. D. AGE-BSA (25 μM)+P-OSMeHA (200 μM) (GM-11 1101). As shown in FIG. 18, AGE treatment of cultured ARPE-19 cells induced prominent apoptosis (FIG. 18B), measured by green staining with the Live/Dead Cell Stain kit (Molecular Probes). Apoptosis is reduced by concomitant incubation of cells with ODSH (FIG. 18C) but is almost completely prevented by an equivalent concentration of the SAGA P-OSMeHA (GM-1 11101) (FIG. 18D). Apoptosis appeared to advance inward from the edges of cells cultured on round cover slips. RAGE is prominently expressed in RPE cells where it may be selectively expressed on the basal membrane as in other human epithelial cells. Thus, in culture, AGE might initially be able to access and ligate basally located RAGE only at the edges of monolayers, producing a wave of cell death that predictably advances inward. In contrast, AGE in drusen, which accumulates between retinal pigment epithelium and Bruch's membrane, would have ready access to basally located RAGE, optimally positioning AGE/RAGE signaling to mediate the localized RPE apoptosis that constitutes so-called "geographic atrophy" in age-related macular degeneration. Thus, the SAGE GM-1 1 1 101 almost completely prevents AGE-induced RPE apoptosis. These results indicate that SAGEs might be effective in treatment of important eye diseases causing blindness, such as age-related macular degeneration.

SAGEs are non-toxic and non-anticoagulant. When O-sulfated and methylated HA (P-OSMeHA), fully O-sulfated and pentafluoropropylated HA (F-OSFHA-I) and fully O-sulfated and methylated HA (F-OSMeHA) were applied to cultured human skin epithelial cells or fibroblasts studied with a cell toxicity assay (CellTiter96® Aqueous One assay, Promega), the SAGEs do not inhibit proliferation or produce cell toxicity, even at concentrations of 1 mg/ml. The SAGEs also are non-anticoagulant. Low molecular weight sulfated and fluoroalkylated HAs demonstrate no anti-Xa and <0.2 U/mg anti-IIa anticoagulant activities, compared to 150 U/mg each for unfractionated heparin.

Figure 19:
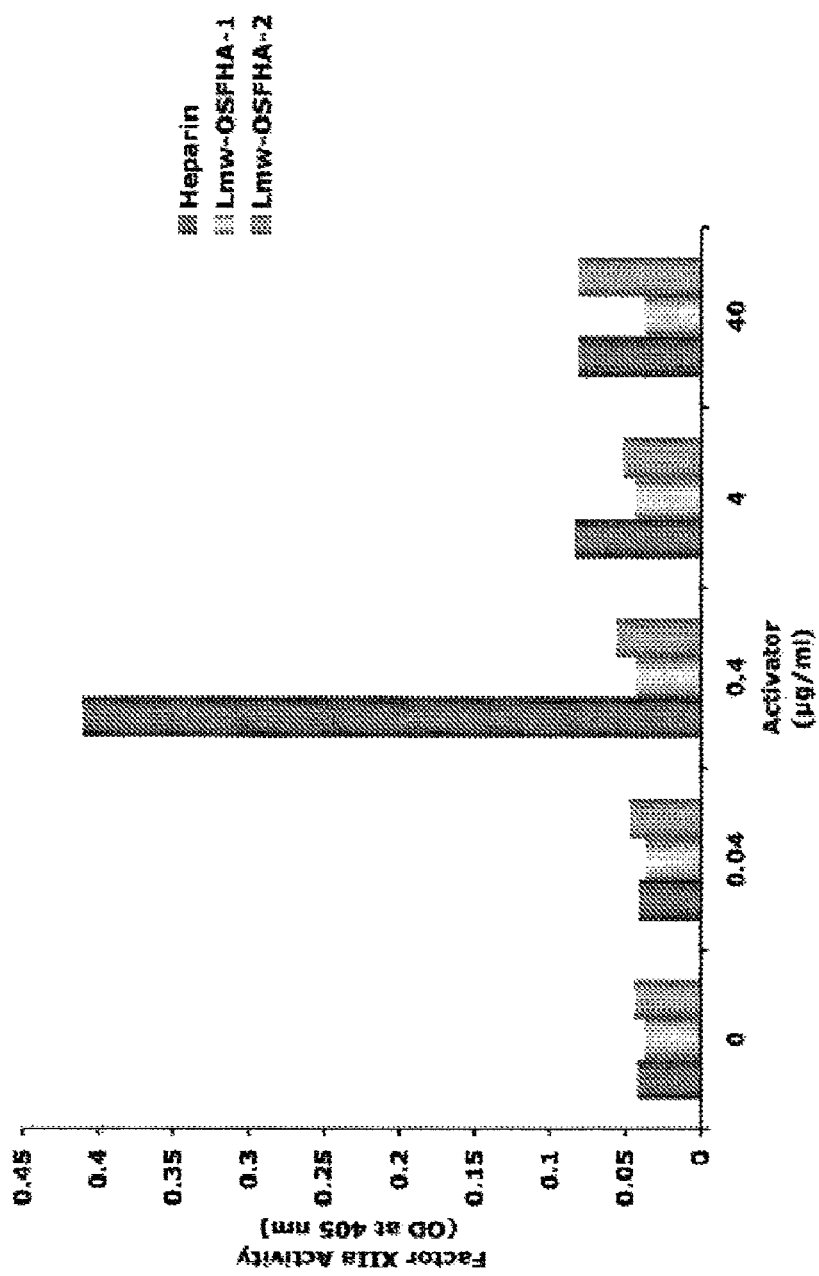
FIG. 19 shows that LMW SAGEs do not activate Factor XII, unlike heparin which activates Factor XII at a concentration of 0.4 µg/ml, which is close to the therapeutic anticoagulating plasma heparin concentration in humans.

Unlike heparin, highly-charged polyanionic polymers are potent inducers of the intrinsic or contact coagulation cascade through activation of Hageman factor (factor XIIa), secondarily activating kinins. SAGEs were screened for their ability to stimulate intrinsic coagulation (activation of Hageman factor). Pooled human plasma was incubated with heparin or low molecular weight (Lmw) sulfated and fluoroalkylated HAs (Lmw-OSFHA-1, Lmw-OSFHA-2) and amidolytic activity was determined using the substrate D-cyclohydrotyrosyl-Gly-Arg-p-NA. As shown in FIG. 19, low molecular weight (50 kDa) SAGEs appear even safer than commercial medical heparin when tested for ability to activate Factor XII, even at SAGE concentrations 10 to 100-fold higher than those achieving pharmacologic inhibition of inflammation.

Throughout this application, various publications are referenced. The disclosures of these publications in their entireties are hereby incorporated by reference into this application in order to more fully describe the compounds, compositions and methods described herein. Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

The invention claimed is:

1. A compound which is a modified hyaluronan or a pharmaceutically acceptable salt or ester thereof comprising at least one sulfate group and the primary C-6 hydroxyl proton of at least one N-acetyl-glucosamine residue substituted with an unsubstituted alkyl group or fluoroalkyl group, wherein the alkyl group is a $C_1$-$C_{10}$ branched or straight alkyl group and the fluoroalkyl group is defined by formula —$CH_2(CF_2)_nCF_3$, wherein n is an integer from 0 to 10.

2. The compound of claim 1, wherein the alkyl group is methyl, ethyl, propyl, isopropyl, butyl, pentyl, or hexyl.

3. The compound of claim 1, wherein the alkyl group is methyl.

4. The compound of claim 1, wherein n is 1, 2, 3, 4, or 5.

5. The compound of claim 1 wherein at least 1% of the primary C-6 hydroxyl protons of the N-acetyl-glucosamine residues are substituted with an unsubstituted alkyl group or fluoroalkyl group.

6. The compound of claim 1 wherein from 1% to 50% of the primary C-6 hydroxyl protons of the N-acetyl-glucosamine residues are substituted with an unsubstituted alkyl group or fluoroalkyl group.

7. The compound of claim 1 wherein the hyaluronan has a molecular weight greater than 10 kDa prior to alkylation or fluoroalkylation.

8. The compound of claim 1 wherein the hyaluronan has a molecular weight from 40 kDa to 2,000 kDa prior to alkylation or fluoroalkylation.

9. The compound of claim 1, wherein at least one C-2 hydroxyl proton or C-3 hydroxyl proton is substituted with a sulfate group.

10. The compound of claim 1, wherein at least one C-2 hydroxyl proton and C-3 hydroxyl proton are substituted with a sulfate group.

11. The compound of claim 1, wherein the compound has a degree of sulfation from 0.5 to 3.5 per disaccharide unit.

12. The compound of claim 1, wherein the alkyl group is methyl and at least one C-2 hydroxyl proton and/or C-3 hydroxyl proton is substituted with a sulfate group.

13. The compound of claim 1, wherein the alkyl group is methyl, at least one C-2 hydroxyl proton and/or C-3 hydroxyl proton is substituted with a sulfate group, and the compound has a molecular weight of 2 kDa to 10 kDa.

14. The compound of claim 1, wherein the fluoroalkyl group is —$CH_2CF_2CF_3$ or $CH_2CF_2CF_2CF_3$ and at least one C-2 hydroxyl proton and/or C-3 hydroxyl proton is substituted with a sulfate group.

15. The compound of claim 1, wherein the hyaluronan of said modified hyaluronan is not derived from an animal source.

16. A pharmaceutical composition comprising at least one pharmaceutically acceptable excipient and a compound of claim 1.

17. The composition of claim 16, wherein the composition comprises a pH of from 5 to 6.

18. A method for treating a skin disorder comprising applying a compound of claim 1 or a composition of claim 16 onto the surface of the skin, wherein the skin disorder is selected from the group consisting of rosacea, atopic dermatitis, allergic contact dermatitis, psoriasis, dermatitis herpetiformis, acne, diabetic skin ulcers, skin wounds, burns, sunburn, actinic keratoses, inflammation from insect bites, radiation-induced dermatitis/burn, and seborrheic dermatitis.

19. The method of claim 18, wherein the compound or composition is administered to reduce or inhibit the activity of P-selectin.

20. The method of claim 18, wherein the compound or composition is administered to reduce or inhibit the activation of the receptor for advanced glycation end-products (RAGE) by its various ligands.

21. The method of claim 18, wherein the compound or composition is administered to reduce or inhibit the activity of human leukocyte elastase.

22. The compound of claim 1, wherein a pharmaceutically acceptable base for the pharmaceutically acceptable salt is selected from ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, or histidine.

23. A method for treating an eye disorder comprising administering to the eye a compound of claim 1, wherein the eye disorder is age-related macular degeneration, diabetic retinopathy, dry eye syndrome, conjunctivitis, iritis, uveitis, allergic conjunctivitis, corneal inflammation or corneal scarring.

24. The composition of claim 16, wherein the composition is in a form of an ointment, lotion, cream, gel, drops, suppository, spray, liquid or powder.

* * * * *

UNITED STATES PATENT AND TRADEMARK OFFICE
CERTIFICATE OF CORRECTION

PATENT NO. : 8,399,430 B2
APPLICATION NO. : 12/870774
DATED : March 19, 2013
INVENTOR(S) : Prestwich et al.

It is certified that error appears in the above-identified patent and that said Letters Patent is hereby corrected as shown below:

In the Specification

Please insert the following paragraph at column 1, line 14:

--ACKNOWLEDGMENTS

This invention was made with government support under Grants T32 HL079874 and DK093413 awarded by the National Institutes of Health. The government has certain rights in the invention.--

Signed and Sealed this
Twenty-fourth Day of May, 2016

Michelle K. Lee
*Director of the United States Patent and Trademark Office*